(12) United States Patent
Chinen et al.

(10) Patent No.: US 8,012,722 B2
(45) Date of Patent: Sep. 6, 2011

(54) METHOD FOR PRODUCING L-AMINO ACID

(75) Inventors: Akito Chinen, Kawasaki (JP); Hisashi Yasueda, Kawasaki (JP); Jun Nakamura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 490 days.

(21) Appl. No.: 12/179,845

(22) Filed: Jul. 25, 2008

(65) Prior Publication Data

US 2010/0099152 A1  Apr. 22, 2010

Related U.S. Application Data

(63) Continuation of application No. PCT/JP2007/051837, filed on Jan. 29, 2007.

(30) Foreign Application Priority Data

Jan. 27, 2006  (JP) ................ 2006-019562

(51) Int. Cl.
| | |
|---|---|
| C12P 13/04 | (2006.01) |
| C12P 13/24 | (2006.01) |
| C12P 13/22 | (2006.01) |
| C12P 13/12 | (2006.01) |
| C12P 13/10 | (2006.01) |
| C12P 13/08 | (2006.01) |
| C12P 13/06 | (2006.01) |

(52) U.S. Cl. ........ 435/106; 435/107; 435/108; 435/113; 435/114; 435/115; 435/116

(58) Field of Classification Search .......... 435/106–108, 435/113–116
See application file for complete search history.

(56) References Cited

U.S. PATENT DOCUMENTS

| | | | |
|---|---|---|---|
| 4,757,009 | A | 7/1988 | Sano et al. |
| 5,569,595 | A | 10/1996 | Dennis |
| 5,891,686 | A | 4/1999 | Dennis et al. |
| 6,878,533 | B2 | 4/2005 | Tsujimoto et al. |
| 6,911,332 | B2 | 6/2005 | Usuda et al. |
| 7,026,149 | B2 | 4/2006 | Usuda et al. |
| 7,029,893 | B2 | 4/2006 | Usuda et al. |
| 7,060,475 | B2 | 6/2006 | Usuda et al. |
| 7,160,704 | B2 | 1/2007 | Takeshita et al. |
| 7,169,587 | B2 | 1/2007 | Gunji et al. |
| 7,192,747 | B2 | 3/2007 | Ono et al. |
| 7,192,748 | B2 | 3/2007 | Usuda et al. |
| 7,205,132 | B2 | 4/2007 | Hirano et al. |
| 7,211,416 | B2 | 5/2007 | Asahara et |
| 7,211,421 | B2 | 5/2007 | Tsujimoto et al. |

(Continued)

FOREIGN PATENT DOCUMENTS

EP    1 092 776    4/2001

(Continued)

OTHER PUBLICATIONS

Database EMBL [Online], Sep. 1, 1996, "C. glutamicum pta gene and ackA gene," XP002429912.

Database Geneseq [Online], Nov. 3, 2005, "Corynebacterium glutamicum HA protein coding sequence—SEQ ID 303," XP002429913.

(Continued)

*Primary Examiner* — Tekchand Saidha
(74) *Attorney, Agent, or Firm* — Shelly Guest Cermak; Cermak Nakajima LLP

(57) ABSTRACT

L-amino acids such as L-glutamic acid, L-glutamine, L-proline, L-arginine, L-leucine, and L-cysteine are produced by culturing in a medium a bacterium having an L-amino acid-producing ability and wherein the bacterium has been modified so that the phosphotransacetylase activity is enhanced.

8 Claims, 1 Drawing Sheet

U.S. PATENT DOCUMENTS

| | | |
|---|---|---|
| 7,217,543 B2 | 5/2007 | Gunji et al. |
| 7,220,570 B2 | 5/2007 | Usuda et al. |
| 7,223,572 B1 | 5/2007 | Gunji et al. |
| 7,335,506 B2 | 2/2008 | Gunji et al. |
| 2004/0146974 A1 | 7/2004 | Gunji et al. |
| 2004/0152175 A1 | 8/2004 | Nakamura et al. |
| 2005/0176121 A1 | 8/2005 | Takeshita et al. |
| 2006/0019356 A1 | 1/2006 | Usuda et al. |
| 2006/0030010 A1 | 2/2006 | Usuda et al. |
| 2006/0030011 A1 | 2/2006 | Usuda et al. |
| 2006/0040365 A1 | 2/2006 | Kozlov et al. |
| 2006/0141588 A1 | 6/2006 | Nakamura et al. |
| 2007/0172932 A1 | 7/2007 | Hirano et al. |
| 2007/0249017 A1 | 10/2007 | Usuda et al. |
| 2007/0254345 A1 | 11/2007 | Fukui et al. |
| 2008/0038825 A1 | 2/2008 | Gunji et al. |

FOREIGN PATENT DOCUMENTS

| | | |
|---|---|---|
| JP | 09009982 | 1/1997 |
| WO | WO03/078643 | 9/2003 |
| WO | WO2006/016705 | 2/2006 |

OTHER PUBLICATIONS

Pharkya, P., et al., "Exploring the Overproduction of Amino Acids Using the Bilevel Optimization Framework OptKnock," Biotechnol. Bioeng. 2003;84(7):887-899.

Wendisch, V. F., et al., "Metabolic engineering of *Escherichia coli* and *Corynebacterium glutamicum* for biotechnological production of organic acids and amino acids," Curr. Op. Microbiol. 2006;9(3):268-274.

International Search Report and Written Opinion of the International Searching Authority for PCT Patent App. No. PCT/JP2007/051837 (May 9, 2007).

Gerstmeir, R., et al., "RamB, a Novel Transcriptional Regulator of Genes Involved in Acetate Metabolism of *Corynebacterium glutamicum*," J. Bacteriol. 2004;186(9):2798-2809.

Reinscheid, D. J., et al., "Cloning, sequence analysis, expression and inactivation of the Corynebacterium glutamicum pta-ack operon encoding phosphotransacetylase and acetate kinase," Microbiol. 1999;145:503-513.

International Preliminary Report on Patentability for PCT Patent App. No. PCT/JP2007/051837 (Aug. 7, 2008).

Gottschalk., G., Bacterial Metabolism, Second Edition, 1986, Springer Verlag, pp. 214-225.

SEQUENCE LISTING

```
<160> NUMBER OF SEQ ID NOS: 65

<210> SEQ ID NO 1
<211> LENGTH: 20
<212> TYPE: DNA
<213> ORGANISM: Artificial sequence
<220> FEATURE:
<223> OTHER INFORMATION: primer

<400> SEQUENCE: 1
ccaggcactc gtcctcggtt                                                    20

<210> SEQ ID NO 2
<211> LENGTH: 48
<212> TYPE: DNA
<213> ORGANISM: Artificial sequence
<220> FEATURE:
<223> OTHER INFORMATION: primer

<400> SEQUENCE: 2
aggctagtgc aggactataa agaccagttc tcctaaaaat aacgtgtc                     48

<210> SEQ ID NO 3
<211> LENGTH: 48
<212> TYPE: DNA
<213> ORGANISM: Artificial sequence
<220> FEATURE:
<223> OTHER INFORMATION: primer

<400> SEQUENCE: 3
gacacgttat ttttaggaga actggtcttt atagtcctgc actagcct                     48

<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4
tccatcgtgg ccaccgatcc                                                    20

<210> SEQ ID NO 5
<211> LENGTH: 25
<212> TYPE: DNA
<213> ORGANISM: Artificial sequence
<220> FEATURE:
<223> OTHER INFORMATION: primer

<400> SEQUENCE: 5
cgggatcccc accggcgtac tcgtg                                              25

<210> SEQ ID NO 6
<211> LENGTH: 28
<212> TYPE: DNA
<213> ORGANISM: Artificial sequence
<220> FEATURE:
<223> OTHER INFORMATION: primer
```

-continued

```
<400> SEQUENCE: 6
ccacggatcc ttccaatgct attggttg                                              28

<210> SEQ ID NO 7
<211> LENGTH: 4942
<212> TYPE: DNA
<213> ORGANISM: Corynebacterium glutamicum
<220> FEATURE:
<221> NAME/KEY: CDS
<222> LOCATION: (1437)..(2705)

<400> SEQUENCE: 7
gatcttgccg atttcggcag gatcaatgtc ggcgtgaatg atcttggcat caggtgcgaa           60
agtgtcaacg tcaccggtga cgcggtcatc aaagcgggag ccgatagcaa tcagcaggtc          120
gctgcgctgc agtgcaccaa cagcggacac agtgccatgc atgcctggca tacccatgtg          180
cagctcgtgg gactctggga aggttcccag cgccatcaat gtggtgacaa ctggaatgcc          240
ggtgtgctca gcgaacgcac gaagctcttc gtgggcatca gccttgataa cgccgccgcc          300
aacgtaaagg acaggcttct tagactcacc gatcagtttg acagcctgct caatctgtcg          360
agcatgcggt gttgaaactg gcggtagcc tggcaggtcg atctttggtg ccagacgaa            420 atccaattca gcgttctgaa catccttggg gatatccact agaacaggac cagggcgacc          480
agtaatcgcg aggtggaatg cctcagccaa tgcctgtgga atgtcgttgg ggttggtgac          540
catgaagttg tgcttggtca ctggcatggt gatgccgcgg atatcggctt cctggaaagc          600
atcggtaccc agcaggctac ttccgacctg gccggtgatg caaccatgg gaacggagtc          660 caagtttgca tcagcgattg gggtaaccaa gttggttgcg cctgggccag aggttgcaat          720
gcagacgcca acgcgtccag taacctgcgc gtagccggtt gctgcgtggc ctgcgccctg          780
ctcgtggcgc actaggacgt ggcgcacctt tgtggaggaa tagagcgggt catacaccgg          840
tagcaccgca ccaccaggaa taccgaacac gatgtcggcg ttaagctcct cgagcgatcg          900
aacaattgcc tgtgcacctg tcatccgctc aggggcggcg gatcgaccac ggcttgcaac          960
cgtggcggga gtgggctgtt gagaagctgc cacattcacg actttctggc tcctttacta         1020
aataaggatt ttcacaggac ccgtccaagc caagccgatt tcaactcagc ctaaagacaa         1080
agccctcatt taaaattgtt ccgacgcgga tgcgtgtgca cgcagtgcga cagatgtctg         1140
ttgcaaagtt ggctacttgg gtcataacca acaagaaagc cctcgttcca acactgtggt         1200
gagtgttgtc gagggcgctt gacgagacga cttggaaggc cgttacggca ggcgccgcgc         1260
ggttactact acaagtcgaa taatggtcat ggtgtgtcat gctacacaca tcgagtttcc         1320
aattccacaa cgcacgaaaa ttcccacccc caaaactccc ccacttcggt taaggaatca         1380
ggattctcac aaagttcagg caggctcccg ctactttca gcgctaatct tggctc atg          1439
                                                                     Met
                                                                      1 att tta ggc gta ccc att caa tat ttg ctc tat tca ttg tgg aat tgg           1487
Ile Leu Gly Val Pro Ile Gln Tyr Leu Leu Tyr Ser Leu Trp Asn Trp
        5                  10                  15 att gtc gat acc ggt ttt gat gta gca att atc ctg gtc ttg gcg ttt           1535
Ile Val Asp Thr Gly Phe Asp Val Ala Ile Ile Leu Val Leu Ala Phe
    20                  25                  30 ttg att cca cgt atc ggc cga ctg gcc atg cgt att atc aag cag cga           1583
Leu Ile Pro Arg Ile Gly Arg Leu Ala Met Arg Ile Ile Lys Gln Arg
35                  40                  45 gtg gag tct gca gcc gat gcg gac acc act aag aac cag ctc gcg ttc           1631
Val Glu Ser Ala Ala Asp Ala Asp Thr Thr Lys Asn Gln Leu Ala Phe
50                  55                  60                  65
```

| | |
|---|---|
| gct ggc gtt ggc gtt tat atc gcg caa att gtg gcg ttt ttc atg ctt<br>Ala Gly Val Gly Val Tyr Ile Ala Gln Ile Val Ala Phe Phe Met Leu<br>           70                    75                   80 | 1679 |
| gcc gtc tcc gcg atg cag gct ttt ggt ttc tct ctc gcg ggc gct gcg<br>Ala Val Ser Ala Met Gln Ala Phe Gly Phe Ser Leu Ala Gly Ala Ala<br>         85                    90                    95 | 1727 |
| att ccg gca acc att gcg tca gct gcc att ggt ctt ggt gcg cag tcg<br>Ile Pro Ala Thr Ile Ala Ser Ala Ala Ile Gly Leu Gly Ala Gln Ser<br>100                   105                    110 | 1775 |
| att gtt gcg gac ttc ttg gcc gga ttt ttc atc ctg acg gaa aag caa<br>Ile Val Ala Asp Phe Leu Ala Gly Phe Phe Ile Leu Thr Glu Lys Gln<br>115                   120                    125 | 1823 |
| ttc ggc gtg ggt gac tgg gtg cgc ttt gag ggc aac ggc atc gtt gtt<br>Phe Gly Val Gly Asp Trp Val Arg Phe Glu Gly Asn Gly Ile Val Val<br>130                   135                 140           145 | 1871 |
| gaa ggc acc gtc att gag atc acc atg cgc gcg acc aaa att cgc acg<br>Glu Gly Thr Val Ile Glu Ile Thr Met Arg Ala Thr Lys Ile Arg Thr<br>                150                 155               160 | 1919 |
| att gca caa gag acc gtg atc atc ccg aac tcc acg gcg aaa gtg tgc<br>Ile Ala Gln Glu Thr Val Ile Ile Pro Asn Ser Thr Ala Lys Val Cys<br>              165                 170               175 | 1967 |
| atc aac aat tct aat aac tgg tcg cgt gcg gtt gtc gtt att ccg atc<br>Ile Asn Asn Ser Asn Asn Trp Ser Arg Ala Val Val Val Ile Pro Ile<br>180                   185                    190 | 2015 |
| ccc atg ttg ggt tct gaa aac atc aca gat gtc atc gcg cgc tct gaa<br>Pro Met Leu Gly Ser Glu Asn Ile Thr Asp Val Ile Ala Arg Ser Glu<br>         195                 200               205 | 2063 |
| gct gcg act cgt cgc gca ctt ggc cag gag aaa atc gca ccg gaa atc<br>Ala Ala Thr Arg Arg Ala Leu Gly Gln Glu Lys Ile Ala Pro Glu Ile<br>210                   215                 220         225 | 2111 |
| ctc ggt gaa ctc gat gtg cac cca gcc acg gaa gtc aca ccg cca acg<br>Leu Gly Glu Leu Asp Val His Pro Ala Thr Glu Val Thr Pro Pro Thr<br>              230                 235               240 | 2159 |
| gtg gtc ggc atg ccg tgg atg gtc acc atg cgt ttc ctc gtg caa gtc<br>Val Val Gly Met Pro Trp Met Val Thr Met Arg Phe Leu Val Gln Val<br>                245                 250               255 | 2207 |
| acc gcc ggc aat caa tgg ctg gtc gaa cgc gcc atc cgc aca gaa atc<br>Thr Ala Gly Asn Gln Trp Leu Val Glu Arg Ala Ile Arg Thr Glu Ile<br>                260                 265               270 | 2255 |
| atc aac gaa ttc tgg gaa gaa tac ggc agc gca acc act aca tcg gga<br>Ile Asn Glu Phe Trp Glu Glu Tyr Gly Ser Ala Thr Thr Thr Ser Gly<br>275                   280                    285 | 2303 |
| acc ctc att gat tcc tta cac gtt gag cat gaa gag cca aag acc tcg<br>Thr Leu Ile Asp Ser Leu His Val Glu His Glu Glu Pro Lys Thr Ser<br>290                   295                 300         305 | 2351 |
| ctt atc gac gcc tcc ccc cag gct ctt aag gaa ccg aag ccg gag gct<br>Leu Ile Asp Ala Ser Pro Gln Ala Leu Lys Glu Pro Lys Pro Glu Ala<br>              310                 315               320 | 2399 |
| gcg gcg acg gtt gca tcg cta gct gca tcg tct aac gac gat gca gac<br>Ala Ala Thr Val Ala Ser Leu Ala Ala Ser Ser Asn Asp Asp Ala Asp<br>                325                 330               335 | 2447 |
| aat gca gac gcc tcg gcg atc aat gca ggc aat cca gag aag gaa ctt<br>Asn Ala Asp Ala Ser Ala Ile Asn Ala Gly Asn Pro Glu Lys Glu Leu<br>              340                 345               350 | 2495 |
| gat tcc gat gtg ctg gaa caa gaa ctc tcc agc gaa gaa ccg gaa gaa<br>Asp Ser Asp Val Leu Glu Gln Glu Leu Ser Ser Glu Glu Pro Glu Glu<br>355                   360                    365 | 2543 |
| aca gca aaa cca gat cac tct ctc cga ggc ttc ttc cgc act gat tac<br>Thr Ala Lys Pro Asp His Ser Leu Arg Gly Phe Phe Arg Thr Asp Tyr<br>370                   375                 380         385 | 2591 |

```
tac cca aat cgg tgg cag aag atc ctg tcg ttt ggc gga cgt gtc cgc    2639
Tyr Pro Asn Arg Trp Gln Lys Ile Leu Ser Phe Gly Gly Arg Val Arg
            390                 395                 400 atg agc act tcc ctg ttg ttg ggt gcg ctg ctc ttg ctg tca cta ttt    2687
Met Ser Thr Ser Leu Leu Leu Gly Ala Leu Leu Leu Leu Ser Leu Phe
            405                 410                 415 aag ggg ctc ttc ctg ttt tagagtgcat tgatcttatg gaccaactgc           2735
Lys Gly Leu Phe Leu Phe
            420 cctgaatgga taaggcaccg cagaatgtag tggttcaaat tacggaaacc tagagcaatc  2795 ccacgcaaat gctccaaccg tccgttgatc gcttcgaccg gaccgttgga gacaccaaca  2855 tcgaaatacg ccaacacatc accaagtcgt taaacaaac tacgacccaa ctgcgcgagt   2915 tccttattcg gccccttcaa cacccgaagc tgatcaataa tggtccgcat tttcttcttc  2975 gcttcacgct tattacccat ctgataacaa tcaataatcg cctgatacgc aagccacgca  3035 agctttaaca ccccgtagtc tttgtcatac gcccacaact gctccaagct ttcttgctga  3095 cgaggactca accacttgtg cgtggtcaac aaggtcttcc ggtttttata caacggatcc  3155 tggcttaaac cacgacgctg gtatttctcc cgctggaggc gttgccggca ggcggtgagc  3215 ttgtcaccag caagccgcac aacatggaat ggatccatca cgcgacgagc agaaggaatg  3275 agttctttac ttgctgtggc gtagccttgg aacccatcca tggacacgat ccgtatctga  3335 ttgcggaact gttcaccgcg ggaaccaagc caggaccgta agcatcagc actacgacct   3395 gggacgacat ctaataaccg ggcaggacac cgtgagtcat accgatgccc ggtcatatcg  3455 acaatcacgg tgacaaaccc atcaccatgc ttagccctat tatgtgacca cttatgctca  3515 tccaccccaa tgcatacac tccatcaaga tggtgaggat cgttatagac cagctcacgg   3575 cacatatcga gggctagttg gcaggttaaa tcccacccta gcccaagtgc tttcgcggtt  3635 gcgtgaacac tcatccggtc aatagcaagg cgttgcaaaa tccagcgggt gacccggtgg  3695 gtgaccttt taccgtggtc agcgcagctt agttctgctt ggaaatactt ttgcttacat   3755 gtcgggttgg tgcagcggta gcgaggtaga cggataaaca gtttggtggg aaacccgacg  3815 atgggtaaat caatgagcat ccggtgggtg tgatgacgaa acaccccagg ttgggagcat  3875 tctgggcagg tggaggtata gtcgagtgcg tctgcttcga tcagggtgta atcacctgca  3935 tcggaagcgc cggtgatggt gagtcctagt tccgcagtgc ggcagatggt gtcagcgatg  3995 atgttgccgg tagacttcat gggtagagcc ttttgttggt gtttggttag cttagatacc  4055 taaaccttaa ccctgacaaa aggctcgttt attttcgggt ctacaccgct agcccaggtt  4115 ctgtgatgta ccccaaaacc ggaagggcca tttaaggtca tgactgtgga accaagtgag  4175 aattggcaaa actccagtgg atggctgtca ccaagcactg ccacctcaac tgcggtgacc  4235 acctccgaaa cttccgcgcc agcaagcacg ccttcgatga cagtgcccac tacggtggag  4295 gagacccaa cgatggaatc tagcgtcgaa acgcagcagg aaacctcaac ccctgcaacc   4355 gcaacgcccc agcgagccga caccatcgaa ccgaccgagg aagccacgtc gcaggaggaa  4415 acgactgcat cgcagacgca gtctccagca gtggaagcac caaccgcggt ccaagaaaca  4475 gttgcgccga cgtccacccc ttaggacgct gattacagac gtgtcccatt tctttactac  4535 tattggaaat tatgagttca gacgcagaaa aggcatccgt ggagctttcc gaaaaatttc  4595 acccagaacg cacccatatt ttgggcgccg ttgttttgg cctgatctca ttattagtca   4655 tcggcgcagc cctcagtac ctgttttggc tgctcgcgct ccctgtcatc ttcggttact   4715 gggttctaaa atcatccacg atcgttgatg aacagggcat caccgcaaac tacgccttca  4775
```

```
agggcaaaaa ggttgtggcc tgggaagacc tcgcaggaat cggattcaag ggtgcccgca    4835
ctttcgctcg caccacctcc gatgcagaag tcaccctccc cggcgtcacc ttcaactccc    4895
ttccccgcct tgaagctgct tcccacggcc gcatccccga tgcgatc                  4942
```

<210> SEQ ID NO 8
<211> LENGTH: 423
<212> TYPE: PRT
<213> ORGANISM: Corynebacterium glutamicum

<400> SEQUENCE: 8

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
        275                 280                 285

Gly Thr Leu Ile Asp Ser Leu His Val Glu His Glu Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350
```

```
Leu Asp Ser Asp Val Leu Glu Gln Glu Leu Ser Ser Glu Glu Pro Glu
        355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
            405                 410                 415

Phe Lys Gly Leu Phe Leu Phe
            420

<210> SEQ ID NO 9
<211> LENGTH: 37
<212> TYPE: DNA
<213> ORGANISM: Artificial sequence
<220> FEATURE:
<223> OTHER INFORMATION: primer

<400> SEQUENCE: 9
cggggtacct ataaagttcg attccttaaa ggggttc                              37

<210> SEQ ID NO 10
<211> LENGTH: 38
<212> TYPE: DNA
<213> ORGANISM: Artificial sequence
<220> FEATURE:
<223> OTHER INFORMATION: primer

<400> SEQUENCE: 10
cgcggatccg tgccaatgcc attagctgcg tcctcctg                             38

<210> SEQ ID NO 11
<211> LENGTH: 34
<212> TYPE: DNA
<213> ORGANISM: Artificial sequence
<220> FEATURE:
<223> OTHER INFORMATION: primer

<400> SEQUENCE: 11
ctagtctaga ttttcaacac gccgcgcaat atcc                                 34

<210> SEQ ID NO 12
<211> LENGTH: 41
<212> TYPE: DNA
<213> ORGANISM: Artificial sequence
<220> FEATURE:
<223> OTHER INFORMATION: primer

<400> SEQUENCE: 12
ctagtctaga gaattcgccc ttggcctttc atcggctaag c                         41

<210> SEQ ID NO 13
<211> LENGTH: 24
<212> TYPE: DNA
<213> ORGANISM: Artificial sequence
<220> FEATURE:
<223> OTHER INFORMATION: primer

<400> SEQUENCE: 13
aaattcctgt gaattagctg attt                                            24

<210> SEQ ID NO 14
<211> LENGTH: 48
<212> TYPE: DNA
```

<213> ORGANISM: Artificial sequence
<220> FEATURE:
<223> OTHER INFORMATION: primer

<400> SEQUENCE: 14
ggtaccaata acaggattag tcatagaggc gaaggctcct tgaatagg            48

<210> SEQ ID NO 15
<211> LENGTH: 34
<212> TYPE: DNA
<213> ORGANISM: Artificial sequence
<220> FEATURE:
<223> OTHER INFORMATION: primer

<400> SEQUENCE: 15
ctagtctaga gaattcgccc ttggcctttc atcg            34

<210> SEQ ID NO 16
<211> LENGTH: 48
<212> TYPE: DNA
<213> ORGANISM: Artificial sequence
<220> FEATURE:
<223> OTHER INFORMATION: primer

<400> SEQUENCE: 16
cctattcaag gagccttcgc ctctatgact aatcctgtta ttggtacc            48

<210> SEQ ID NO 17
<211> LENGTH: 44
<212> TYPE: DNA
<213> ORGANISM: Artificial sequence
<220> FEATURE:
<223> OTHER INFORMATION: primer

<400> SEQUENCE: 17
ctattctaga aaattcctgt gaattagctg atttagtact tttc            44

<210> SEQ ID NO 18
<211> LENGTH: 52
<212> TYPE: DNA
<213> ORGANISM: Artificial sequence
<220> FEATURE:
<223> OTHER INFORMATION: primer

<400> SEQUENCE: 18
ggtgatcacg ctatagttgc gccatgtaag aaaaggagct tgctttacga cg            52

<210> SEQ ID NO 19
<211> LENGTH: 52
<212> TYPE: DNA
<213> ORGANISM: Artificial sequence
<220> FEATURE:
<223> OTHER INFORMATION: primer

<400> SEQUENCE: 19
cgtcgtaaag caagctcctt ttcttacatg gcgcaactat agcgtgatca cc            52

<210> SEQ ID NO 20
<211> LENGTH: 30
<212> TYPE: DNA
<213> ORGANISM: Artificial sequence
<220> FEATURE:
<223> OTHER INFORMATION: primer

<400> SEQUENCE: 20
tggagcaaca cccatggtca ggtcgaggat            30

<210> SEQ ID NO 21
<211> LENGTH: 30
<212> TYPE: DNA
<213> ORGANISM: Artificial sequence
<220> FEATURE:
<223> OTHER INFORMATION: primer

<400> SEQUENCE: 21
agtatttgag ctaggcgaac tcgatgcaga                                    30

<210> SEQ ID NO 22
<211> LENGTH: 40
<212> TYPE: DNA
<213> ORGANISM: Artificial sequence
<220> FEATURE:
<223> OTHER INFORMATION: primer

<400> SEQUENCE: 22
ggtctctaga gtggaagata atgaacgcaa ggagaacgat                         40

<210> SEQ ID NO 23
<211> LENGTH: 40
<212> TYPE: DNA
<213> ORGANISM: Artificial sequence
<220> FEATURE:
<223> OTHER INFORMATION: primer

<400> SEQUENCE: 23
cagatctaga gtctgaaagt gaaggcatta gacgtgttgt                         40

<210> SEQ ID NO 24
<211> LENGTH: 40
<212> TYPE: DNA
<213> ORGANISM: Artificial sequence
<220> FEATURE:
<223> OTHER INFORMATION: primer

<400> SEQUENCE: 24
ggtctctaga ttccaaagtc tggcacacga ggtcctgaga                         40

<210> SEQ ID NO 25
<211> LENGTH: 40
<212> TYPE: DNA
<213> ORGANISM: Artificial sequence
<220> FEATURE:
<223> OTHER INFORMATION: primer

<400> SEQUENCE: 25
cagatctaga tcgccgaatg cccacagtcg cccgcgcagc                         40

<210> SEQ ID NO 26
<211> LENGTH: 41
<212> TYPE: DNA
<213> ORGANISM: Artificial sequence
<220> FEATURE:
<223> OTHER INFORMATION: primer

<400> SEQUENCE: 26
gtaaagtacc gctaaaaacg aggcaaaggg tgcttcgcaa c                       41

<210> SEQ ID NO 27
<211> LENGTH: 41
<212> TYPE: DNA
<213> ORGANISM: Artificial sequence
<220> FEATURE:
<223> OTHER INFORMATION: primer

```
<400> SEQUENCE: 27
gttgcgaagc acccttttgcc tcgttttttag cggtacttta c                    41

<210> SEQ ID NO 28
<211> LENGTH: 50
<212> TYPE: DNA
<213> ORGANISM: Artificial sequence
<220> FEATURE:
<223> OTHER INFORMATION: primer

<400> SEQUENCE: 28
gaaaattaca aaataaaacg aggcgagccg ggctgtacgc aaggcggacg             50

<210> SEQ ID NO 29
<211> LENGTH: 50
<212> TYPE: DNA
<213> ORGANISM: Artificial sequence
<220> FEATURE:
<223> OTHER INFORMATION: primer

<400> SEQUENCE: 29
cgtccgcctt gcgtacagcc cggctcgcct cgttttattt tgtaattttc             50

<210> SEQ ID NO 30
<211> LENGTH: 4394
<212> TYPE: DNA
<213> ORGANISM: Corynebacterium glutamicum
<220> FEATURE:
<221> NAME/KEY: CDS
<222> LOCATION: (443)..(4213)

<400> SEQUENCE: 30
```

| | |
|---|---|
| gtcgacaagc aaaatcgaag cggcagcacg ccgcgtcgga gccttaaacg ccatcgccgc | 60 |
| catccctgat ggtttcaatc atcaagtcgg tgaacgcggg cgcaacctgt catccggaca | 120 |
| gcgccaactg atcgcgctgg cgcgcgccga actcatcgag ccttccatca tgcttctcga | 180 |
| cgaagccacc tccaccctcg accccgccac cgaagccgtt atcctcaacg cctccgatcg | 240 |
| agtcactaag gacgcaccca gcatcatcgt cgcgcaccgc ttggcaaccg ctaaaagggc | 300 |
| cgaccgtatt cttgttgttg aacaaggacg tatcattgag gacggatctc acgacgcgtt | 360 |
| gttgtctgct aacggcacct acgcccgcat gtggcattta atggcctgac acgttatttt | 420 |

```
taggagaact gtcaacaaat ta atg cta caa ctg ggg ctt agg cat aat cag       472
                         Met Leu Gln Leu Gly Leu Arg His Asn Gln
                           1               5                  10 cca acg acc aac gtt aca gtg gat aaa ata aag ctc aat aaa ccc tca        520
Pro Thr Thr Asn Val Thr Val Asp Lys Ile Lys Leu Asn Lys Pro Ser
            15                  20                  25 aga agc aag gaa aag agg cga gta cct gcc gtg agc agc gct agt act        568
Arg Ser Lys Glu Lys Arg Arg Val Pro Ala Val Ser Ser Ala Ser Thr
        30                  35                  40 ttc ggc cag aat gcg tgg ctg gta gac gag atg ttc cag cag ttc cag        616
Phe Gly Gln Asn Ala Trp Leu Val Asp Glu Met Phe Gln Gln Phe Gln
    45                  50                  55 aag gac ccc aag tcc gtg gac aag gaa tgg aga gaa ctc ttt gag gcg        664
Lys Asp Pro Lys Ser Val Asp Lys Glu Trp Arg Glu Leu Phe Glu Ala
60                  65                  70 cag ggg gga cca aat gct acc ccc gct aca aca gaa gca cag cct tca        712
Gln Gly Gly Pro Asn Ala Thr Pro Ala Thr Thr Glu Ala Gln Pro Ser
            75                  80                  85                  90 gcg ccc aag gag tct gcg aaa cca gca cca aag gct gcc cct gca gcc        760
Ala Pro Lys Glu Ser Ala Lys Pro Ala Pro Lys Ala Ala Pro Ala Ala
                95                 100                 105
```

-continued

| | |
|---|---|
| aag gca gca ccg cgc gta gaa acc aag ccg gcc gcc aag acc gcc cct<br>Lys Ala Ala Pro Arg Val Glu Thr Lys Pro Ala Ala Lys Thr Ala Pro<br>110                       115                       120 | 808 |
| aag gcc aag gag tcc tca gtg cca cag caa cct aag ctt ccg gag cca<br>Lys Ala Lys Glu Ser Ser Val Pro Gln Gln Pro Lys Leu Pro Glu Pro<br>            125                     130                     135 | 856 |
| gga caa acc cca atc agg ggt att ttc aag tcc atc gcg aag aac atg<br>Gly Gln Thr Pro Ile Arg Gly Ile Phe Lys Ser Ile Ala Lys Asn Met<br>140                       145                       150 | 904 |
| gat atc tcc ctg gaa atc cca acc gca acc tcg gtt cgc gat atg cca<br>Asp Ile Ser Leu Glu Ile Pro Thr Ala Thr Ser Val Arg Asp Met Pro<br>155                       160                     165                     170 | 952 |
| gct cgc ctc atg ttc gaa aac cgc gcg atg gtc aac gat cag ctc aag<br>Ala Arg Leu Met Phe Glu Asn Arg Ala Met Val Asn Asp Gln Leu Lys<br>                     175                     180                     185 | 1000 |
| cgc acc cgc ggt ggc aag atc tcc ttc acc cac atc att ggc tac gcc<br>Arg Thr Arg Gly Gly Lys Ile Ser Phe Thr His Ile Ile Gly Tyr Ala<br>                 190                     195                     200 | 1048 |
| atg gtg aag gca gtc atg gct cac ccg gac atg aac aac tcc tac gac<br>Met Val Lys Ala Val Met Ala His Pro Asp Met Asn Asn Ser Tyr Asp<br>205                       210                       215 | 1096 |
| gtc atc gac ggc aag cca acc ctg atc gtg cct gag cac atc aac ctg<br>Val Ile Asp Gly Lys Pro Thr Leu Ile Val Pro Glu His Ile Asn Leu<br>220                       225                     230 | 1144 |
| ggc ctt gcc atc gac ctt cct cag aag gac ggc tcc cgc gca ctt gtc<br>Gly Leu Ala Ile Asp Leu Pro Gln Lys Asp Gly Ser Arg Ala Leu Val<br>235                       240                     245                     250 | 1192 |
| gta gca gcc atc aag gaa acc gag aag atg aac ttc tcc gag ttc ctc<br>Val Ala Ala Ile Lys Glu Thr Glu Lys Met Asn Phe Ser Glu Phe Leu<br>                     255                     260                     265 | 1240 |
| gca gca tac gaa gac atc gtg aca cgc tcc cgc aag ggc aag ctc acc<br>Ala Ala Tyr Glu Asp Ile Val Thr Arg Ser Arg Lys Gly Lys Leu Thr<br>                 270                     275                     280 | 1288 |
| atg gat gac tac cag ggc gtt acc gtt tcc ttg acc aac cca ggt ggc<br>Met Asp Asp Tyr Gln Gly Val Thr Val Ser Leu Thr Asn Pro Gly Gly<br>             285                     290                     295 | 1336 |
| atc ggt acc cgc cac tct gtc cca cgt ctg acc aag ggc cag ggc acc<br>Ile Gly Thr Arg His Ser Val Pro Arg Leu Thr Lys Gly Gln Gly Thr<br>300                       305                     310 | 1384 |
| atc atc ggt gtc ggt tcc atg gat tac cca gca gag ttc cag ggc gct<br>Ile Ile Gly Val Gly Ser Met Asp Tyr Pro Ala Glu Phe Gln Gly Ala<br>315                       320                     325                     330 | 1432 |
| tcc gaa gac cgc ctt gca gag ctc ggc gtt gga aag ctt gtc acc atc<br>Ser Glu Asp Arg Leu Ala Glu Leu Gly Val Gly Lys Leu Val Thr Ile<br>                     335                     340                     345 | 1480 |
| acc tcc acc tac gat cac cgc gtg atc cag ggt gct gtg tcc ggt gaa<br>Thr Ser Thr Tyr Asp His Arg Val Ile Gln Gly Ala Val Ser Gly Glu<br>                 350                     355                     360 | 1528 |
| ttc ctg cgt acc atg tct cgc ctg ctc acc gat gat tcc ttc tgg gat<br>Phe Leu Arg Thr Met Ser Arg Leu Leu Thr Asp Asp Ser Phe Trp Asp<br>             365                     370                     375 | 1576 |
| gag atc ttc gac gca atg aac gtt cct tac acc cca atg cgt tgg gca<br>Glu Ile Phe Asp Ala Met Asn Val Pro Tyr Thr Pro Met Arg Trp Ala<br>380                       385                     390 | 1624 |
| cag gac gtt cca aac acc ggt gtt gat aag aac acc cgc gtc atg cag<br>Gln Asp Val Pro Asn Thr Gly Val Asp Lys Asn Thr Arg Val Met Gln<br>395                       400                     405                     410 | 1672 |
| ctc att gag gca tac cgc tcc cgt gga cac ctc atc gct gac acc aac<br>Leu Ile Glu Ala Tyr Arg Ser Arg Gly His Leu Ile Ala Asp Thr Asn<br>                     415                     420                     425 | 1720 |

-continued

| | | |
|---|---|---|
| cca ctt tca tgg gtt cag cct ggc atg cca gtt cca gac cac cgc gac<br>Pro Leu Ser Trp Val Gln Pro Gly Met Pro Val Pro Asp His Arg Asp<br>430 435 440 | | 1768 |
| ctc gac atc gag acc cac agc ctg acc atc tgg gat ctg gac cgt acc<br>Leu Asp Ile Glu Thr His Ser Leu Thr Ile Trp Asp Leu Asp Arg Thr<br>445 450 455 | | 1816 |
| ttc agc gtc ggt ggc ttc ggc ggc aag gag acc atg acc ctg cgc gag<br>Phe Ser Val Gly Gly Phe Gly Gly Lys Glu Thr Met Thr Leu Arg Glu<br>460 465 470 | | 1864 |
| gta ctg tcc cgc ctg cgc gct gcc tac acc ttg aag gtc ggc tcc gaa<br>Val Leu Ser Arg Leu Arg Ala Ala Tyr Thr Leu Lys Val Gly Ser Glu<br>475 480 485 490 | | 1912 |
| tac acc cac atc ctg gac cgc gac gag cgc acc tgg ctg cag gac cgc<br>Tyr Thr His Ile Leu Asp Arg Asp Glu Arg Thr Trp Leu Gln Asp Arg<br>495 500 505 | | 1960 |
| ctc gaa gcc gga atg cca aag cca acc cag gca gag cag aag tac atc<br>Leu Glu Ala Gly Met Pro Lys Pro Thr Gln Ala Glu Gln Lys Tyr Ile<br>510 515 520 | | 2008 |
| ctg cag aag ctg aac gcc gca gag gct ttc gag aac ttc ctg cag acc<br>Leu Gln Lys Leu Asn Ala Ala Glu Ala Phe Glu Asn Phe Leu Gln Thr<br>525 530 535 | | 2056 |
| aag tac gtc ggc cag aag cgc ttc tcc ctc gaa ggt gca gaa gct ctc<br>Lys Tyr Val Gly Gln Lys Arg Phe Ser Leu Glu Gly Ala Glu Ala Leu<br>540 545 550 | | 2104 |
| atc cca ctg atg gac tcc gcc atc gac acc gcc gca ggc cag ggc ctc<br>Ile Pro Leu Met Asp Ser Ala Ile Asp Thr Ala Ala Gly Gln Gly Leu<br>555 560 565 570 | | 2152 |
| gac gaa gtt gtc atc ggt atg cca cac cgt ggt cgc ctc aac gtg ctg<br>Asp Glu Val Val Ile Gly Met Pro His Arg Gly Arg Leu Asn Val Leu<br>575 580 585 | | 2200 |
| ttc aac atc gtg ggc aag cca ctg gca tcc atc ttc aac gag ttt gaa<br>Phe Asn Ile Val Gly Lys Pro Leu Ala Ser Ile Phe Asn Glu Phe Glu<br>590 595 600 | | 2248 |
| ggc caa atg gag cag ggc cag atc ggt ggc tcc ggt gac gtg aag tac<br>Gly Gln Met Glu Gln Gly Gln Ile Gly Gly Ser Gly Asp Val Lys Tyr<br>605 610 615 | | 2296 |
| cac ctc ggt tcc gaa ggc cag cac ctg cag atg ttc ggc gac ggc gag<br>His Leu Gly Ser Glu Gly Gln His Leu Gln Met Phe Gly Asp Gly Glu<br>620 625 630 | | 2344 |
| atc aag gtc tcc ctg act gct aac ccg tcc cac ctg gaa gct gtt aac<br>Ile Lys Val Ser Leu Thr Ala Asn Pro Ser His Leu Glu Ala Val Asn<br>635 640 645 650 | | 2392 |
| cca gtg atg gaa ggt atc gtc cgc gca aag cag gac tac ctg gac aag<br>Pro Val Met Glu Gly Ile Val Arg Ala Lys Gln Asp Tyr Leu Asp Lys<br>655 660 665 | | 2440 |
| ggc gta gac ggc aag act gtt gtg cca ctg ctg ctc cac ggt gac gct<br>Gly Val Asp Gly Lys Thr Val Val Pro Leu Leu Leu His Gly Asp Ala<br>670 675 680 | | 2488 |
| gca ttc gca ggc ctg ggc atc gtg cca gaa acc atc aac ctg gct aag<br>Ala Phe Ala Gly Leu Gly Ile Val Pro Glu Thr Ile Asn Leu Ala Lys<br>685 690 695 | | 2536 |
| ctg cgt ggc tac gac gtc gga ggc acc atc cac atc gtg gtg aac aac<br>Leu Arg Gly Tyr Asp Val Gly Gly Thr Ile His Ile Val Val Asn Asn<br>700 705 710 | | 2584 |
| cag atc ggc ttc acc acc acc cca gac tcc agc cgc tcc atg cac tac<br>Gln Ile Gly Phe Thr Thr Thr Pro Asp Ser Ser Arg Ser Met His Tyr<br>715 720 725 730 | | 2632 |
| gca acc gac tac gcc aag gca ttc ggc tgc cca gtc ttc cac gtc aat<br>Ala Thr Asp Tyr Ala Lys Ala Phe Gly Cys Pro Val Phe His Val Asn<br>735 740 745 | | 2680 |

| | |
|---|---|
| ggt gat gac cca gag gca gtt gtc tgg gtt ggc cag ctg gca acc gag<br>Gly Asp Asp Pro Glu Ala Val Val Trp Val Gly Gln Leu Ala Thr Glu<br>750                        755                  760 | 2728 |
| tac cgt cgt cgc ttc ggc aag gac gtc ttc atc gac ctc gtt tgc tac<br>Tyr Arg Arg Arg Phe Gly Lys Asp Val Phe Ile Asp Leu Val Cys Tyr<br>     765                    770                     775 | 2776 |
| cgc ctc cgc ggc cac aac gaa gct gat gat cct tcc atg acc cag cca<br>Arg Leu Arg Gly His Asn Glu Ala Asp Asp Pro Ser Met Thr Gln Pro<br>780                        785                  790 | 2824 |
| aag atg tat gag ctc atc acc ggc cgc gag acc gtt cgt gct cag tac<br>Lys Met Tyr Glu Leu Ile Thr Gly Arg Glu Thr Val Arg Ala Gln Tyr<br>795                  800                  805                 810 | 2872 |
| acc gaa gac ctg ctc gga cgt gga gac ctc tcc aac gaa gat gca gaa<br>Thr Glu Asp Leu Leu Gly Arg Gly Asp Leu Ser Asn Glu Asp Ala Glu<br>              815                  820                  825 | 2920 |
| gca gtc gtc cgc gac ttc cac gac cag atg gaa tct gtg ttc aac gaa<br>Ala Val Val Arg Asp Phe His Asp Gln Met Glu Ser Val Phe Asn Glu<br>         830                    835                    840 | 2968 |
| gtc aag gaa ggc ggc aag aag cag gct gag gca cag acc ggc atc acc<br>Val Lys Glu Gly Gly Lys Lys Gln Ala Glu Ala Gln Thr Gly Ile Thr<br>845                        850                  855 | 3016 |
| ggc tcc cag aag ctt cca cac ggc ctt gag acc aac atc tcc cgt gaa<br>Gly Ser Gln Lys Leu Pro His Gly Leu Glu Thr Asn Ile Ser Arg Glu<br>860                        865                  870 | 3064 |
| gag ctc ctg gaa ctg gga cag gct ttc gcc aac acc cca gaa ggc ttc<br>Glu Leu Leu Glu Leu Gly Gln Ala Phe Ala Asn Thr Pro Glu Gly Phe<br>875                  880                  885                 890 | 3112 |
| aac tac cac cca cgt gtg gct cca gtt gct aag aag cgc gtc tcc tct<br>Asn Tyr His Pro Arg Val Ala Pro Val Ala Lys Lys Arg Val Ser Ser<br>              895                  900                  905 | 3160 |
| gtc acc gaa ggt ggc atc gac tgg gca tgg ggc gag ctc ctc gcc ttc<br>Val Thr Glu Gly Gly Ile Asp Trp Ala Trp Gly Glu Leu Leu Ala Phe<br>         910                    915                  920 | 3208 |
| ggt tcc ctg gct aac tcc ggc cgc ttg gtt cgc ctt gca ggt gaa gat<br>Gly Ser Leu Ala Asn Ser Gly Arg Leu Val Arg Leu Ala Gly Glu Asp<br>925                        930                  935 | 3256 |
| tcc cgc cgc ggt acc ttc acc cag cgc cac gca gtt gcc atc gac cca<br>Ser Arg Arg Gly Thr Phe Thr Gln Arg His Ala Val Ala Ile Asp Pro<br>940                        945                  950 | 3304 |
| gcg acc gct gaa gag ttc aac cca ctc cac gag ctt gca cag tcc aag<br>Ala Thr Ala Glu Glu Phe Asn Pro Leu His Glu Leu Ala Gln Ser Lys<br>955                  960                  965                 970 | 3352 |
| ggc aac aac ggt aag ttc ctg gtc tac aac tcc gca ctg acc gag tac<br>Gly Asn Asn Gly Lys Phe Leu Val Tyr Asn Ser Ala Leu Thr Glu Tyr<br>              975                  980                  985 | 3400 |
| gca ggc atg ggc ttc gag tac ggc tac tcc gta gga aac gaa  gac tcc<br>Ala Gly Met Gly Phe Glu Tyr Gly Tyr Ser Val Gly Asn Glu  Asp Ser<br>990                        995                    1000 | 3448 |
| gtc gtt gca  tgg gaa gca cag ttc    ggc gac ttc gcc aac  ggc gct<br>Val Val Ala  Trp Glu Ala Gln Phe    Gly Asp Phe Ala Asn  Gly Ala<br>         1005                          1010                        1015 | 3493 |
| cag acc atc  atc gat gag tac gtc    tcc tca ggc gaa gct  aag tgg<br>Gln Thr Ile  Ile Asp Glu Tyr Val    Ser Ser Gly Glu Ala  Lys Trp<br>         1020                          1025                        1030 | 3538 |
| ggc cag acc  tcc aag ctg atc ctt    ctg ctg cct cac ggc  tac gaa<br>Gly Gln Thr  Ser Lys Leu Ile Leu    Leu Leu Pro His Gly  Tyr Glu<br>         1035                          1040                        1045 | 3583 |
| ggc cag ggc  cca gac cac tct tcc    gca cgt atc gag cgc  ttc ctg<br>Gly Gln Gly  Pro Asp His Ser Ser    Ala Arg Ile Glu Arg  Phe Leu<br>         1050                          1055                        1060 | 3628 |

```
cag ctg tgc gct gag ggt tcc atg act gtt gct cag cca tcc acc      3673
Gln Leu Cys Ala Glu Gly Ser Met Thr Val Ala Gln Pro Ser Thr
        1065                1070                1075 cca gca aac cac ttc cac ctg ctg cgt cgt cac gct ctg tcc gac      3718
Pro Ala Asn His Phe His Leu Leu Arg Arg His Ala Leu Ser Asp
    1080                1085                1090 ctg aag cgt cca ctg gtt atc ttc acc ccg aag tcc atg ctg cgt      3763
Leu Lys Arg Pro Leu Val Ile Phe Thr Pro Lys Ser Met Leu Arg
1095                1100                1105 aac aag gct gct gcc tcc gca cca gaa gac ttc act gag gtc acc      3808
Asn Lys Ala Ala Ala Ser Ala Pro Glu Asp Phe Thr Glu Val Thr
            1110                1115                1120 aag ttc caa tcc gtg atc gac gat cca aac gtt gca gat gca gcc      3853
Lys Phe Gln Ser Val Ile Asp Asp Pro Asn Val Ala Asp Ala Ala
        1125                1130                1135 aag gtg aag aag gtc atg ctg gtc tcc ggc aag ctg tac tac gaa      3898
Lys Val Lys Lys Val Met Leu Val Ser Gly Lys Leu Tyr Tyr Glu
    1140                1145                1150 ttg gca aag cgc aag gag aag gac gga cgc gac gac atc gcg atc      3943
Leu Ala Lys Arg Lys Glu Lys Asp Gly Arg Asp Asp Ile Ala Ile
1155                1160                1165 gtt cgt atc gaa atg ctc cac cca att ccg ttc aac cgc atc tcc      3988
Val Arg Ile Glu Met Leu His Pro Ile Pro Phe Asn Arg Ile Ser
            1170                1175                1180 gag gct ctt gcc ggc tac cct aac gct gag gaa gtc ctc ttc gtt      4033
Glu Ala Leu Ala Gly Tyr Pro Asn Ala Glu Glu Val Leu Phe Val
        1185                1190                1195 cag gat gag cca gca aac cag ggc cca tgg ccg ttc tac cag gag      4078
Gln Asp Glu Pro Ala Asn Gln Gly Pro Trp Pro Phe Tyr Gln Glu
    1200                1205                1210 cac ctc cca gag ctg atc ccg aac atg cca aag atg cgc cgc gtt      4123
His Leu Pro Glu Leu Ile Pro Asn Met Pro Lys Met Arg Arg Val
1215                1220                1225 tcc cgc cgc gct cag tcc tcc acc gca act ggt gtt gct aag gtg      4168
Ser Arg Arg Ala Gln Ser Ser Thr Ala Thr Gly Val Ala Lys Val
            1230                1235                1240 cac cag ctg gag gag aag cag ctt atc gac gag gct ttc gag gct      4213
His Gln Leu Glu Glu Lys Gln Leu Ile Asp Glu Ala Phe Glu Ala
        1245                1250                1255 taagtcttta tagtcctgca ctagcctaga gggccttatg cagtgtgaat cacacagcat   4273
aaggcccttt tgctgccgt ggttgcctaa ggtggaaggc atgaaacgaa tctgtgcggt    4333
cacgatctct tcagtacttt tgctaagtgg ctgctcctcc acttccacca cgcagctcga   4393
g                                                                  4394

<210> SEQ ID NO 31
<211> LENGTH: 1257
<212> TYPE: PRT
<213> ORGANISM: Corynebacterium glutamicum

<400> SEQUENCE: 31

Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60
```

```
Asp Lys Glu Trp Arg Glu Leu Phe Glu Ala Gln Gly Gly Pro Asn Ala
 65                  70                  75                  80

Thr Pro Ala Thr Thr Glu Ala Gln Pro Ser Ala Pro Lys Glu Ser Ala
                 85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
        195                 200                 205

Ala His Pro Asp Met Asn Asn Ser Tyr Asp Val Ile Asp Gly Lys Pro
    210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
            260                 265                 270

Val Thr Arg Ser Arg Lys Gly Lys Leu Thr Met Asp Asp Tyr Gln Gly
        275                 280                 285

Val Thr Val Ser Leu Thr Asn Pro Gly Gly Ile Gly Thr Arg His Ser
    290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
            340                 345                 350

Arg Val Ile Gln Gly Ala Val Ser Gly Glu Phe Leu Arg Thr Met Ser
        355                 360                 365

Arg Leu Leu Thr Asp Asp Ser Phe Trp Asp Glu Ile Phe Asp Ala Met
    370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
            420                 425                 430

Pro Gly Met Pro Val Pro Asp His Arg Asp Leu Asp Ile Glu Thr His
        435                 440                 445

Ser Leu Thr Ile Trp Asp Leu Asp Arg Thr Phe Ser Val Gly Gly Phe
    450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
```

-continued

```
                485                 490                 495
Arg Asp Glu Arg Thr Trp Leu Gln Asp Arg Leu Glu Ala Gly Met Pro
            500                 505                 510
Lys Pro Thr Gln Ala Glu Gln Lys Tyr Ile Leu Gln Lys Leu Asn Ala
        515                 520                 525
Ala Glu Ala Phe Glu Asn Phe Leu Gln Thr Lys Tyr Val Gly Gln Lys
    530                 535                 540
Arg Phe Ser Leu Glu Gly Ala Glu Ala Leu Ile Pro Leu Met Asp Ser
545                 550                 555                 560
Ala Ile Asp Thr Ala Ala Gly Gln Gly Leu Asp Glu Val Val Ile Gly
                565                 570                 575
Met Pro His Arg Gly Arg Leu Asn Val Leu Phe Asn Ile Val Gly Lys
            580                 585                 590
Pro Leu Ala Ser Ile Phe Asn Glu Phe Glu Gly Gln Met Glu Gln Gly
        595                 600                 605
Gln Ile Gly Gly Ser Gly Asp Val Lys Tyr His Leu Gly Ser Glu Gly
    610                 615                 620
Gln His Leu Gln Met Phe Gly Asp Gly Glu Ile Lys Val Ser Leu Thr
625                 630                 635                 640
Ala Asn Pro Ser His Leu Glu Ala Val Asn Pro Val Met Glu Gly Ile
                645                 650                 655
Val Arg Ala Lys Gln Asp Tyr Leu Asp Lys Gly Val Asp Gly Lys Thr
            660                 665                 670
Val Val Pro Leu Leu Leu His Gly Asp Ala Ala Phe Ala Gly Leu Gly
        675                 680                 685
Ile Val Pro Glu Thr Ile Asn Leu Ala Lys Leu Arg Gly Tyr Asp Val
    690                 695                 700
Gly Gly Thr Ile His Ile Val Val Asn Asn Gln Ile Gly Phe Thr Thr
705                 710                 715                 720
Thr Pro Asp Ser Ser Arg Ser Met His Tyr Ala Thr Asp Tyr Ala Lys
                725                 730                 735
Ala Phe Gly Cys Pro Val Phe His Val Asn Gly Asp Asp Pro Glu Ala
            740                 745                 750
Val Val Trp Val Gly Gln Leu Ala Thr Glu Tyr Arg Arg Arg Phe Gly
        755                 760                 765
Lys Asp Val Phe Ile Asp Leu Val Cys Tyr Arg Leu Arg Gly His Asn
    770                 775                 780
Glu Ala Asp Asp Pro Ser Met Thr Gln Pro Lys Met Tyr Glu Leu Ile
785                 790                 795                 800
Thr Gly Arg Glu Thr Val Arg Ala Gln Tyr Thr Glu Asp Leu Leu Gly
                805                 810                 815
Arg Gly Asp Leu Ser Asn Glu Asp Ala Glu Ala Val Val Arg Asp Phe
            820                 825                 830
His Asp Gln Met Glu Ser Val Phe Asn Glu Val Lys Glu Gly Gly Lys
        835                 840                 845
Lys Gln Ala Glu Ala Gln Thr Gly Ile Thr Gly Ser Gln Lys Leu Pro
    850                 855                 860
His Gly Leu Glu Thr Asn Ile Ser Arg Glu Glu Leu Leu Glu Leu Gly
865                 870                 875                 880
Gln Ala Phe Ala Asn Thr Pro Glu Gly Phe Asn Tyr His Pro Arg Val
                885                 890                 895
Ala Pro Val Ala Lys Lys Arg Val Ser Ser Val Thr Glu Gly Gly Ile
            900                 905                 910
```

-continued

```
Asp Trp Ala Trp Gly Glu Leu Leu Ala Phe Gly Ser Leu Ala Asn Ser
        915                 920                 925

Gly Arg Leu Val Arg Leu Ala Gly Glu Asp Ser Arg Gly Thr Phe
    930                 935                 940

Thr Gln Arg His Ala Val Ala Ile Asp Pro Ala Thr Ala Glu Glu Phe
945                 950                 955                 960

Asn Pro Leu His Glu Leu Ala Gln Ser Lys Gly Asn Asn Gly Lys Phe
            965                 970                 975

Leu Val Tyr Asn Ser Ala Leu Thr Glu Tyr Ala Gly Met Gly Phe Glu
        980                 985                 990

Tyr Gly Tyr Ser Val Gly Asn Glu Asp Ser Val Val Ala Trp Glu Ala
        995                 1000                1005

Gln Phe Gly Asp Phe Ala Asn Gly Ala Gln Thr Ile Ile Asp Glu
    1010                1015                1020

Tyr Val Ser Ser Gly Glu Ala Lys Trp Gly Gln Thr Ser Lys Leu
    1025                1030                1035

Ile Leu Leu Leu Pro His Gly Tyr Glu Gly Gln Gly Pro Asp His
    1040                1045                1050

Ser Ser Ala Arg Ile Glu Arg Phe Leu Gln Leu Cys Ala Glu Gly
    1055                1060                1065

Ser Met Thr Val Ala Gln Pro Ser Thr Pro Ala Asn His Phe His
    1070                1075                1080

Leu Leu Arg Arg His Ala Leu Ser Asp Leu Lys Arg Pro Leu Val
    1085                1090                1095

Ile Phe Thr Pro Lys Ser Met Leu Arg Asn Lys Ala Ala Ala Ser
    1100                1105                1110

Ala Pro Glu Asp Phe Thr Glu Val Thr Lys Phe Gln Ser Val Ile
    1115                1120                1125

Asp Asp Pro Asn Val Ala Ala Ala Lys Val Lys Lys Val Met
    1130                1135                1140

Leu Val Ser Gly Lys Leu Tyr Tyr Glu Leu Ala Lys Arg Lys Glu
    1145                1150                1155

Lys Asp Gly Arg Asp Asp Ile Ala Ile Val Arg Ile Glu Met Leu
    1160                1165                1170

His Pro Ile Pro Phe Asn Arg Ile Ser Glu Ala Leu Ala Gly Tyr
    1175                1180                1185

Pro Asn Ala Glu Glu Val Leu Phe Val Gln Asp Glu Pro Ala Asn
    1190                1195                1200

Gln Gly Pro Trp Pro Phe Tyr Gln Glu His Leu Pro Glu Leu Ile
    1205                1210                1215

Pro Asn Met Pro Lys Met Arg Arg Val Ser Arg Arg Ala Gln Ser
    1220                1225                1230

Ser Thr Ala Thr Gly Val Ala Lys Val His Gln Leu Glu Glu Lys
    1235                1240                1245

Gln Leu Ile Asp Glu Ala Phe Glu Ala
    1250                1255

<210> SEQ ID NO 32
<211> LENGTH: 3481
<212> TYPE: DNA
<213> ORGANISM: Corynebacterium glutamicum
<220> FEATURE:
<221> NAME/KEY: CDS
<222> LOCATION: (1437)..(3035)

<400> SEQUENCE: 32
```

```
gatcttgccg atttcggcag gatcaatgtc ggcgtgaatg atcttggcat caggtgcgaa      60
agtgtcaacg tcaccggtga cgcggtcatc aaagcgggag ccgatagcaa tcagcaggtc     120
gctgcgctgc agtgcaccaa cagcggacac agtgccatgc atgcctggca tacccatgtg     180
cagctcgtgg gactctggga aggttcccag cgccatcaat gtggtgacaa ctggaatgcc     240
ggtgtgctca gcgaacgcac gaagctcttc gtgggcatca gccttgataa cgccgccgcc     300
aacgtaaagg acaggcttct tagactcacc gatcagtttg acagcctgct caatctgtcg     360
agcatgcggt gttgaaactg gcggtagcc tggcaggtcg atctttggtg ccagacgaa       420 atccaattca gcgttctgaa catccttggg gatatccact agaacaggac cagggcgacc    480
agtaatcgcg aggtggaatg cctcagccaa tgcctgtgga atgtcgttgg ggttggtgac    540
catgaagttg tgcttggtca ctggcatggt gatgccgcgg atatcggctt cctggaaagc    600
atcggtaccc agcaggctac ttccgacctg ccggtgatg gcaaccatgg gaacggagtc    660
caagtttgca tcagcgattg gggtaaccaa gttggttgcg cctgggccag aggttgcaat    720
gcagacgcca acgcgtccag taacctgcgc gtagccggtt gctgcgtggc ctgcgccctg    780
ctcgtggcgc actaggacgt ggcgcacctt tgtggaggaa tagagcgggt catacaccgg    840
tagcaccgca ccaccaggaa taccgaacac gatgtcggcg ttaagctcct cgagcgatcg    900
aacaattgcc tgtgcacctg tcatccgctc aggggcggcg gatcgaccac ggcttgcaac    960
cgtggcggga gtgggctgtt gagaagctgc cacattcacg actttctggc tcctttacta   1020
aataaggatt tcacaggac ccgtccaagc caagccgatt tcaactcagc ctaaagacaa    1080
agccctcatt taaaattgtt ccgacgcgga tgcgtgtgca cgcagtgcga cagatgtctg    1140
ttgcaaagtt ggctacttgg gtcataacca acaagaaagc cctcgttcca acactgtggt   1200
gagtgttgtc gagggcgctt gacgagacga cttggaaggc cgttacggca ggcgccgcgc    1260
ggttactact acaagtcgaa taatggtcat ggtgtgtcat gctacacaca tcgagtttcc   1320
aattccacaa cgcacgaaaa ttcccacccc caaaactccc ccacttcggt taaggaatca    1380
ggattctcac aaagttcagg caggctcccg ctactttca gcgctaatct tggctc atg     1439
                                                                   Met
                                                                    1 att tta ggc gta ccc att caa tat ttg ctc tat tca ttg tgg aat tgg      1487
Ile Leu Gly Val Pro Ile Gln Tyr Leu Leu Tyr Ser Leu Trp Asn Trp
         5                  10                  15 att gtc gat acc ggt ttt gat gta gca att atc ctg gtc ttg gcg ttt      1535
Ile Val Asp Thr Gly Phe Asp Val Ala Ile Ile Leu Val Leu Ala Phe
         20                  25                  30 ttg att cca cgt atc ggc cga ctg gcc atg cgt att atc aag cag cga      1583
Leu Ile Pro Arg Ile Gly Arg Leu Ala Met Arg Ile Ile Lys Gln Arg
         35                  40                  45 gtg gag tct gca gcc gat gcg gac acc act aag aac cag ctc gcg ttc      1631
Val Glu Ser Ala Ala Asp Ala Asp Thr Thr Lys Asn Gln Leu Ala Phe
50                  55                  60                  65 gct ggc gtt ggc gtt tat atc gcg caa att gtg gcg ttt ttc atg ctt      1679
Ala Gly Val Gly Val Tyr Ile Ala Gln Ile Val Ala Phe Phe Met Leu
                 70                  75                  80 gcc gtc tcc gcg atg cag gct ttt ggt ttc tct ctc gcg ggc gct gcg      1727
Ala Val Ser Ala Met Gln Ala Phe Gly Phe Ser Leu Ala Gly Ala Ala
                 85                  90                  95 att ccg gca acc att gcg tca gct gcc att ggt ctt ggt gcg cag tcg      1775
Ile Pro Ala Thr Ile Ala Ser Ala Ala Ile Gly Leu Gly Ala Gln Ser
             100                 105                 110 att gtt gcg gac ttc ttg gcc gga ttt ttc atc ctg acg gaa aag caa      1823
Ile Val Ala Asp Phe Leu Ala Gly Phe Phe Ile Leu Thr Glu Lys Gln
```

-continued

| | | |
|---|---|---|
| ttc ggc gtg ggt gac tgg gtg cgc ttt gag ggc aac ggc atc gtt gtt<br>Phe Gly Val Gly Asp Trp Val Arg Phe Glu Gly Asn Gly Ile Val Val<br>130                         135                       140                       145 | 1871 |
| gaa ggc acc gtc att gag atc acc atg cgc gcg acc aaa att cgc acg<br>Glu Gly Thr Val Ile Glu Ile Thr Met Arg Ala Thr Lys Ile Arg Thr<br>                     150                     155                     160 | 1919 |
| att gca caa gag acc gtg atc atc ccg aac tcc acg gcg aaa gtg tgc<br>Ile Ala Gln Glu Thr Val Ile Ile Pro Asn Ser Thr Ala Lys Val Cys<br>165                       170                     175 | 1967 |
| atc aac aat tct aat aac tgg tcg cgt gcg gtt gtc gtt att ccg atc<br>Ile Asn Asn Ser Asn Asn Trp Ser Arg Ala Val Val Val Ile Pro Ile<br>         180                     185                     190 | 2015 |
| ccc atg ttg ggt tct gaa aac atc aca gat gtc atc gcg cgc tct gaa<br>Pro Met Leu Gly Ser Glu Asn Ile Thr Asp Val Ile Ala Arg Ser Glu<br>    195                     200                     205 | 2063 |
| gct gcg act cgt cgc gca ctt ggc cag gag aaa atc gca ccg gaa atc<br>Ala Ala Thr Arg Arg Ala Leu Gly Gln Glu Lys Ile Ala Pro Glu Ile<br>210                       215                     220                   225 | 2111 |
| ctc ggt gaa ctc gat gtg cac cca gcc acg gaa gtc aca ccg cca acg<br>Leu Gly Glu Leu Asp Val His Pro Ala Thr Glu Val Thr Pro Pro Thr<br>                   230                     235                     240 | 2159 |
| gtg gtc ggc atg ccg tgg atg gtc acc atg cgt ttc ctc gtg caa gtc<br>Val Val Gly Met Pro Trp Met Val Thr Met Arg Phe Leu Val Gln Val<br>         245                     250                     255 | 2207 |
| acc gcc ggc aat caa tgg ctg gtc gaa cgc gcc atc cgc aca gaa atc<br>Thr Ala Gly Asn Gln Trp Leu Val Glu Arg Ala Ile Arg Thr Glu Ile<br>    260                     265                     270 | 2255 |
| atc aac gaa ttc tgg gaa gaa tac ggc agc gca acc act aca tcg gga<br>Ile Asn Glu Phe Trp Glu Glu Tyr Gly Ser Ala Thr Thr Thr Ser Gly<br>275                       280                     285 | 2303 |
| acc ctc att gat tcc tta cac gtt gag cat gaa gag cca aag acc tcg<br>Thr Leu Ile Asp Ser Leu His Val Glu His Glu Glu Pro Lys Thr Ser<br>290                       295                     300                   305 | 2351 |
| ctt atc gac gcc tcc ccc cag gct ctt aag gaa ccg aag ccg gag gct<br>Leu Ile Asp Ala Ser Pro Gln Ala Leu Lys Glu Pro Lys Pro Glu Ala<br>                     310                     315                     320 | 2399 |
| gcg gcg acg gtt gca tcg cta gct gca tcg tct aac gac gat gca gac<br>Ala Ala Thr Val Ala Ser Leu Ala Ala Ser Ser Asn Asp Asp Ala Asp<br>         325                     330                     335 | 2447 |
| aat gca gac gcc tcg gcg atc aat gca ggc aat cca gag aag gaa ctt<br>Asn Ala Asp Ala Ser Ala Ile Asn Ala Gly Asn Pro Glu Lys Glu Leu<br>    340                     345                     350 | 2495 |
| gat tcc gat gtg ctg gaa caa gaa ctc tcc agc gaa gaa ccg gaa gaa<br>Asp Ser Asp Val Leu Glu Gln Glu Leu Ser Ser Glu Glu Pro Glu Glu<br>355                       360                     365 | 2543 |
| aca gca aaa cca gat cac tct ctc cga ggc ttc ttc cgc act gat tac<br>Thr Ala Lys Pro Asp His Ser Leu Arg Gly Phe Phe Arg Thr Asp Tyr<br>370                       375                     380                   385 | 2591 |
| tac cca aat cgg tgg cag aag atc ctg tcg ttt ggc gga cgt gtc cgc<br>Tyr Pro Asn Arg Trp Gln Lys Ile Leu Ser Phe Gly Gly Arg Val Arg<br>                   390                     395                   400 | 2639 |
| atg agc act tcc ctg ttg ttg ggt gcg ctg ctc ttg ctg tca cta ttt<br>Met Ser Thr Ser Leu Leu Leu Gly Ala Leu Leu Leu Leu Ser Leu Phe<br>         405                     410                     415 | 2687 |
| aag gtc atg act gtg gaa cca agt gag aat tgg caa aac tcc agt gga<br>Lys Val Met Thr Val Glu Pro Ser Glu Asn Trp Gln Asn Ser Ser Gly<br>    420                     425                     430 | 2735 |
| tgg ctg tca cca agc act gcc acc tca act gcg gtg acc acc tcc gaa<br>Trp Leu Ser Pro Ser Thr Ala Thr Ser Thr Ala Val Thr Thr Ser Glu | 2783 |

-continued

```
                   435                 440                 445
act tcc gcg cca gca agc acg cct tcg atg aca gtg ccc act acg gtg        2831
Thr Ser Ala Pro Ala Ser Thr Pro Ser Met Thr Val Pro Thr Thr Val
450                 455                 460                 465 gag gag acc cca acg atg gaa tct agc gtc gaa acg cag cag gaa acc        2879
Glu Glu Thr Pro Thr Met Glu Ser Ser Val Glu Thr Gln Gln Glu Thr
                470                 475                 480 tca acc cct gca acc gca acg ccc cag cga gcc gac acc atc gaa ccg        2927
Ser Thr Pro Ala Thr Ala Thr Pro Gln Arg Ala Asp Thr Ile Glu Pro
            485                 490                 495 acc gag gaa gcc acg tcg cag gag gaa acg act gca tcg cag acg cag        2975
Thr Glu Glu Ala Thr Ser Gln Glu Glu Thr Thr Ala Ser Gln Thr Gln
        500                 505                 510 tct cca gca gtg gaa gca cca acc gcg gtc caa gaa aca gtt gcg ccg        3023
Ser Pro Ala Val Glu Ala Pro Thr Ala Val Gln Glu Thr Val Ala Pro
    515                 520                 525 acg tcc acc cct taggacgctg attacagacg tgtcccattt ctttactact            3075
Thr Ser Thr Pro
530 attggaaatt atgagttcag acgcagaaaa ggcatccgtg agctttccg aaaaatttca       3135 cccagaacgc acccatattt tgggcgccgt tgttttggc ctgatctcat tattagtcat       3195 cggcgcagcc cctcagtacc tgttttggct gctcgcgctc cctgtcatct tcggttactg      3255 ggttctaaaa tcatccacga tcgttgatga acagggcatc accgcaaact acgccttcaa      3315 gggcaaaaag gttgtggcct gggaagacct cgcaggaatc ggattcaagg gtgcccgcac      3375 tttcgctcgc accacctccg atgcagaagt caccctcccc ggcgtcacct tcaactccct      3435 tccccgcctt gaagctgctt cccacggccg catccccgat gcgatc                     3481
```

<210> SEQ ID NO 33
<211> LENGTH: 533
<212> TYPE: PRT
<213> ORGANISM: Corynebacterium glutamicum

<400> SEQUENCE: 33

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Met
65              70                  75                  80

Leu Ala Val Ser Ala Met Gln Ala Phe Gly Phe Ser Leu Ala Gly Ala
            85                  90                  95

Ala Ile Pro Ala Thr Ile Ala Ser Ala Ala Ile Gly Leu Gly Ala Gln
        100                 105                 110

Ser Ile Val Ala Asp Phe Leu Ala Gly Phe Phe Ile Leu Thr Glu Lys
    115                 120                 125

Gln Phe Gly Val Gly Asp Trp Val Arg Phe Glu Gly Asn Gly Ile Val
130             135                 140

Val Glu Gly Thr Val Ile Glu Ile Thr Met Arg Ala Thr Lys Ile Arg
145             150                 155                 160

Thr Ile Ala Gln Glu Thr Val Ile Ile Pro Asn Ser Thr Ala Lys Val
            165                 170                 175
```

```
Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Lys Ile Ala Pro Glu
210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
                260                 265                 270

Ile Ile Asn Glu Phe Trp Glu Tyr Gly Ser Ala Thr Thr Thr Ser
            275                 280                 285

Gly Thr Leu Ile Asp Ser Leu His Val Glu His Glu Pro Lys Thr
        290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Pro Glu
        355                 360                 365

Glu Thr Ala Lys Pro Asp His Ser Leu Arg Gly Phe Phe Arg Thr Asp
370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Ser Leu
                405                 410                 415

Phe Lys Val Met Thr Val Glu Pro Ser Glu Asn Trp Gln Asn Ser Ser
                420                 425                 430

Gly Trp Leu Ser Pro Ser Thr Ala Thr Ser Thr Ala Val Thr Thr Ser
            435                 440                 445

Glu Thr Ser Ala Pro Ala Ser Thr Pro Ser Met Thr Val Pro Thr Thr
        450                 455                 460

Val Glu Glu Thr Pro Thr Met Glu Ser Ser Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Glu Thr Val Ala
        515                 520                 525

Pro Thr Ser Thr Pro
    530

<210> SEQ ID NO 34
<211> LENGTH: 2644
<212> TYPE: DNA
<213> ORGANISM: Corynebacterium glutamicum
<220> FEATURE:
<221> NAME/KEY: CDS
<222> LOCATION: (1214)..(2641)

<400> SEQUENCE: 34
```

-continued

```
ttccaaagtc tggcacacga ggtcctgaga cttggaatca cgacgagcct gctccgaagc    60
tgcatcgtaa tcaatgtcct cagggttcac gatcacctcg atggtgtcgg aatgatcaag   120
ttccttcagt tccaacggag tgaacttcgc ctgagcaggt ccacgacgac caaaaacgtg   180
cacttcctta gcctgattct tagccaagct ctcatagaca ttgtcaggga tttcagtaac   240
tagcagctca tcgccagtct tcgccaaaat acgagcaacg tccaacgcca cgttaccgac   300
accaacaacc gctaccttct cagcagaaag atcccagttg cgttcaaagt tcggattgcc   360
atcatagaaa ccaacgaact cgccagcgcc ccacgaacct tccagatcag aacctggaac   420
ccgaagatcc tggtcgccag tagcgccagt ggagaacacg atcgcgtcat aaaactcacg   480
caactcctca acagtgatgt ccttgccgac ctcaatgttg cccaagaaac gcagctgctc   540
cttgtccatc acattgtgca gggacttcac gatgcccttg atgcgagggt gatcaggcgc   600
aacaccataa cggatcaaac cgaaaggcgc tggcatgcgt tcaaaaagat caatctgcac   660
gtccgtgtcg gatttcatca acaaatcaga cgcgtagatt cctgctggac ctgcaccgac   720
aacggcaaca cgcaaagggc gagacatata aagttcgatt ccttaagggg ttctaaaaa   780 atgtggagta tgtgagcggg gttccactag tagattcgac tcctatcggg gtgcgactgc   840
taatggtgcc ctgctatcaa ccctccatga tacgtggtaa gtgcagacta ataaaggcca   900
gtcggggagt attgggggct tgctgggggg cagatttgtc acgctgcgcg ctttcataga   960
ccccattaat gtggggtgaa gagctgtaaa gtaccgctaa aaactttgca agggtgctt   1020 cgcaacttgt aaccgctccg tattgttttc tacggcaata agcatttgtg ctgctcaaag  1080
cgtggaattg agatcggttt gaaaattaca aaataaaact ttgcaaaccg ggctgtacgc  1140
aaggcggacg aacgctaaac tatgtaagaa atcacaactt ccctcagta gtgccaggag  1200 gcacaagcct gaa gtg tca tca atg aga agg ttc agg ctg aaa cta gaa      1249
              Val Ser Ser Met Arg Arg Phe Arg Leu Lys Leu Glu
                1               5                   10 agg cga tgt atg tct gac aca ccg acc tca gct ctg atc acc acg gtc    1297
Arg Arg Cys Met Ser Asp Thr Pro Thr Ser Ala Leu Ile Thr Thr Val
         15                  20                  25 aac cgc agc ttc gat gga ttc gat ttg gaa gaa gta gca gca gac ctt    1345
Asn Arg Ser Phe Asp Gly Phe Asp Leu Glu Glu Val Ala Ala Asp Leu
     30                  35                  40 gga gtt cgg ctc acc gac ctg ccc gac gaa gaa cta gaa gta tcc aaa    1393
Gly Val Arg Leu Thr Asp Leu Pro Asp Glu Glu Leu Glu Val Ser Lys
45                  50                  55                  60 gtt ctc gcg gcg gac ctc ctc gct gag ggg cca gct ctc atc atc ggt    1441
Val Leu Ala Ala Asp Leu Leu Ala Glu Gly Pro Ala Leu Ile Ile Gly
             65                  70                  75 gta gga aac acg ttt ttc gac gcc cag gtc gcc gct gcc ctc ggc gtc    1489
Val Gly Asn Thr Phe Phe Asp Ala Gln Val Ala Ala Ala Leu Gly Val
         80                  85                  90 cca gtg cta ctg ctg gta gac aag caa ggc aag cac gtt gct ctt gct    1537
Pro Val Leu Leu Leu Val Asp Lys Gln Gly Lys His Val Ala Leu Ala
     95                 100                 105 cgc acc cag gta aac aat gcc ggc gca gtt gtt gca gca gca ttt acc    1585
Arg Thr Gln Val Asn Asn Ala Gly Ala Val Val Ala Ala Ala Phe Thr
    110                 115                 120 gct gaa caa gag cca atg ccg gat aag ctg cgc aag gct gtg cgc aac    1633
Ala Glu Gln Glu Pro Met Pro Asp Lys Leu Arg Lys Ala Val Arg Asn
125                 130                 135                 140 cac agc aac ctc gaa cca gtc atg agc gcc gaa ctc ttt gaa aac tgg    1681
His Ser Asn Leu Glu Pro Val Met Ser Ala Glu Leu Phe Glu Asn Trp
                145                 150                 155
```

```
ctg ctc aag cgc gca cgc gca gag cac tcc cac att gtg ctg cca gaa    1729
Leu Leu Lys Arg Ala Arg Ala Glu His Ser His Ile Val Leu Pro Glu
        160             165             170 ggt gac gac gac cgc atc ttg atg gct gcc cac cag ctg ctt gat caa    1777
Gly Asp Asp Asp Arg Ile Leu Met Ala Ala His Gln Leu Leu Asp Gln
175             180             185 gac atc tgt gac atc acg atc ctg ggc gat cca gta cag atc aag gag    1825
Asp Ile Cys Asp Ile Thr Ile Leu Gly Asp Pro Val Gln Ile Lys Glu
        190             195             200 cgc gct acc gaa ctt ggc ctg cac ctt aac act gca tac ctg gtc aat    1873
Arg Ala Thr Glu Leu Gly Leu His Leu Asn Thr Ala Tyr Leu Val Asn
205             210             215             220 ccg ctg aca gat cct cgc ctg gag gaa ttc gcc gaa caa ttc gcg gag    1921
Pro Leu Thr Asp Pro Arg Leu Glu Glu Phe Ala Glu Gln Phe Ala Glu
        225             230             235 ctg cgc aag tca aag agc gtc act atc gat gaa gcc cgc gaa atc atg    1969
Leu Arg Lys Ser Lys Ser Val Thr Ile Asp Glu Ala Arg Glu Ile Met
        240             245             250 aag gat att tgc tac ttc ggc acc atg atg gtc cac aac ggc gac gcc    2017
Lys Asp Ile Cys Tyr Phe Gly Thr Met Met Val His Asn Gly Asp Ala
        255             260             265 gac gga atg gta tcc ggt gca gca aac acc acc gca cac acc att aag    2065
Asp Gly Met Val Ser Gly Ala Ala Asn Thr Thr Ala His Thr Ile Lys
270             275             280 cca agc ttc cag atc atc aaa act gtt cca gaa gca tcc gtc gtt tct    2113
Pro Ser Phe Gln Ile Ile Lys Thr Val Pro Glu Ala Ser Val Val Ser
285             290             295             300 tcc atc ttc ctc atg gtg ctg cgc ggg cga ctg tgg gca ttc ggc gac    2161
Ser Ile Phe Leu Met Val Leu Arg Gly Arg Leu Trp Ala Phe Gly Asp
        305             310             315 tgt gct gtt aac ccg aac cca act gct gaa cag ctt ggt gaa atc gcc    2209
Cys Ala Val Asn Pro Asn Pro Thr Ala Glu Gln Leu Gly Glu Ile Ala
        320             325             330 gtt gtg tca gca aaa act gca gca caa ttt ggc att gat cct cgc gta    2257
Val Val Ser Ala Lys Thr Ala Ala Gln Phe Gly Ile Asp Pro Arg Val
        335             340             345 gcc atc ttg tcc tac tcc act ggc aac tcc ggc gga ggc tca gat gtg    2305
Ala Ile Leu Ser Tyr Ser Thr Gly Asn Ser Gly Gly Gly Ser Asp Val
350             355             360 gat cgc gcc atc gac gct ctt gca gaa gca cgc cga ctt aac cca gaa    2353
Asp Arg Ala Ile Asp Ala Leu Ala Glu Ala Arg Arg Leu Asn Pro Glu
365             370             375             380 cta tgc gtc gat gga cca ctt cag ttc gac gcc gcc gtc gac ccg ggt    2401
Leu Cys Val Asp Gly Pro Leu Gln Phe Asp Ala Ala Val Asp Pro Gly
        385             390             395 gtg gcg cgc aag aag atg cca gac tct gac gtc gct ggc cag gca aat    2449
Val Ala Arg Lys Lys Met Pro Asp Ser Asp Val Ala Gly Gln Ala Asn
        400             405             410 gtg ttt atc ttc cct gac ctg gaa gcc gga aac atc ggc tac aaa act    2497
Val Phe Ile Phe Pro Asp Leu Glu Ala Gly Asn Ile Gly Tyr Lys Thr
        415             420             425 gca caa cgc acc ggt cac gcc ctg gca gtt ggt ccg att ctg cag ggc    2545
Ala Gln Arg Thr Gly His Ala Leu Ala Val Gly Pro Ile Leu Gln Gly
430             435             440 cta aac aaa cca gtc aac gac ctt tcc cgt ggc gca aca gtc cct gac    2593
Leu Asn Lys Pro Val Asn Asp Leu Ser Arg Gly Ala Thr Val Pro Asp
445             450             455             460 atc gtc aac aca gta gcc atc aca gca att cag gca gga gga cgc agc    2641
Ile Val Asn Thr Val Ala Ile Thr Ala Ile Gln Ala Gly Gly Arg Ser
        465             470             475
``` taa                                                                                    2644

<210> SEQ ID NO 35
<211> LENGTH: 476
<212> TYPE: PRT
<213> ORGANISM: Corynebacterium glutamicum

<400> SEQUENCE: 35

Val Ser Ser Met Arg Arg Phe Arg Leu Lys Leu Glu Arg Arg Cys Met
1               5                   10                  15

Ser Asp Thr Pro Thr Ser Ala Leu Ile Thr Thr Val Asn Arg Ser Phe
            20                  25                  30

Asp Gly Phe Asp Leu Glu Glu Val Ala Ala Asp Leu Gly Val Arg Leu
        35                  40                  45

Thr Asp Leu Pro Asp Glu Glu Leu Glu Val Ser Lys Val Leu Ala Ala
    50                  55                  60

Asp Leu Leu Ala Glu Gly Pro Ala Leu Ile Ile Gly Val Gly Asn Thr
65                  70                  75                  80

Phe Phe Asp Ala Gln Val Ala Ala Ala Leu Gly Val Pro Val Leu Leu
                85                  90                  95

Leu Val Asp Lys Gln Gly Lys His Val Ala Leu Ala Arg Thr Gln Val
            100                 105                 110

Asn Asn Ala Gly Ala Val Val Ala Ala Phe Thr Ala Glu Gln Glu
        115                 120                 125

Pro Met Pro Asp Lys Leu Arg Lys Ala Val Arg Asn His Ser Asn Leu
    130                 135                 140

Glu Pro Val Met Ser Ala Glu Leu Phe Glu Asn Trp Leu Leu Lys Arg
145                 150                 155                 160

Ala Arg Ala Glu His Ser His Ile Val Leu Pro Glu Gly Asp Asp Asp
                165                 170                 175

Arg Ile Leu Met Ala Ala His Gln Leu Leu Asp Gln Asp Ile Cys Asp
            180                 185                 190

Ile Thr Ile Leu Gly Asp Pro Val Gln Ile Lys Glu Arg Ala Thr Glu
        195                 200                 205

Leu Gly Leu His Leu Asn Thr Ala Tyr Leu Val Asn Pro Leu Thr Asp
    210                 215                 220

Pro Arg Leu Glu Glu Phe Ala Glu Gln Phe Ala Glu Leu Arg Lys Ser
225                 230                 235                 240

Lys Ser Val Thr Ile Asp Glu Ala Arg Glu Ile Met Lys Asp Ile Cys
                245                 250                 255

Tyr Phe Gly Thr Met Met Val His Asn Gly Asp Ala Asp Gly Met Val
            260                 265                 270

Ser Gly Ala Ala Asn Thr Thr Ala His Thr Ile Lys Pro Ser Phe Gln
        275                 280                 285

Ile Ile Lys Thr Val Pro Glu Ala Ser Val Val Ser Ile Phe Leu
    290                 295                 300

Met Val Leu Arg Gly Arg Leu Trp Ala Phe Gly Asp Cys Ala Val Asn
305                 310                 315                 320

Pro Asn Pro Thr Ala Glu Gln Leu Gly Glu Ile Ala Val Val Ser Ala
                325                 330                 335

Lys Thr Ala Ala Gln Phe Gly Ile Asp Pro Arg Val Ala Ile Leu Ser
            340                 345                 350

Tyr Ser Thr Gly Asn Ser Gly Gly Gly Ser Asp Val Asp Arg Ala Ile
        355                 360                 365

```
Asp Ala Leu Ala Glu Ala Arg Arg Leu Asn Pro Glu Leu Cys Val Asp
        370                 375                 380

Gly Pro Leu Gln Phe Asp Ala Ala Val Asp Pro Gly Val Ala Arg Lys
385                 390                 395                 400

Lys Met Pro Asp Ser Asp Val Ala Gly Gln Ala Asn Val Phe Ile Phe
                405                 410                 415

Pro Asp Leu Glu Ala Gly Asn Ile Gly Tyr Lys Thr Ala Gln Arg Thr
            420                 425                 430

Gly His Ala Leu Ala Val Gly Pro Ile Leu Gln Gly Leu Asn Lys Pro
            435                 440                 445

Val Asn Asp Leu Ser Arg Gly Ala Thr Val Pro Asp Ile Val Asn Thr
    450                 455                 460

Val Ala Ile Thr Ala Ile Gln Ala Gly Gly Arg Ser
465                 470                 475

<210> SEQ ID NO 36
<211> LENGTH: 1425
<212> TYPE: DNA
<213> ORGANISM: Corynebacterium glutamicum
<220> FEATURE:
<221> NAME/KEY: CDS
<222> LOCATION: (1)..(1422)

<400> SEQUENCE: 36 atg gga aag aca tat gtg ggg tcc agg ctg cgc caa ctg cgc cgc gaa      48
Met Gly Lys Thr Tyr Val Gly Ser Arg Leu Arg Gln Leu Arg Arg Glu
1               5                   10                  15 aga gac ctg agc cag gcg tcg ttg gca gca acc ctt ggc tta tct gcc      96
Arg Asp Leu Ser Gln Ala Ser Leu Ala Ala Thr Leu Gly Leu Ser Ala
            20                  25                  30 agt tat gta aat cag att gag cac gac gta cgc ccg ctc acc gta ccg     144
Ser Tyr Val Asn Gln Ile Glu His Asp Val Arg Pro Leu Thr Val Pro
        35                  40                  45 gtg tta ttg cgc atc acc gag gcg ttc ggc gta gac gca acg ttt ttc     192
Val Leu Leu Arg Ile Thr Glu Ala Phe Gly Val Asp Ala Thr Phe Phe
    50                  55                  60 tcc cgc gac gat gat tcc cgc ctt tta gct gaa gtt cag gat gtc atg     240
Ser Arg Asp Asp Asp Ser Arg Leu Leu Ala Glu Val Gln Asp Val Met
65                  70                  75                  80 ttg gac cgg gag atc aac ccc gcg aac gtg gag ctc caa gag cta tcg     288
Leu Asp Arg Glu Ile Asn Pro Ala Asn Val Glu Leu Gln Glu Leu Ser
                85                  90                  95 gag atg gtg tac aac cac ccg cag ctg gcg cgc gcc atg gtg gaa atg     336
Glu Met Val Tyr Asn His Pro Gln Leu Ala Arg Ala Met Val Glu Met
            100                 105                 110 cac cag cgc tac cga aac gta cgc gac aag ttc tcc atc gca gtg gac     384
His Gln Arg Tyr Arg Asn Val Arg Asp Lys Phe Ser Ile Ala Val Asp
        115                 120                 125 aat cgc acc aac acg cct gag gaa cgt cgc ccc atc gcg gag gcc gtg     432
Asn Arg Thr Asn Thr Pro Glu Glu Arg Arg Pro Ile Ala Glu Ala Val
    130                 135                 140 agc atg ccg cac gaa gag gtg cgc gat ttc att tac gcc cgc caa aac     480
Ser Met Pro His Glu Glu Val Arg Asp Phe Ile Tyr Ala Arg Gln Asn
145                 150                 155                 160 tac ttc gat gcg ctc gac cgc cgc gcc gaa gcc atc gcc gca caa ctg     528
Tyr Phe Asp Ala Leu Asp Arg Arg Ala Glu Ala Ile Ala Ala Gln Leu
                165                 170                 175 ggc tgg cag ccg tac gat tcc cgc gcc atg gaa gat tcg atc gcc agg     576
Gly Trp Gln Pro Tyr Asp Ser Arg Ala Met Glu Asp Ser Ile Ala Arg
            180                 185                 190
```

```
cgc ctg caa atg gat cac gat gtc acc atc acc tcc tcc aaa gag gaa      624
Arg Leu Gln Met Asp His Asp Val Thr Ile Thr Ser Ser Lys Glu Glu
            195                 200                 205 tcc ggc acg ctg cac cac ttt gac ccc gag acg cgc cta ctg aca atc      672
Ser Gly Thr Leu His His Phe Asp Pro Glu Thr Arg Leu Leu Thr Ile
210                 215                 220 cac gca cgc ctc aac ccc gga caa cgc gcc ttc cgc atg gcc acc gaa      720
His Ala Arg Leu Asn Pro Gly Gln Arg Ala Phe Arg Met Ala Thr Glu
225                 230                 235                 240 ctc ggc tac cta gaa gcc aac gac ctc atc gaa ggc atc gtc gac gac      768
Leu Gly Tyr Leu Glu Ala Asn Asp Leu Ile Glu Gly Ile Val Asp Asp
            245                 250                 255 ggc atc tgg tcc acc ccc gaa gcc cgc acc cta gcc atc cgc ggc gtc      816
Gly Ile Trp Ser Thr Pro Glu Ala Arg Thr Leu Ala Ile Arg Gly Val
        260                 265                 270 gcc tcc tac ttc gcc gcc gcc gta atg ctg ccc tac aaa atc ttc cac      864
Ala Ser Tyr Phe Ala Ala Ala Val Met Leu Pro Tyr Lys Ile Phe His
            275                 280                 285 tcc gag gcc gaa aaa tcc ggc tac gac atc gaa tac cta ggt cag ctt      912
Ser Glu Ala Glu Lys Ser Gly Tyr Asp Ile Glu Tyr Leu Gly Gln Leu
290                 295                 300 ttc ggc gtg ggc tac gag acg acc gcc cac cgc ctg tcc acc ctg cag      960
Phe Gly Val Gly Tyr Glu Thr Thr Ala His Arg Leu Ser Thr Leu Gln
305                 310                 315                 320 cgt ccc aac ctg cgc ggc atc ccg ttt acc ttc gtg cgc gtc gac cgc     1008
Arg Pro Asn Leu Arg Gly Ile Pro Phe Thr Phe Val Arg Val Asp Arg
            325                 330                 335 gcc ggc aac atg tcc aaa cgc caa tcc gcc acc ggc ttc cac ttc acc     1056
Ala Gly Asn Met Ser Lys Arg Gln Ser Ala Thr Gly Phe His Phe Thr
        340                 345                 350 cac tac ggc ggc acc tgc ccc ctg tgg aac gtg ttt gaa acc ttc acc     1104
His Tyr Gly Gly Thr Cys Pro Leu Trp Asn Val Phe Glu Thr Phe Thr
            355                 360                 365 aac ccc ggc caa gtg ctc cgc caa ttc gcg caa atg ccc gac gga cgc     1152
Asn Pro Gly Gln Val Leu Arg Gln Phe Ala Gln Met Pro Asp Gly Arg
370                 375                 380 aac tac ctg tgg atc tca cgc acc gtg cga cac cac gaa gcc cgg ttc     1200
Asn Tyr Leu Trp Ile Ser Arg Thr Val Arg His His Glu Ala Arg Phe
385                 390                 395                 400 ggc gaa gtg gac aaa atg ttc gcc atc ggg ctc ggc tgc gaa gcg cgc     1248
Gly Glu Val Asp Lys Met Phe Ala Ile Gly Leu Gly Cys Glu Ala Arg
            405                 410                 415 cac gcc gac cgc acc gtg tac tcc cgc ggc ttc aac ctc cag gac cta     1296
His Ala Asp Arg Thr Val Tyr Ser Arg Gly Phe Asn Leu Gln Asp Leu
        420                 425                 430 tcc acc gcc acc ccc atc ggg tcc ggc tgc cga gtg tgc acc cgc gag     1344
Ser Thr Ala Thr Pro Ile Gly Ser Gly Cys Arg Val Cys Thr Arg Glu
            435                 440                 445 aac tgc gcg cag cgc gca ttc ccg tcc gtg cac ggc cgc atc aac atc     1392
Asn Cys Ala Gln Arg Ala Phe Pro Ser Val His Gly Arg Ile Asn Ile
450                 455                 460 gac gcg cac gag tcc act atc gcg ccg tac taa                          1425
Asp Ala His Glu Ser Thr Ile Ala Pro Tyr
465                 470
```

<210> SEQ ID NO 37
<211> LENGTH: 474
<212> TYPE: PRT
<213> ORGANISM: Corynebacterium glutamicum

<400> SEQUENCE: 37

```
Met Gly Lys Thr Tyr Val Gly Ser Arg Leu Arg Gln Leu Arg Arg Glu
 1               5                  10                  15
Arg Asp Leu Ser Gln Ala Ser Leu Ala Ala Thr Leu Gly Leu Ser Ala
             20                  25                  30
Ser Tyr Val Asn Gln Ile Glu His Asp Val Arg Pro Leu Thr Val Pro
             35                  40                  45
Val Leu Leu Arg Ile Thr Glu Ala Phe Gly Val Asp Ala Thr Phe Phe
 50                  55                  60
Ser Arg Asp Asp Asp Ser Arg Leu Leu Ala Glu Val Gln Asp Val Met
 65                  70                  75                  80
Leu Asp Arg Glu Ile Asn Pro Ala Asn Val Leu Gln Glu Leu Ser
                 85                  90                  95
Glu Met Val Tyr Asn His Pro Gln Leu Ala Arg Ala Met Val Glu Met
                100                 105                 110
His Gln Arg Tyr Arg Asn Val Arg Asp Lys Phe Ser Ile Ala Val Asp
             115                 120                 125
Asn Arg Thr Asn Thr Pro Glu Glu Arg Pro Ile Ala Glu Ala Val
         130                 135                 140
Ser Met Pro His Glu Glu Val Arg Asp Phe Ile Tyr Ala Arg Gln Asn
145                 150                 155                 160
Tyr Phe Asp Ala Leu Asp Arg Arg Ala Glu Ala Ile Ala Ala Gln Leu
                165                 170                 175
Gly Trp Gln Pro Tyr Asp Ser Arg Ala Met Glu Asp Ser Ile Ala Arg
                180                 185                 190
Arg Leu Gln Met Asp His Asp Val Thr Ile Thr Ser Ser Lys Glu Glu
             195                 200                 205
Ser Gly Thr Leu His His Phe Asp Pro Glu Thr Arg Leu Leu Thr Ile
210                 215                 220
His Ala Arg Leu Asn Pro Gly Gln Arg Ala Phe Arg Met Ala Thr Glu
225                 230                 235                 240
Leu Gly Tyr Leu Glu Ala Asn Asp Leu Ile Glu Gly Ile Val Asp Asp
                245                 250                 255
Gly Ile Trp Ser Thr Pro Glu Ala Arg Thr Leu Ala Ile Arg Gly Val
                260                 265                 270
Ala Ser Tyr Phe Ala Ala Ala Val Met Leu Pro Tyr Lys Ile Phe His
         275                 280                 285
Ser Glu Ala Glu Lys Ser Gly Tyr Asp Ile Glu Tyr Leu Gly Gln Leu
         290                 295                 300
Phe Gly Val Gly Tyr Glu Thr Thr Ala His Arg Leu Ser Thr Leu Gln
305                 310                 315                 320
Arg Pro Asn Leu Arg Gly Ile Pro Phe Thr Phe Val Arg Val Asp Arg
                325                 330                 335
Ala Gly Asn Met Ser Lys Arg Gln Ser Ala Thr Gly Phe His Phe Thr
             340                 345                 350
His Tyr Gly Gly Thr Cys Pro Leu Trp Asn Val Phe Glu Thr Phe Thr
         355                 360                 365
Asn Pro Gly Gln Val Leu Arg Gln Phe Ala Gln Met Pro Asp Gly Arg
     370                 375                 380
Asn Tyr Leu Trp Ile Ser Arg Thr Val Arg His His Glu Ala Arg Phe
385                 390                 395                 400
Gly Glu Val Asp Lys Met Phe Ala Ile Gly Leu Gly Cys Glu Ala Arg
                405                 410                 415
His Ala Asp Arg Thr Val Tyr Ser Arg Gly Phe Asn Leu Gln Asp Leu
             420                 425                 430
```

```
Ser Thr Ala Thr Pro Ile Gly Ser Gly Cys Arg Val Cys Thr Arg Glu
        435                 440                 445

Asn Cys Ala Gln Arg Ala Phe Pro Ser Val His Gly Arg Ile Asn Ile
    450                 455                 460

Asp Ala His Glu Ser Thr Ile Ala Pro Tyr
465                 470

<210> SEQ ID NO 38
<211> LENGTH: 18
<212> TYPE: DNA
<213> ORGANISM: Corynebacterium glutamicum

<400> SEQUENCE: 38
aaaaaaaaaa aaaaaaaa                                                  18

<210> SEQ ID NO 39
<211> LENGTH: 17
<212> TYPE: DNA
<213> ORGANISM: Corynebacterium glutamicum

<400> SEQUENCE: 39
aaaaaaaaaa aaaaaaa                                                   17

<210> SEQ ID NO 40
<211> LENGTH: 1386
<212> TYPE: DNA
<213> ORGANISM: Corynebacterium glutamicum
<220> FEATURE:
<221> NAME/KEY: CDS
<222> LOCATION: (1)..(1383)

<400> SEQUENCE: 40 atg tct gac aca ccg acc tca gct ctg atc acc acg gtc aac cgc agc    48
Met Ser Asp Thr Pro Thr Ser Ala Leu Ile Thr Thr Val Asn Arg Ser
1               5                   10                  15 ttc gat gga ttc gat ttg gaa gaa gta gca gca gac ctt gga gtt cgg    96
Phe Asp Gly Phe Asp Leu Glu Glu Val Ala Ala Asp Leu Gly Val Arg
            20                  25                  30 ctc acc tac ctg ccc gac gaa gaa cta gaa gta tcc aaa gtt ctc gcg   144
Leu Thr Tyr Leu Pro Asp Glu Glu Leu Glu Val Ser Lys Val Leu Ala
        35                  40                  45 gcg gac ctc ctc gct gag ggg cca gct ctc atc atc ggt gta gga aac   192
Ala Asp Leu Leu Ala Glu Gly Pro Ala Leu Ile Ile Gly Val Gly Asn
    50                  55                  60 acg ttt ttc gac gcc cag gtc gcc gct gcc ctc ggc gtc cca gtg cta   240
Thr Phe Phe Asp Ala Gln Val Ala Ala Ala Leu Gly Val Pro Val Leu
65                  70                  75                  80 ctg ctg gta gac aag caa ggc aag cac gtt gct ctt gct cgc acc cag   288
Leu Leu Val Asp Lys Gln Gly Lys His Val Ala Leu Ala Arg Thr Gln
                85                  90                  95 gta aac aat gcc ggc gca gtt gtt gca gca gca ttt acc gct gaa caa   336
Val Asn Asn Ala Gly Ala Val Val Ala Ala Ala Phe Thr Ala Glu Gln
            100                 105                 110 gag cca atg ccg gat aag ctg cgc aag gct gtg cgc aac cac agc aac   384
Glu Pro Met Pro Asp Lys Leu Arg Lys Ala Val Arg Asn His Ser Asn
        115                 120                 125 ctc gaa cca gtc atg agc gcc gaa ctc ttt gaa aac tgg ctg ctc aag   432
Leu Glu Pro Val Met Ser Ala Glu Leu Phe Glu Asn Trp Leu Leu Lys
    130                 135                 140 cgc gca cgc gca gag cac tcc cac att gtg ctg cca gaa ggt gac gac   480
Arg Ala Arg Ala Glu His Ser His Ile Val Leu Pro Glu Gly Asp Asp
145                 150                 155                 160
```

```
gac cgc atc ttg atg gct gcc cac cag ctg ctt gat caa gac atc tgt       528
Asp Arg Ile Leu Met Ala Ala His Gln Leu Leu Asp Gln Asp Ile Cys
            165                 170                 175 gac atc acg atc ctg ggc gat cca gta aag atc aag gag cgc gct acc       576
Asp Ile Thr Ile Leu Gly Asp Pro Val Lys Ile Lys Glu Arg Ala Thr
        180                 185                 190 gaa ctt ggc ctg cac ctt aac act gca tac ctg gtc aat ccg ctg aca       624
Glu Leu Gly Leu His Leu Asn Thr Ala Tyr Leu Val Asn Pro Leu Thr
    195                 200                 205 gat cct cgc ctg gag gaa ttc gcc gaa caa ttc gcg gag ctg cgc aag       672
Asp Pro Arg Leu Glu Glu Phe Ala Glu Gln Phe Ala Glu Leu Arg Lys
210                 215                 220 tca aag agc gtc act atc gat gaa gcc cgc gaa atc atg aag gat att       720
Ser Lys Ser Val Thr Ile Asp Glu Ala Arg Glu Ile Met Lys Asp Ile
225                 230                 235                 240 tcc tac ttc ggc acc atg atg gtc cac aac ggc gac gcc gac gga atg       768
Ser Tyr Phe Gly Thr Met Met Val His Asn Gly Asp Ala Asp Gly Met
                245                 250                 255 gta tcc ggt gca gca aac acc acc gca cac acc att aag cca agc ttc       816
Val Ser Gly Ala Ala Asn Thr Thr Ala His Thr Ile Lys Pro Ser Phe
            260                 265                 270 cag atc atc aaa act gtt cca gaa gca tcc gtc gtt tct tcc atc ttc       864
Gln Ile Ile Lys Thr Val Pro Glu Ala Ser Val Val Ser Ser Ile Phe
        275                 280                 285 ctc atg gtg ctg cgc ggg cga ctg tgg gca ttc ggc gac tgt gct gtt       912
Leu Met Val Leu Arg Gly Arg Leu Trp Ala Phe Gly Asp Cys Ala Val
    290                 295                 300 aac ccg aac cca act gct gaa cag ctt ggt gaa atc gcc gtt gtg tca       960
Asn Pro Asn Pro Thr Ala Glu Gln Leu Gly Glu Ile Ala Val Val Ser
305                 310                 315                 320 gca aaa act gca gca caa ttt ggc att gat cct cgc gta gcc atc ttg      1008
Ala Lys Thr Ala Ala Gln Phe Gly Ile Asp Pro Arg Val Ala Ile Leu
                325                 330                 335 tcc tac tcc act ggc aac tcc ggc gga ggc tca gat gtg gat cgc gcc      1056
Ser Tyr Ser Thr Gly Asn Ser Gly Gly Gly Ser Asp Val Asp Arg Ala
            340                 345                 350 atc gac gct ctt gca gaa gca cgc cga ctt aac cca gaa cta tgc gtc      1104
Ile Asp Ala Leu Ala Glu Ala Arg Arg Leu Asn Pro Glu Leu Cys Val
        355                 360                 365 gat gga cca ctt cag ttc gac gcc gcc gtc gac ccg ggt gtg gcg cgc      1152
Asp Gly Pro Leu Gln Phe Asp Ala Ala Val Asp Pro Gly Val Ala Arg
    370                 375                 380 aag aag atg cca gac tct gac gtc gct ggc cag gca aat gtg ttt atc      1200
Lys Lys Met Pro Asp Ser Asp Val Ala Gly Gln Ala Asn Val Phe Ile
385                 390                 395                 400 ttc cct gac ctg gaa gcc gga aac atc ggc tac aaa act gca caa cgc      1248
Phe Pro Asp Leu Glu Ala Gly Asn Ile Gly Tyr Lys Thr Ala Gln Arg
                405                 410                 415 acc ggt cac gcc ctg gca gtt ggt ccg att ctg cag ggc cta aac aaa      1296
Thr Gly His Ala Leu Ala Val Gly Pro Ile Leu Gln Gly Leu Asn Lys
            420                 425                 430 cca gtc aac gac ctt tcc cgt ggc gca aca gtc cct gac atc gtc aac      1344
Pro Val Asn Asp Leu Ser Arg Gly Ala Thr Val Pro Asp Ile Val Asn
        435                 440                 445 aca gta gcc atc aca gca att cag gca gga gga cgc agc taa              1386
Thr Val Ala Ile Thr Ala Ile Gln Ala Gly Gly Arg Ser
    450                 455                 460

<210> SEQ ID NO 41
<211> LENGTH: 461
```

<212> TYPE: PRT
<213> ORGANISM: Corynebacterium glutamicum

<400> SEQUENCE: 41

```
Met Ser Asp Thr Pro Thr Ser Ala Leu Ile Thr Thr Val Asn Arg Ser
1               5                   10                  15

Phe Asp Gly Phe Asp Leu Glu Glu Val Ala Ala Asp Leu Gly Val Arg
            20                  25                  30

Leu Thr Tyr Leu Pro Asp Glu Leu Glu Val Ser Lys Val Leu Ala
        35                  40                  45

Ala Asp Leu Leu Ala Glu Gly Pro Ala Leu Ile Ile Gly Val Gly Asn
    50                  55                  60

Thr Phe Phe Asp Ala Gln Val Ala Ala Leu Gly Val Pro Val Leu
65                  70                  75                  80

Leu Leu Val Asp Lys Gln Gly Lys His Val Ala Leu Ala Arg Thr Gln
            85                  90                  95

Val Asn Asn Ala Gly Ala Val Val Ala Ala Phe Thr Ala Glu Gln
                100                 105                 110

Glu Pro Met Pro Asp Lys Leu Arg Lys Ala Val Arg Asn His Ser Asn
            115                 120                 125

Leu Glu Pro Val Met Ser Ala Glu Leu Phe Glu Asn Trp Leu Leu Lys
130                 135                 140

Arg Ala Arg Ala Glu His Ser His Ile Val Leu Pro Glu Gly Asp Asp
145                 150                 155                 160

Asp Arg Ile Leu Met Ala Ala His Gln Leu Leu Asp Gln Asp Ile Cys
            165                 170                 175

Asp Ile Thr Ile Leu Gly Asp Pro Val Lys Ile Lys Glu Arg Ala Thr
        180                 185                 190

Glu Leu Gly Leu His Leu Asn Thr Ala Tyr Leu Val Asn Pro Leu Thr
    195                 200                 205

Asp Pro Arg Leu Glu Glu Phe Ala Glu Gln Phe Ala Glu Leu Arg Lys
210                 215                 220

Ser Lys Ser Val Thr Ile Asp Glu Ala Arg Glu Ile Met Lys Asp Ile
225                 230                 235                 240

Ser Tyr Phe Gly Thr Met Met Val His Asn Gly Asp Ala Asp Gly Met
            245                 250                 255

Val Ser Gly Ala Ala Asn Thr Thr Ala His Thr Ile Lys Pro Ser Phe
        260                 265                 270

Gln Ile Ile Lys Thr Val Pro Gly Ala Ser Val Ser Ser Ile Phe
    275                 280                 285

Leu Met Val Leu Arg Gly Arg Leu Trp Ala Phe Gly Asp Cys Ala Val
290                 295                 300

Asn Pro Asn Pro Thr Ala Glu Gln Leu Gly Glu Ile Ala Val Val Ser
305                 310                 315                 320

Ala Lys Thr Ala Ala Gln Phe Gly Ile Asp Pro Arg Val Ala Ile Leu
            325                 330                 335

Ser Tyr Ser Thr Gly Asn Ser Gly Gly Gly Ser Asp Val Asp Arg Ala
        340                 345                 350

Ile Asp Ala Leu Ala Glu Ala Arg Arg Leu Asn Pro Glu Leu Cys Val
    355                 360                 365

Asp Gly Pro Leu Gln Phe Asp Ala Ala Val Asp Pro Gly Val Ala Arg
370                 375                 380

Lys Lys Met Pro Asp Ser Asp Val Ala Gly Gln Ala Asn Val Phe Ile
385                 390                 395                 400
```

```
Phe Pro Asp Leu Glu Ala Gly Asn Ile Gly Tyr Lys Thr Ala Gln Arg
            405                 410                 415

Thr Gly His Ala Leu Ala Val Gly Pro Ile Leu Gln Gly Leu Asn Lys
        420                 425                 430

Pro Val Asn Asp Leu Ser Arg Gly Ala Thr Val Pro Asp Ile Val Asn
    435                 440                 445

Thr Val Ala Ile Thr Ala Ile Gln Ala Gly Gly Arg Ser
    450                 455                 460

<210> SEQ ID NO 42
<211> LENGTH: 1425
<212> TYPE: DNA
<213> ORGANISM: Corynebacterium glutamicum
<220> FEATURE:
<221> NAME/KEY: CDS
<222> LOCATION: (1)..(1422)

<400> SEQUENCE: 42
```

| | | |
|---|---|---|
| atg gga aag aca tat gtg ggg tcc agg ctg cgc caa ctg cgc cgc gaa<br>Met Gly Lys Thr Tyr Val Gly Ser Arg Leu Arg Gln Leu Arg Arg Glu<br>1               5                  10               15 | | 48 |
| aga gac ctg agc cag gca tcc tta gca gca acc ctt ggc tta tct gca<br>Arg Asp Leu Ser Gln Ala Ser Leu Ala Ala Thr Leu Gly Leu Ser Ala<br>              20                  25                30 | | 96 |
| agt tat gta aat cag att gag cac gac gta cgc ccg ctc acc gta ccg<br>Ser Tyr Val Asn Gln Ile Glu His Asp Val Arg Pro Leu Thr Val Pro<br>              35                  40              45 | | 144 |
| gtg tta ttg cgc atc acc gag gcg ttc ggc gta gac gca acg ttt ttc<br>Val Leu Leu Arg Ile Thr Glu Ala Phe Gly Val Asp Ala Thr Phe Phe<br>50                  55                  60 | | 192 |
| tcc cgc gac gat gac tcc cgc ctg ctc gcc gag gtc caa gac gtc atg<br>Ser Arg Asp Asp Asp Ser Arg Leu Leu Ala Glu Val Gln Asp Val Met<br>65                70                  75              80 | | 240 |
| ctg gac cgg gag atc aat cct gcg aac gtg gag ctg caa gag ctt tcg<br>Leu Asp Arg Glu Ile Asn Pro Ala Asn Val Glu Leu Gln Glu Leu Ser<br>                   85                  90              95 | | 288 |
| gag atg gtg tac aac cac ccc caa cta gcg cgc gcg atg gtg gaa atg<br>Glu Met Val Tyr Asn His Pro Gln Leu Ala Arg Ala Met Val Glu Met<br>                  100              105              110 | | 336 |
| cac cag cgt tac cga aac gtg cgc gat aag ttc tcc atc gca gtg gat<br>His Gln Arg Tyr Arg Asn Val Arg Asp Lys Phe Ser Ile Ala Val Asp<br>             115                  120              125 | | 384 |
| aat cgc acc aac acg cct gag gaa cgc cgt ccc atc gcg gag gcc gtg<br>Asn Arg Thr Asn Thr Pro Glu Glu Arg Arg Pro Ile Ala Glu Ala Val<br>130                  135                  140 | | 432 |
| agc atg ccg cac gaa gag gtc cgc gat ttc att tac gcc cgc caa aac<br>Ser Met Pro His Glu Glu Val Arg Asp Phe Ile Tyr Ala Arg Gln Asn<br>145                 150                  155              160 | | 480 |
| tac ttc gat gcc ctt gac cgc cgc gcc gaa gcc atc gcc gcg caa ctg<br>Tyr Phe Asp Ala Leu Asp Arg Arg Ala Glu Ala Ile Ala Ala Gln Leu<br>                  165              170              175 | | 528 |
| ggc tgg cag ccg tac gat tcc cgc gcc atg gaa gat tcg atc gcc cgc<br>Gly Trp Gln Pro Tyr Asp Ser Arg Ala Met Glu Asp Ser Ile Ala Arg<br>             180                  185              190 | | 576 |
| cgc ctg caa atg gat cac gat gtc acc atc acc tcc tcc aaa gag gaa<br>Arg Leu Gln Met Asp His Asp Val Thr Ile Thr Ser Ser Lys Glu Glu<br>             195                  200              205 | | 624 |
| tcc ggc acg ctg cac cac ttc gac ccc gag acg cgt ctg ctg aca atc<br>Ser Gly Thr Leu His His Phe Asp Pro Glu Thr Arg Leu Leu Thr Ile<br>210                215                  220 | | 672 |
| cac gca cgc ctc aac ccc ggg caa cgc gcc ttc cgc atg gcc acc gaa | | 720 |

```
His Ala Arg Leu Asn Pro Gly Gln Arg Ala Phe Arg Met Ala Thr Glu
225                 230                 235                 240 ctc ggc tac cta gaa gcc aac gac ctc atc gaa ggt atc gtt gac gac      768
Leu Gly Tyr Leu Glu Ala Asn Asp Leu Ile Glu Gly Ile Val Asp Asp
            245                 250                 255 ggc atc tgg tcc acc ccc gaa gcc cgc acc cta gcc atc cgc ggt gtg      816
Gly Ile Trp Ser Thr Pro Glu Ala Arg Thr Leu Ala Ile Arg Gly Val
        260                 265                 270 gcc tcc tac ttc gcc gcc gcc gtg atg ctg ccc tac aaa atc ttc cac      864
Ala Ser Tyr Phe Ala Ala Ala Val Met Leu Pro Tyr Lys Ile Phe His
    275                 280                 285 tcc gag gcc gaa aaa tcc ggc tac gac atc gag tac cta ggc caa ctc      912
Ser Glu Ala Glu Lys Ser Gly Tyr Asp Ile Glu Tyr Leu Gly Gln Leu
290                 295                 300 ttt ggc gtg ggc tat gag aca acc gcc cac cgc ttg tcc acc ctg cag      960
Phe Gly Val Gly Tyr Glu Thr Thr Ala His Arg Leu Ser Thr Leu Gln
305                 310                 315                 320 cgc ccc aac ctg cgc ggc atc ccc ttt acc ttc gtg cgc gtc gac cgc     1008
Arg Pro Asn Leu Arg Gly Ile Pro Phe Thr Phe Val Arg Val Asp Arg
            325                 330                 335 gcc ggc aac atg tcc aaa cgc caa tcc gcc acc ggc ttc cac ttc acc     1056
Ala Gly Asn Met Ser Lys Arg Gln Ser Ala Thr Gly Phe His Phe Thr
        340                 345                 350 cac tac ggc ggc acc tgc ccc ctg tgg aac gtg ttt gaa acc ttc acc     1104
His Tyr Gly Gly Thr Cys Pro Leu Trp Asn Val Phe Glu Thr Phe Thr
    355                 360                 365 aac ccc ggc caa gtg ctc cgc caa ttc gcg caa atg ccc gac gga cgc     1152
Asn Pro Gly Gln Val Leu Arg Gln Phe Ala Gln Met Pro Asp Gly Arg
370                 375                 380 aac tac ctg tgg atc tca cgc acc gtg cga cac cac gaa gcc cgg ttc     1200
Asn Tyr Leu Trp Ile Ser Arg Thr Val Arg His His Glu Ala Arg Phe
385                 390                 395                 400 ggc gaa gta gac aaa atg ttc gcc atc ggc ctg ggc tgc gaa gcg cgc     1248
Gly Glu Val Asp Lys Met Phe Ala Ile Gly Leu Gly Cys Glu Ala Arg
            405                 410                 415 cac gcc gac cgc act gtg tac tcc cgc ggt ttc aac ctc cag gac ctc     1296
His Ala Asp Arg Thr Val Tyr Ser Arg Gly Phe Asn Leu Gln Asp Leu
        420                 425                 430 tcc acc gcc acc ccc atc ggg tcc ggc tgc cga gtg tgc acc cgc gag     1344
Ser Thr Ala Thr Pro Ile Gly Ser Gly Cys Arg Val Cys Thr Arg Glu
    435                 440                 445 aac tgc gcg cag cgc gca ttc cca tcc gtc cac ggc cgc atc aac atc     1392
Asn Cys Ala Gln Arg Ala Phe Pro Ser Val His Gly Arg Ile Asn Ile
450                 455                 460 gac gcg cac gaa tcc act atc gcg ccg tac taa                         1425
Asp Ala His Glu Ser Thr Ile Ala Pro Tyr
465                 470

<210> SEQ ID NO 43
<211> LENGTH: 474
<212> TYPE: PRT
<213> ORGANISM: Corynebacterium glutamicum

<400> SEQUENCE: 43

Met Gly Lys Thr Tyr Val Gly Ser Arg Leu Arg Gln Leu Arg Arg Glu
1               5                   10                  15

Arg Asp Leu Ser Gln Ala Ser Leu Ala Ala Thr Leu Gly Leu Ser Ala
            20                  25                  30

Ser Tyr Val Asn Gln Ile Glu His Asp Val Arg Pro Leu Thr Val Pro
        35                  40                  45
```

```
Val Leu Leu Arg Ile Thr Glu Ala Phe Gly Val Asp Ala Thr Phe Phe
 50                  55                  60

Ser Arg Asp Asp Asp Ser Arg Leu Leu Ala Glu Val Gln Asp Val Met
 65                  70                  75                  80

Leu Asp Arg Glu Ile Asn Pro Ala Asn Val Glu Leu Gln Glu Leu Ser
                 85                  90                  95

Glu Met Val Tyr Asn His Pro Gln Leu Ala Arg Ala Met Val Glu Met
                100                 105                 110

His Gln Arg Tyr Arg Asn Val Arg Asp Lys Phe Ser Ile Ala Val Asp
            115                 120                 125

Asn Arg Thr Asn Thr Pro Glu Glu Arg Arg Pro Ile Ala Glu Ala Val
    130                 135                 140

Ser Met Pro His Glu Glu Val Arg Asp Phe Ile Tyr Ala Arg Gln Asn
145                 150                 155                 160

Tyr Phe Asp Ala Leu Asp Arg Arg Ala Glu Ala Ile Ala Ala Gln Leu
                165                 170                 175

Gly Trp Gln Pro Tyr Asp Ser Arg Ala Met Glu Asp Ser Ile Ala Arg
            180                 185                 190

Arg Leu Gln Met Asp His Asp Val Thr Ile Thr Ser Ser Lys Glu Glu
        195                 200                 205

Ser Gly Thr Leu His His Phe Asp Pro Glu Thr Arg Leu Leu Thr Ile
    210                 215                 220

His Ala Arg Leu Asn Pro Gly Gln Arg Ala Phe Arg Met Ala Thr Glu
225                 230                 235                 240

Leu Gly Tyr Leu Glu Ala Asn Asp Leu Ile Glu Gly Ile Val Asp Asp
                245                 250                 255

Gly Ile Trp Ser Thr Pro Glu Ala Arg Thr Leu Ala Ile Arg Gly Val
            260                 265                 270

Ala Ser Tyr Phe Ala Ala Val Met Leu Pro Tyr Lys Ile Phe His
        275                 280                 285

Ser Glu Ala Glu Lys Ser Gly Tyr Asp Ile Glu Tyr Leu Gly Gln Leu
    290                 295                 300

Phe Gly Val Gly Tyr Glu Thr Thr Ala His Arg Leu Ser Thr Leu Gln
305                 310                 315                 320

Arg Pro Asn Leu Arg Gly Ile Pro Phe Thr Phe Val Arg Val Asp Arg
                325                 330                 335

Ala Gly Asn Met Ser Lys Arg Gln Ser Ala Thr Gly Phe His Phe Thr
            340                 345                 350

His Tyr Gly Gly Thr Cys Pro Leu Trp Asn Val Phe Glu Thr Phe Thr
        355                 360                 365

Asn Pro Gly Gln Val Leu Arg Gln Phe Ala Gln Met Pro Asp Gly Arg
    370                 375                 380

Asn Tyr Leu Trp Ile Ser Arg Thr Val Arg His His Glu Ala Arg Phe
385                 390                 395                 400

Gly Glu Val Asp Lys Met Phe Ala Ile Gly Leu Gly Cys Glu Ala Arg
                405                 410                 415

His Ala Asp Arg Thr Val Tyr Ser Arg Gly Phe Asn Leu Gln Asp Leu
            420                 425                 430

Ser Thr Ala Thr Pro Ile Gly Ser Gly Cys Arg Val Cys Thr Arg Glu
        435                 440                 445

Asn Cys Ala Gln Arg Ala Phe Pro Ser Val His Gly Arg Ile Asn Ile
    450                 455                 460

Asp Ala His Glu Ser Thr Ile Ala Pro Tyr
465                 470
```

<210> SEQ ID NO 44
<211> LENGTH: 20
<212> TYPE: DNA
<213> ORGANISM: Artificial sequence
<220> FEATURE:
<223> OTHER INFORMATION: primer

<400> SEQUENCE: 44
aatagagcgg gtcatacacc                                              20

<210> SEQ ID NO 45
<211> LENGTH: 44
<212> TYPE: DNA
<213> ORGANISM: Artificial sequence
<220> FEATURE:
<223> OTHER INFORMATION: primer

<400> SEQUENCE: 45
ctctaaaaca ggaagagccc cttaaatagt gacagcaaga gcag                   44

<210> SEQ ID NO 46
<211> LENGTH: 47
<212> TYPE: DNA
<213> ORGANISM: Artificial sequence
<220> FEATURE:
<223> OTHER INFORMATION: primer

<400> SEQUENCE: 46
gcgctgctct tgctgtcact atttaagggg ctcttcctgt tttagag                47

<210> SEQ ID NO 47
<211> LENGTH: 40
<212> TYPE: DNA
<213> ORGANISM: Artificial sequence
<220> FEATURE:
<223> OTHER INFORMATION: primer

<400> SEQUENCE: 47
ccacagtcat gaccttaaat ggcccttccg gttttggggt                        40

<210> SEQ ID NO 48
<211> LENGTH: 40
<212> TYPE: DNA
<213> ORGANISM: Artificial sequence
<220> FEATURE:
<223> OTHER INFORMATION: primer

<400> SEQUENCE: 48
accccaaaac cggaagggcc atttaaggtc atgactgtgg                        40

<210> SEQ ID NO 49
<211> LENGTH: 20
<212> TYPE: DNA
<213> ORGANISM: Artificial sequence
<220> FEATURE:
<223> OTHER INFORMATION: primer

<400> SEQUENCE: 49
gtggatgatt ttagaaccca                                              20

<210> SEQ ID NO 50
<211> LENGTH: 28
<212> TYPE: DNA
<213> ORGANISM: Artificial sequence
<220> FEATURE:
<223> OTHER INFORMATION: primer -continued

<400> SEQUENCE: 50
gggagctcga ctttctggct cctttact                                28

<210> SEQ ID NO 51
<211> LENGTH: 28
<212> TYPE: DNA
<213> ORGANISM: Artificial sequence
<220> FEATURE:
<223> OTHER INFORMATION: primer

<400> SEQUENCE: 51
gggagctcgc cgatgactaa taatgaga                                28

<210> SEQ ID NO 52
<211> LENGTH: 2367
<212> TYPE: DNA
<213> ORGANISM: Lactobacillus pentosus
<220> FEATURE:
<221> NAME/KEY: CDS
<222> LOCATION: (1)..(2367)

<400> SEQUENCE: 52

```
atg tct aca gat tac tca tca cca gca tat ttg caa aaa gtt gat aag      48
Met Ser Thr Asp Tyr Ser Ser Pro Ala Tyr Leu Gln Lys Val Asp Lys
1               5                   10                  15 tac tgg cgt gct gcc aac tat tta tca gtt ggt caa ctt tat tta aaa      96
Tyr Trp Arg Ala Ala Asn Tyr Leu Ser Val Gly Gln Leu Tyr Leu Lys
            20                  25                  30 gat aat cct tta tta caa cgg cca tta aag gct agt gac gtt aag gtt     144
Asp Asn Pro Leu Leu Gln Arg Pro Leu Lys Ala Ser Asp Val Lys Val
        35                  40                  45 cac cca atc ggt cac tgg ggc acg att gcc ggc caa aac ttc atc tat     192
His Pro Ile Gly His Trp Gly Thr Ile Ala Gly Gln Asn Phe Ile Tyr
    50                  55                  60 gcg cat ctt aac cgg gtc atc aac aag tac ggt ttg aag atg ttc tac     240
Ala His Leu Asn Arg Val Ile Asn Lys Tyr Gly Leu Lys Met Phe Tyr
65                  70                  75                  80 gtt gaa ggt cca ggt cat ggt ggc caa gtg atg gtc tcc aac tca tac     288
Val Glu Gly Pro Gly His Gly Gly Gln Val Met Val Ser Asn Ser Tyr
                85                  90                  95 ctt gat ggg act tac acg gat att tat cct gaa att acg cag gat gtt     336
Leu Asp Gly Thr Tyr Thr Asp Ile Tyr Pro Glu Ile Thr Gln Asp Val
            100                 105                 110 gaa ggg atg caa aaa ctc ttc aag caa ttc tca ttc cca ggt ggc gtg     384
Glu Gly Met Gln Lys Leu Phe Lys Gln Phe Ser Phe Pro Gly Gly Val
        115                 120                 125 gct tcc cat gct gct cct gaa aca cca ggc tca atc cac gaa ggt ggc     432
Ala Ser His Ala Ala Pro Glu Thr Pro Gly Ser Ile His Glu Gly Gly
    130                 135                 140 gaa ctt ggt tac tca att tca cac ggt gtt ggg gca atc ctt gac aac     480
Glu Leu Gly Tyr Ser Ile Ser His Gly Val Gly Ala Ile Leu Asp Asn
145                 150                 155                 160 cct gat gaa atc gcc gca gtc gtt gtt ggt gat ggg gaa tcc gaa acc     528
Pro Asp Glu Ile Ala Ala Val Val Val Gly Asp Gly Glu Ser Glu Thr
                165                 170                 175 ggc cca tta gca act tca tgg caa tca acg aag ttc atc aac cca atc     576
Gly Pro Leu Ala Thr Ser Trp Gln Ser Thr Lys Phe Ile Asn Pro Ile
            180                 185                 190 aac gat ggg gca gtg tta cca atc ttg aac ctt aac ggc ttt aag att     624
Asn Asp Gly Ala Val Leu Pro Ile Leu Asn Leu Asn Gly Phe Lys Ile
        195                 200                 205
```

```
                                                            -continued
tct aac cca acg att ttt ggt cgg act tct gat gaa aag atc aag caa          672
Ser Asn Pro Thr Ile Phe Gly Arg Thr Ser Asp Glu Lys Ile Lys Gln
    210                 215                 220 tac ttc gaa agc atg aac tgg gaa cca atc ttt gtt gaa ggt gac gat          720
Tyr Phe Glu Ser Met Asn Trp Glu Pro Ile Phe Val Glu Gly Asp Asp
225                 230                 235                 240 cct gaa aag gtt cac cca gct tta gct aag gcc atg gat gaa gcc gtc          768
Pro Glu Lys Val His Pro Ala Leu Ala Lys Ala Met Asp Glu Ala Val
                245                 250                 255 gaa aag atc aaa gcc att caa aag aac gct cgt gaa aac gat gac gct          816
Glu Lys Ile Lys Ala Ile Gln Lys Asn Ala Arg Glu Asn Asp Asp Ala
            260                 265                 270 act tta cca gta tgg ccg atg atc gtc ttc cgc gca cct aag ggc tgg          864
Thr Leu Pro Val Trp Pro Met Ile Val Phe Arg Ala Pro Lys Gly Trp
        275                 280                 285 act ggt cct aag tca tgg gat ggc gac aag atc gaa ggt tca ttc cga          912
Thr Gly Pro Lys Ser Trp Asp Gly Asp Lys Ile Glu Gly Ser Phe Arg
    290                 295                 300 gct cac caa att cca att cct gtt gac caa acc gac atg gaa cat gcc          960
Ala His Gln Ile Pro Ile Pro Val Asp Gln Thr Asp Met Glu His Ala
305                 310                 315                 320 gat gcg tta gtt gac tgg ttg gaa tca tat caa cca aag gaa ctc ttc         1008
Asp Ala Leu Val Asp Trp Leu Glu Ser Tyr Gln Pro Lys Glu Leu Phe
                325                 330                 335 aat gaa gat ggt tct ttg aag gat gat atc aaa gaa att atc cca act         1056
Asn Glu Asp Gly Ser Leu Lys Asp Asp Ile Lys Glu Ile Ile Pro Thr
            340                 345                 350 ggc gat gca cgg atg gcc gct aac cca atc act aat ggt ggg gtt gat         1104
Gly Asp Ala Arg Met Ala Ala Asn Pro Ile Thr Asn Gly Gly Val Asp
        355                 360                 365 cca aag gcc ttg aac tta cct aac ttc cgt gat tac gcc gtt gat acg         1152
Pro Lys Ala Leu Asn Leu Pro Asn Phe Arg Asp Tyr Ala Val Asp Thr
    370                 375                 380 tct aag cat ggt gcc aac gtt aag caa gat atg atc gtt tgg tca gac         1200
Ser Lys His Gly Ala Asn Val Lys Gln Asp Met Ile Val Trp Ser Asp
385                 390                 395                 400 tac ttg cgt gat gtt atc aag aag aac cca gat aac ttc cgg tta ttt         1248
Tyr Leu Arg Asp Val Ile Lys Lys Asn Pro Asp Asn Phe Arg Leu Phe
                405                 410                 415 ggc cct gat gaa acc atg tca aac cgg tta tat ggt gtc ttt gaa acc         1296
Gly Pro Asp Glu Thr Met Ser Asn Arg Leu Tyr Gly Val Phe Glu Thr
            420                 425                 430 act aac cgt caa tgg atg gaa gat att cac cca gat agt gac caa tac         1344
Thr Asn Arg Gln Trp Met Glu Asp Ile His Pro Asp Ser Asp Gln Tyr
        435                 440                 445 gaa gca cct gct ggc cgg gtc ttg gat gct caa tta tct gaa cac caa         1392
Glu Ala Pro Ala Gly Arg Val Leu Asp Ala Gln Leu Ser Glu His Gln
    450                 455                 460 gct gaa ggt tgg tta gaa ggt tac gtc tta act ggt cgt cat ggc ttg         1440
Ala Glu Gly Trp Leu Glu Gly Tyr Val Leu Thr Gly Arg His Gly Leu
465                 470                 475                 480 ttt gca agt tac gaa gcc ttc tta cgg gtt gtc gac tca atg ttg acg         1488
Phe Ala Ser Tyr Glu Ala Phe Leu Arg Val Val Asp Ser Met Leu Thr
                485                 490                 495 caa cac ttc aag tgg tta cgt aag gcc aac gaa ctt gac tgg cgg aag         1536
Gln His Phe Lys Trp Leu Arg Lys Ala Asn Glu Leu Asp Trp Arg Lys
            500                 505                 510 aag tac ccg tca ctc aac att atc gcg gct tca act gtg ttc caa caa         1584
Lys Tyr Pro Ser Leu Asn Ile Ile Ala Ala Ser Thr Val Phe Gln Gln
        515                 520                 525
```

```
gac cat aat ggg tac acc cac caa gat cca ggt gcc ttg act cat ttg      1632
Asp His Asn Gly Tyr Thr His Gln Asp Pro Gly Ala Leu Thr His Leu
        530                 535                 540 gct gaa aag aag cct gaa tat atc cgc gaa tat tta cca gcc gac gcc      1680
Ala Glu Lys Lys Pro Glu Tyr Ile Arg Glu Tyr Leu Pro Ala Asp Ala
545                 550                 555                 560 aac tcc ttg tta gct gtt ggg gac gtc atc ttc cgt agc caa gaa aag      1728
Asn Ser Leu Leu Ala Val Gly Asp Val Ile Phe Arg Ser Gln Glu Lys
                565                 570                 575 atc aac tac gtg gtt acg tcg aag cac cca cgt caa caa tgg ttc agc      1776
Ile Asn Tyr Val Val Thr Ser Lys His Pro Arg Gln Gln Trp Phe Ser
            580                 585                 590 att gaa gaa gct aag caa tta gtt gac aac ggt ctt ggt atc att gac      1824
Ile Glu Glu Ala Lys Gln Leu Val Asp Asn Gly Leu Gly Ile Ile Asp
        595                 600                 605 tgg gca agc acg gac caa ggt agc gaa cca gat atc gtg ttt gct gct      1872
Trp Ala Ser Thr Asp Gln Gly Ser Glu Pro Asp Ile Val Phe Ala Ala
    610                 615                 620 gcc gga acg gaa cca acg ctt gaa acg ttg gct gca atc caa ttg ctc      1920
Ala Gly Thr Glu Pro Thr Leu Glu Thr Leu Ala Ala Ile Gln Leu Leu
625                 630                 635                 640 cat gat agc ttc cca gac atg aag att cgt ttc gtg aac gtg gtc gac      1968
His Asp Ser Phe Pro Asp Met Lys Ile Arg Phe Val Asn Val Val Asp
                645                 650                 655 atc ttg aag tta cgt agc cct gaa aag gac cct cgt ggc ttg tca gat      2016
Ile Leu Lys Leu Arg Ser Pro Glu Lys Asp Pro Arg Gly Leu Ser Asp
            660                 665                 670 gct gaa ttt gac cat tac ttc act aag gac aaa cca gtt gtc ttc gcc      2064
Ala Glu Phe Asp His Tyr Phe Thr Lys Asp Lys Pro Val Val Phe Ala
        675                 680                 685 ttc cat ggt tac gaa gac ctg gtt cgt gac atc ttc ttt gat cgt cac      2112
Phe His Gly Tyr Glu Asp Leu Val Arg Asp Ile Phe Phe Asp Arg His
    690                 695                 700 aac cac aac tta cac gtg cat ggc tac cgt gaa aat ggt gac att acg      2160
Asn His Asn Leu His Val His Gly Tyr Arg Glu Asn Gly Asp Ile Thr
705                 710                 715                 720 aca cca ttc gat gtc cgg gtc atg aac caa atg gac cgt ttc gac tta      2208
Thr Pro Phe Asp Val Arg Val Met Asn Gln Met Asp Arg Phe Asp Leu
                725                 730                 735 gca aaa tct gca att gcg gcg caa cca gca atg gaa aac acc ggt gca      2256
Ala Lys Ser Ala Ile Ala Ala Gln Pro Ala Met Glu Asn Thr Gly Ala
            740                 745                 750 gcc ttt gtt caa gac atg gat aac atg ctt gca aaa cac aac gca tac      2304
Ala Phe Val Gln Asp Met Asp Asn Met Leu Ala Lys His Asn Ala Tyr
        755                 760                 765 atc cgt gac gcc gga acc gac ttg cca gaa gtt aac gac tgg caa tgg      2352
Ile Arg Asp Ala Gly Thr Asp Leu Pro Glu Val Asn Asp Trp Gln Trp
    770                 775                 780 aaa ggt ttg aaa taa                                                  2367
Lys Gly Leu Lys
785

<210> SEQ ID NO 53
<211> LENGTH: 788
<212> TYPE: PRT
<213> ORGANISM: Lactobacillus pentosus

<400> SEQUENCE: 53

Met Ser Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
```

-continued

```
                    20                  25                  30
Asp Asn Pro Leu Leu Gln Arg Pro Leu Lys Ala Ser Asp Val Lys Val
                    35                  40                  45

His Pro Ile Gly His Trp Gly Thr Ile Ala Gly Gln Asn Phe Ile Tyr
                    50                  55                  60

Ala His Leu Asn Arg Val Ile Asn Lys Tyr Gly Leu Lys Met Phe Tyr
 65                  70                  75                  80

Val Glu Gly Pro Gly His Gly Gly Gln Val Met Val Ser Asn Ser Tyr
                    85                  90                  95

Leu Asp Gly Thr Tyr Thr Asp Ile Tyr Pro Glu Ile Thr Gln Asp Val
                    100                 105                 110

Glu Gly Met Gln Lys Leu Phe Lys Gln Phe Ser Phe Pro Gly Gly Val
                    115                 120                 125

Ala Ser His Ala Ala Pro Glu Thr Pro Gly Ser Ile His Glu Gly Gly
                    130                 135                 140

Glu Leu Gly Tyr Ser Ile Ser His Gly Val Gly Ala Ile Leu Asp Asn
145                 150                 155                 160

Pro Asp Glu Ile Ala Ala Val Val Gly Asp Gly Glu Ser Glu Thr
                    165                 170                 175

Gly Pro Leu Ala Thr Ser Trp Gln Ser Thr Lys Phe Ile Asn Pro Ile
                    180                 185                 190

Asn Asp Gly Ala Val Leu Pro Ile Leu Asn Leu Asn Gly Phe Lys Ile
                    195                 200                 205

Ser Asn Pro Thr Ile Phe Gly Arg Thr Ser Asp Glu Lys Ile Lys Gln
                    210                 215                 220

Tyr Phe Glu Ser Met Asn Trp Glu Pro Ile Phe Val Glu Gly Asp Asp
225                 230                 235                 240

Pro Glu Lys Val His Pro Ala Leu Ala Lys Ala Met Asp Glu Ala Val
                    245                 250                 255

Glu Lys Ile Lys Ala Ile Gln Lys Asn Ala Arg Glu Asn Asp Asp Ala
                    260                 265                 270

Thr Leu Pro Val Trp Pro Met Ile Val Phe Arg Ala Pro Lys Gly Trp
                    275                 280                 285

Thr Gly Pro Lys Ser Trp Asp Gly Asp Lys Ile Glu Gly Ser Phe Arg
                    290                 295                 300

Ala His Gln Ile Pro Ile Pro Val Asp Gln Thr Asp Met Glu His Ala
305                 310                 315                 320

Asp Ala Leu Val Asp Trp Leu Glu Ser Tyr Gln Pro Lys Glu Leu Phe
                    325                 330                 335

Asn Glu Asp Gly Ser Leu Lys Asp Asp Ile Lys Glu Ile Ile Pro Thr
                    340                 345                 350

Gly Asp Ala Arg Met Ala Ala Asn Pro Ile Thr Asn Gly Gly Val Asp
                    355                 360                 365

Pro Lys Ala Leu Asn Leu Pro Asn Phe Arg Asp Tyr Ala Val Asp Thr
                    370                 375                 380

Ser Lys His Gly Ala Asn Val Lys Gln Asp Met Ile Val Trp Ser Asp
385                 390                 395                 400

Tyr Leu Arg Asp Val Ile Lys Lys Asn Pro Asp Asn Phe Arg Leu Phe
                    405                 410                 415

Gly Pro Asp Glu Thr Met Ser Asn Arg Leu Tyr Gly Val Phe Glu Thr
                    420                 425                 430

Thr Asn Arg Gln Trp Met Glu Asp Ile His Pro Asp Ser Asp Gln Tyr
                    435                 440                 445
```

Glu Ala Pro Ala Gly Arg Val Leu Asp Ala Gln Leu Ser Glu His Gln
450                 455                 460

Ala Glu Gly Trp Leu Glu Gly Tyr Val Leu Thr Gly Arg His Gly Leu
465                 470                 475                 480

Phe Ala Ser Tyr Glu Ala Phe Leu Arg Val Val Asp Ser Met Leu Thr
                485                 490                 495

Gln His Phe Lys Trp Leu Arg Lys Ala Asn Glu Leu Asp Trp Arg Lys
                500                 505                 510

Lys Tyr Pro Ser Leu Asn Ile Ile Ala Ala Ser Thr Val Phe Gln Gln
            515                 520                 525

Asp His Asn Gly Tyr Thr His Gln Asp Pro Gly Ala Leu Thr His Leu
530                 535                 540

Ala Glu Lys Lys Pro Glu Tyr Ile Arg Glu Tyr Leu Pro Ala Asp Ala
545                 550                 555                 560

Asn Ser Leu Leu Ala Val Gly Asp Val Ile Phe Arg Ser Gln Glu Lys
                565                 570                 575

Ile Asn Tyr Val Val Thr Ser Lys His Pro Arg Gln Gln Trp Phe Ser
                580                 585                 590

Ile Glu Glu Ala Lys Gln Leu Val Asp Asn Gly Leu Gly Ile Ile Asp
            595                 600                 605

Trp Ala Ser Thr Asp Gln Gly Ser Glu Pro Asp Ile Val Phe Ala Ala
610                 615                 620

Ala Gly Thr Glu Pro Thr Leu Glu Thr Leu Ala Ala Ile Gln Leu Leu
625                 630                 635                 640

His Asp Ser Phe Pro Asp Met Lys Ile Arg Phe Val Asn Val Val Asp
                645                 650                 655

Ile Leu Lys Leu Arg Ser Pro Glu Lys Asp Pro Arg Gly Leu Ser Asp
                660                 665                 670

Ala Glu Phe Asp His Tyr Phe Thr Lys Asp Lys Pro Val Val Phe Ala
            675                 680                 685

Phe His Gly Tyr Glu Asp Leu Val Arg Asp Ile Phe Phe Asp Arg His
690                 695                 700

Asn His Asn Leu His Val His Gly Tyr Arg Glu Asn Gly Asp Ile Thr
705                 710                 715                 720

Thr Pro Phe Asp Val Arg Val Met Asn Gln Met Asp Arg Phe Asp Leu
                725                 730                 735

Ala Lys Ser Ala Ile Ala Ala Gln Pro Ala Met Glu Asn Thr Gly Ala
                740                 745                 750

Ala Phe Val Gln Asp Met Asp Asn Met Leu Ala Lys His Asn Ala Tyr
            755                 760                 765

Ile Arg Asp Ala Gly Thr Asp Leu Pro Glu Val Asn Asp Trp Gln Trp
770                 775                 780

Lys Gly Leu Lys
785

<210> SEQ ID NO 54
<211> LENGTH: 2367
<212> TYPE: DNA
<213> ORGANISM: Lactobacillus plantarum
<220> FEATURE:
<221> NAME/KEY: CDS
<222> LOCATION: (1)..(2367)

<400> SEQUENCE: 54 atg aca aca gat tac tca tca cca gca tat ttg caa aaa gtt gat aag       48
Met Thr Thr Asp Tyr Ser Ser Pro Ala Tyr Leu Gln Lys Val Asp Lys
1               5                   10                  15

| | | |
|---|---|---|
| tac tgg cgt gct gcc aac tac tta tca gtt ggt caa ctt tat tta aaa<br>Tyr Trp Arg Ala Ala Asn Tyr Leu Ser Val Gly Gln Leu Tyr Leu Lys<br>20 25 30 | | 96 |
| gat aat cca cta tta caa cgg cca ttg aag gcc agt gac gtt aag gtt<br>Asp Asn Pro Leu Leu Gln Arg Pro Leu Lys Ala Ser Asp Val Lys Val<br>35 40 45 | | 144 |
| cat cca att ggt cac tgg ggg acg att gcc ggt caa aac ttt atc tat<br>His Pro Ile Gly His Trp Gly Thr Ile Ala Gly Gln Asn Phe Ile Tyr<br>50 55 60 | | 192 |
| gct cat ctt aac cgg gtc atc aac aag tac ggt ttg aag atg ttc tac<br>Ala His Leu Asn Arg Val Ile Asn Lys Tyr Gly Leu Lys Met Phe Tyr<br>65 70 75 80 | | 240 |
| gtt gaa ggt cca ggt cat ggt ggt caa gtg atg gtt tca aac tct tac<br>Val Glu Gly Pro Gly His Gly Gly Gln Val Met Val Ser Asn Ser Tyr<br>85 90 95 | | 288 |
| ctt gac ggt act tac acc gat att tat cca gaa att acg cag gat gtt<br>Leu Asp Gly Thr Tyr Thr Asp Ile Tyr Pro Glu Ile Thr Gln Asp Val<br>100 105 110 | | 336 |
| gaa ggg atg caa aag ctc ttc aag caa ttc tca ttc cca ggt ggg gtt<br>Glu Gly Met Gln Lys Leu Phe Lys Gln Phe Ser Phe Pro Gly Gly Val<br>115 120 125 | | 384 |
| gct tcc cat gcg gca cct gaa aca ccc ggt tca atc cac gaa ggt ggc<br>Ala Ser His Ala Ala Pro Glu Thr Pro Gly Ser Ile His Glu Gly Gly<br>130 135 140 | | 432 |
| gaa ctt ggt tac tca att tca cac ggg gtt ggg gca att ctt gac aat<br>Glu Leu Gly Tyr Ser Ile Ser His Gly Val Gly Ala Ile Leu Asp Asn<br>145 150 155 160 | | 480 |
| cct gac gaa atc gcc gcg gtt gtt gtt ggt gat ggg gaa tcc gaa acg<br>Pro Asp Glu Ile Ala Ala Val Val Val Gly Asp Gly Glu Ser Glu Thr<br>165 170 175 | | 528 |
| ggt cca tta gca act tca tgg caa tca acg aag ttc att aac cca atc<br>Gly Pro Leu Ala Thr Ser Trp Gln Ser Thr Lys Phe Ile Asn Pro Ile<br>180 185 190 | | 576 |
| aac gac ggg gct gtt tta cca atc ttg aac tta aat ggt ttt aag att<br>Asn Asp Gly Ala Val Leu Pro Ile Leu Asn Leu Asn Gly Phe Lys Ile<br>195 200 205 | | 624 |
| tct aat cca acg att ttt ggt cgg act tct gat gct aag att aag gaa<br>Ser Asn Pro Thr Ile Phe Gly Arg Thr Ser Asp Ala Lys Ile Lys Glu<br>210 215 220 | | 672 |
| tac ttc gaa agc atg aat tgg gaa cca atc ttc gtt gaa ggt gac gat<br>Tyr Phe Glu Ser Met Asn Trp Glu Pro Ile Phe Val Glu Gly Asp Asp<br>225 230 235 240 | | 720 |
| cct gaa aag gtt cac cca gcc tta gct aag gcc atg gat gaa gcc gtt<br>Pro Glu Lys Val His Pro Ala Leu Ala Lys Ala Met Asp Glu Ala Val<br>245 250 255 | | 768 |
| gaa aag atc aag gca atc cag aag cat gct cgc gaa aat aac gat gca<br>Glu Lys Ile Lys Ala Ile Gln Lys His Ala Arg Glu Asn Asn Asp Ala<br>260 265 270 | | 816 |
| aca ttg cca gta tgg cca atg atc gtc ttc cgc gca cct aag ggc tgg<br>Thr Leu Pro Val Trp Pro Met Ile Val Phe Arg Ala Pro Lys Gly Trp<br>275 280 285 | | 864 |
| act ggt ccg aag tca tgg gac ggt gat aag atc gaa ggt tca ttc cgt<br>Thr Gly Pro Lys Ser Trp Asp Gly Asp Lys Ile Glu Gly Ser Phe Arg<br>290 295 300 | | 912 |
| gct cat caa att ccg att cct gtt gat caa aat gac atg gaa cat gcg<br>Ala His Gln Ile Pro Ile Pro Val Asp Gln Asn Asp Met Glu His Ala<br>305 310 315 320 | | 960 |
| gat gct tta gtt gat tgg ctc gaa tca tat caa cca aaa gaa ctc ttc<br>Asp Ala Leu Val Asp Trp Leu Glu Ser Tyr Gln Pro Lys Glu Leu Phe<br>325 330 335 | | 1008 |

-continued

```
aat gaa gat ggc tct ttg aag gat gat att aaa gaa att att cct act      1056
Asn Glu Asp Gly Ser Leu Lys Asp Asp Ile Lys Glu Ile Ile Pro Thr
            340                 345                 350 ggg gac agt cgg atg gct gct aac cca atc acc aat ggt ggg gtc gat      1104
Gly Asp Ser Arg Met Ala Ala Asn Pro Ile Thr Asn Gly Gly Val Asp
355                 360                 365 ccg aaa gcc ttg aac tta cca aac ttc cgt gat tat gcg gtc gat acg      1152
Pro Lys Ala Leu Asn Leu Pro Asn Phe Arg Asp Tyr Ala Val Asp Thr
    370                 375                 380 tcc aaa gaa ggc gcg aat gtt aag caa gat atg atc gtt tgg tca gac      1200
Ser Lys Glu Gly Ala Asn Val Lys Gln Asp Met Ile Val Trp Ser Asp
385                 390                 395                 400 tat ttg cgg gat gtc atc aag aaa aat cct gat aac ttc cgg ttg ttc      1248
Tyr Leu Arg Asp Val Ile Lys Lys Asn Pro Asp Asn Phe Arg Leu Phe
                405                 410                 415 gga cct gat gaa acc atg tct aac cgt tta tat ggt gtc ttc gaa acc      1296
Gly Pro Asp Glu Thr Met Ser Asn Arg Leu Tyr Gly Val Phe Glu Thr
            420                 425                 430 act aat cgt caa tgg atg gaa gac att cat cca gat agt gac caa tat      1344
Thr Asn Arg Gln Trp Met Glu Asp Ile His Pro Asp Ser Asp Gln Tyr
        435                 440                 445 gaa gca cca gct ggc cgg gtc tta gat gct cag tta tct gaa cac caa      1392
Glu Ala Pro Ala Gly Arg Val Leu Asp Ala Gln Leu Ser Glu His Gln
450                 455                 460 gct gaa ggt tgg tta gaa ggt tac gtc tta act gga cgt cat ggg tta      1440
Ala Glu Gly Trp Leu Glu Gly Tyr Val Leu Thr Gly Arg His Gly Leu
465                 470                 475                 480 ttt gcc agt tat gaa gcc ttc cta cgc gtt gtg gac tca atg ttg acg      1488
Phe Ala Ser Tyr Glu Ala Phe Leu Arg Val Val Asp Ser Met Leu Thr
                485                 490                 495 caa cac ttc aag tgg tta cgt aaa gcc aat gaa ctt gat tgg cgt aaa      1536
Gln His Phe Lys Trp Leu Arg Lys Ala Asn Glu Leu Asp Trp Arg Lys
            500                 505                 510 aag tac cca tca ctt aac att atc gcg gct tca act gta ttc caa caa      1584
Lys Tyr Pro Ser Leu Asn Ile Ile Ala Ala Ser Thr Val Phe Gln Gln
        515                 520                 525 gac cat aat ggt tat acc cac caa gat cca ggt gca tta act cat ttg      1632
Asp His Asn Gly Tyr Thr His Gln Asp Pro Gly Ala Leu Thr His Leu
530                 535                 540 gcc gaa aag aaa cca gaa tac att cgt gaa tat tta cca gcc gat gcc      1680
Ala Glu Lys Lys Pro Glu Tyr Ile Arg Glu Tyr Leu Pro Ala Asp Ala
545                 550                 555                 560 aac acg tta tta gct gtc ggt gac gtc att ttc cgg agc caa gaa aag      1728
Asn Thr Leu Leu Ala Val Gly Asp Val Ile Phe Arg Ser Gln Glu Lys
                565                 570                 575 atc aac tac gtg gtt acg tca aaa cac cca cgt caa caa tgg ttc agc      1776
Ile Asn Tyr Val Val Thr Ser Lys His Pro Arg Gln Gln Trp Phe Ser
            580                 585                 590 att gaa gaa gct aag caa tta gtt gac aat ggt ctt ggt atc att gat      1824
Ile Glu Glu Ala Lys Gln Leu Val Asp Asn Gly Leu Gly Ile Ile Asp
        595                 600                 605 tgg gca agt acg gac caa ggt agc gaa cca gac att gtc ttt gca gct      1872
Trp Ala Ser Thr Asp Gln Gly Ser Glu Pro Asp Ile Val Phe Ala Ala
610                 615                 620 gct ggg acg gaa cca acg ctt gaa acg ttg gct gcc atc caa tta cta      1920
Ala Gly Thr Glu Pro Thr Leu Glu Thr Leu Ala Ala Ile Gln Leu Leu
625                 630                 635                 640 cac gac agt ttc cca gag atg aag att cgt ttc gtg aac gtg gtc gac      1968
His Asp Ser Phe Pro Glu Met Lys Ile Arg Phe Val Asn Val Val Asp
                645                 650                 655
```

-continued

```
atc ttg aag tta cgt agt cct gaa aag gat ccg cgg ggc ttg tca gat    2016
Ile Leu Lys Leu Arg Ser Pro Glu Lys Asp Pro Arg Gly Leu Ser Asp
        660                 665                 670 gct gag ttt gac cat tac ttt act aag gac aaa cca gtg gtc ttt gct    2064
Ala Glu Phe Asp His Tyr Phe Thr Lys Asp Lys Pro Val Val Phe Ala
        675                 680                 685 ttc cac ggt tac gaa gac tta gtt cgt gac atc ttc ttt gat cgt cac    2112
Phe His Gly Tyr Glu Asp Leu Val Arg Asp Ile Phe Phe Asp Arg His
        690                 695                 700 aac cat aac tta tac gtc cac ggt tac cgt gaa aat ggt gat att acc    2160
Asn His Asn Leu Tyr Val His Gly Tyr Arg Glu Asn Gly Asp Ile Thr
705                 710                 715                 720 aca cca ttc gac gta cgg gtc atg aac cag atg gac cgc ttc gac tta    2208
Thr Pro Phe Asp Val Arg Val Met Asn Gln Met Asp Arg Phe Asp Leu
                725                 730                 735 gct aag tcg gca att gcg gcg caa cca gca atg gaa aac act ggt gcg    2256
Ala Lys Ser Ala Ile Ala Ala Gln Pro Ala Met Glu Asn Thr Gly Ala
        740                 745                 750 gcc ttc gtt caa tcc atg gat aat atg ctt gct aaa cac aat gcc tat    2304
Ala Phe Val Gln Ser Met Asp Asn Met Leu Ala Lys His Asn Ala Tyr
        755                 760                 765 atc cgg gat gcc gga act gac ttg cca gaa gtt aat gat tgg caa tgg    2352
Ile Arg Asp Ala Gly Thr Asp Leu Pro Glu Val Asn Asp Trp Gln Trp
        770                 775                 780 aag ggt tta aaa taa                                                 2367
Lys Gly Leu Lys
785

<210> SEQ ID NO 55
<211> LENGTH: 788
<212> TYPE: PRT
<213> ORGANISM: Lactobacillus plantarum

<400> SEQUENCE: 55

Met Thr Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
            20                  25                  30

Asp Asn Pro Leu Leu Gln Arg Pro Leu Lys Ala Ser Asp Val Lys Val
        35                  40                  45

His Pro Ile Gly His Trp Gly Thr Ile Ala Gly Gln Asn Phe Ile Tyr
    50                  55                  60

Ala His Leu Asn Arg Val Ile Asn Lys Tyr Gly Leu Lys Met Phe Tyr
65                  70                  75                  80

Val Glu Gly Pro Gly His Gly Gln Val Met Val Ser Asn Ser Tyr
            85                  90                  95

Leu Asp Gly Thr Tyr Thr Asp Ile Tyr Pro Glu Ile Thr Gln Asp Val
            100                 105                 110

Glu Gly Met Gln Lys Leu Phe Lys Gln Phe Ser Phe Pro Gly Gly Val
        115                 120                 125

Ala Ser His Ala Ala Pro Glu Thr Pro Gly Ser Ile His Glu Gly Gly
    130                 135                 140

Glu Leu Gly Tyr Ser Ile Ser His Gly Val Gly Ala Ile Leu Asp Asn
145                 150                 155                 160

Pro Asp Glu Ile Ala Ala Val Val Gly Asp Gly Glu Ser Glu Thr
                165                 170                 175

Gly Pro Leu Ala Thr Ser Trp Gln Ser Thr Lys Phe Ile Asn Pro Ile
            180                 185                 190
```

```
Asn Asp Gly Ala Val Leu Pro Ile Leu Asn Leu Asn Gly Phe Lys Ile
            195                 200                 205

Ser Asn Pro Thr Ile Phe Gly Arg Thr Ser Asp Ala Lys Ile Lys Glu
210                 215                 220

Tyr Phe Glu Ser Met Asn Trp Glu Pro Ile Phe Val Glu Gly Asp Asp
225                 230                 235                 240

Pro Glu Lys Val His Pro Ala Leu Ala Lys Ala Met Asp Glu Ala Val
                245                 250                 255

Glu Lys Ile Lys Ala Ile Gln Lys His Ala Arg Glu Asn Asn Asp Ala
            260                 265                 270

Thr Leu Pro Val Trp Pro Met Ile Val Phe Arg Ala Pro Lys Gly Trp
        275                 280                 285

Thr Gly Pro Lys Ser Trp Asp Gly Asp Lys Ile Glu Gly Ser Phe Arg
    290                 295                 300

Ala His Gln Ile Pro Ile Pro Val Asp Gln Asn Asp Met Glu His Ala
305                 310                 315                 320

Asp Ala Leu Val Asp Trp Leu Glu Ser Tyr Gln Pro Lys Glu Leu Phe
                325                 330                 335

Asn Glu Asp Gly Ser Leu Lys Asp Asp Ile Lys Glu Ile Ile Pro Thr
            340                 345                 350

Gly Asp Ser Arg Met Ala Ala Asn Pro Ile Thr Asn Gly Gly Val Asp
        355                 360                 365

Pro Lys Ala Leu Asn Leu Pro Asn Phe Arg Asp Tyr Ala Val Asp Thr
    370                 375                 380

Ser Lys Glu Gly Ala Asn Val Lys Gln Asp Met Ile Val Trp Ser Asp
385                 390                 395                 400

Tyr Leu Arg Asp Val Ile Lys Lys Asn Pro Asp Asn Phe Arg Leu Phe
                405                 410                 415

Gly Pro Asp Glu Thr Met Ser Asn Arg Leu Tyr Gly Val Phe Glu Thr
            420                 425                 430

Thr Asn Arg Gln Trp Met Glu Asp Ile His Pro Asp Ser Asp Gln Tyr
        435                 440                 445

Glu Ala Pro Ala Gly Arg Val Leu Asp Ala Gln Leu Ser Glu His Gln
    450                 455                 460

Ala Glu Gly Trp Leu Glu Gly Tyr Val Leu Thr Gly Arg His Gly Leu
465                 470                 475                 480

Phe Ala Ser Tyr Glu Ala Phe Leu Arg Val Val Asp Ser Met Leu Thr
                485                 490                 495

Gln His Phe Lys Trp Leu Arg Lys Ala Asn Glu Leu Asp Trp Arg Lys
            500                 505                 510

Lys Tyr Pro Ser Leu Asn Ile Ile Ala Ala Ser Thr Val Phe Gln Gln
        515                 520                 525

Asp His Asn Gly Tyr Thr His Gln Asp Pro Gly Ala Leu Thr His Leu
    530                 535                 540

Ala Glu Lys Lys Pro Glu Tyr Ile Arg Glu Tyr Leu Pro Ala Asp Ala
545                 550                 555                 560

Asn Thr Leu Leu Ala Val Gly Asp Val Ile Phe Arg Ser Gln Glu Lys
                565                 570                 575

Ile Asn Tyr Val Val Thr Ser Lys His Pro Arg Gln Gln Trp Phe Ser
            580                 585                 590

Ile Glu Glu Ala Lys Gln Leu Val Asp Asn Gly Leu Gly Ile Ile Asp
        595                 600                 605

Trp Ala Ser Thr Asp Gln Gly Ser Glu Pro Asp Ile Val Phe Ala Ala
```

```
                610             615             620
Ala Gly Thr Glu Pro Thr Leu Glu Thr Leu Ala Ala Ile Gln Leu Leu
625                 630                 635                 640

His Asp Ser Phe Pro Glu Met Lys Ile Arg Phe Val Asn Val Val Asp
                645                 650                 655

Ile Leu Lys Leu Arg Ser Pro Glu Lys Asp Pro Arg Gly Leu Ser Asp
                    660                 665                 670

Ala Glu Phe Asp His Tyr Phe Thr Lys Asp Lys Pro Val Val Phe Ala
                675                 680                 685

Phe His Gly Tyr Glu Asp Leu Val Arg Asp Ile Phe Phe Asp Arg His
                690                 695                 700

Asn His Asn Leu Tyr Val His Gly Tyr Arg Glu Asn Gly Asp Ile Thr
705                 710                 715                 720

Thr Pro Phe Asp Val Arg Val Met Asn Gln Met Asp Arg Phe Asp Leu
                    725                 730                 735

Ala Lys Ser Ala Ile Ala Ala Gln Pro Ala Met Glu Asn Thr Gly Ala
                740                 745                 750

Ala Phe Val Gln Ser Met Asp Asn Met Leu Ala Lys His Asn Ala Tyr
                755                 760                 765

Ile Arg Asp Ala Gly Thr Asp Leu Pro Glu Val Asn Asp Trp Gln Trp
770                 775                 780

Lys Gly Leu Lys
785

<210> SEQ ID NO 56
<211> LENGTH: 2660
<212> TYPE: DNA
<213> ORGANISM: Bifidobacterium lactis
<220> FEATURE:
<221> NAME/KEY: CDS
<222> LOCATION: (128)..(2605)

<400> SEQUENCE: 56
aggtcagcgt attcgcgtaa cataatcagc gatcgggcac ggagaccggc ctgcaggaca      60
gcgccgaagc ccgtgcccaa cggaataaac aaatcgcaca tttatgtgca ggagtacagg     120 agcacac atg act aat cct gtt att ggt acc cca tgg cag aag ctg gat       169
        Met Thr Asn Pro Val Ile Gly Thr Pro Trp Gln Lys Leu Asp
        1               5                   10 cgt ccg gtt tcc gaa gag gcc atc gaa ggc atg gac aag tac tgg cgc       217
Arg Pro Val Ser Glu Glu Ala Ile Glu Gly Met Asp Lys Tyr Trp Arg
15                  20                  25                  30 gtc gcc aac tac atg tct atc ggc cag atc tac ctg cgt agc aac ccg       265
Val Ala Asn Tyr Met Ser Ile Gly Gln Ile Tyr Leu Arg Ser Asn Pro
                35                  40                  45 ctg atg aag gag ccc ttc acc cgc gat gac gtg aag cac cgt ctg gtc       313
Leu Met Lys Glu Pro Phe Thr Arg Asp Asp Val Lys His Arg Leu Val
            50                  55                  60 ggc cac tgg ggc acc acc ccg ggc ctg aac ttc ctt ctc gcc cac atc       361
Gly His Trp Gly Thr Thr Pro Gly Leu Asn Phe Leu Leu Ala His Ile
        65                  70                  75 aac cgc ctg atc gcc gat cac cag cag aac acc gtg ttc atc atg ggt       409
Asn Arg Leu Ile Ala Asp His Gln Gln Asn Thr Val Phe Ile Met Gly
    80                  85                  90 cct ggc cac ggc ggc cct gca ggt acc gct cag tcc tac atc gac ggc       457
Pro Gly His Gly Gly Pro Ala Gly Thr Ala Gln Ser Tyr Ile Asp Gly
95                  100                 105                 110 acc tac acc gag tac tac ccg aac atc acc aag gac gaa gct ggc ctg       505
Thr Tyr Thr Glu Tyr Tyr Pro Asn Ile Thr Lys Asp Glu Ala Gly Leu
```

```
                    115                 120                 125
cag aag ttc ttc cgc cag ttc tcc tac ccg ggt ggc att cct tcc cac       553
Gln Lys Phe Phe Arg Gln Phe Ser Tyr Pro Gly Gly Ile Pro Ser His
            130                 135                 140 ttc gct ccg gag acg ccg ggc tcc atc cac gaa ggc ggc gag ctg ggc       601
Phe Ala Pro Glu Thr Pro Gly Ser Ile His Glu Gly Gly Glu Leu Gly
        145                 150                 155 tac gcc ctg tcg cac gcc tac ggc gcg atc atg gac aac ccg agc ctc       649
Tyr Ala Leu Ser His Ala Tyr Gly Ala Ile Met Asp Asn Pro Ser Leu
    160                 165                 170 ttc gtc ccg tgc atc atc ggt gac ggc gaa gcc gag acc ggc cct ctg       697
Phe Val Pro Cys Ile Ile Gly Asp Gly Glu Ala Glu Thr Gly Pro Leu
175                 180                 185                 190 gcc acc ggc tgg cag tcc aac aag ctc gtc aac ccg cgc acc gac ggc       745
Ala Thr Gly Trp Gln Ser Asn Lys Leu Val Asn Pro Arg Thr Asp Gly
                195                 200                 205 atc gtc ctg ccg atc ctg cac ctc aac ggc tac aag atc gcc aac ccg       793
Ile Val Leu Pro Ile Leu His Leu Asn Gly Tyr Lys Ile Ala Asn Pro
            210                 215                 220 acg atc ctc gcc cgc atc tcc gac gag gag ctg cac gac ttc ttc cgc       841
Thr Ile Leu Ala Arg Ile Ser Asp Glu Glu Leu His Asp Phe Phe Arg
        225                 230                 235 ggc atg ggt tac cac ccg tac gag ttc gtc gcc ggc ttc gac aac gag       889
Gly Met Gly Tyr His Pro Tyr Glu Phe Val Ala Gly Phe Asp Asn Glu
    240                 245                 250 gat cac ctg tcg atc cac cgt cgc ttc gcc gag ctc ttc gag acc atc       937
Asp His Leu Ser Ile His Arg Arg Phe Ala Glu Leu Phe Glu Thr Ile
255                 260                 265                 270 ttc gac gag atc tgc gat atc aag gct gcg gct cag acc gac gac atg       985
Phe Asp Glu Ile Cys Asp Ile Lys Ala Ala Ala Gln Thr Asp Asp Met
                275                 280                 285 acc cgt ccg ttc tac ccg atg ctc atc ttc cgc acc ccg aag ggc tgg      1033
Thr Arg Pro Phe Tyr Pro Met Leu Ile Phe Arg Thr Pro Lys Gly Trp
            290                 295                 300 acc tgc ccg aag ttc atc gac ggc aag aag acc gaa ggc tcc tgg cgt      1081
Thr Cys Pro Lys Phe Ile Asp Gly Lys Lys Thr Glu Gly Ser Trp Arg
        305                 310                 315 gca cac cag gtc ccg ctg gct tcc gcc cgc gac acc gag gcc cac ttc      1129
Ala His Gln Val Pro Leu Ala Ser Ala Arg Asp Thr Glu Ala His Phe
    320                 325                 330 gaa gtc ctc aag ggc tgg atg gaa tcc tac aag ccg gag gag ctc ttc      1177
Glu Val Leu Lys Gly Trp Met Glu Ser Tyr Lys Pro Glu Glu Leu Phe
335                 340                 345                 350 aac gcc gac ggc tcc atc aag gag gac gtc acc gca ttc atg cct aag      1225
Asn Ala Asp Gly Ser Ile Lys Glu Asp Val Thr Ala Phe Met Pro Lys
                355                 360                 365 ggc gaa ctg cgc atc ggc gcc aac ccg aat gcc aac ggc ggc cgc atc      1273
Gly Glu Leu Arg Ile Gly Ala Asn Pro Asn Ala Asn Gly Gly Arg Ile
            370                 375                 380 cgc gag gat ctg aag ctc cct gag ctc gat cag tac gag atc acc ggc      1321
Arg Glu Asp Leu Lys Leu Pro Glu Leu Asp Gln Tyr Glu Ile Thr Gly
        385                 390                 395 gtc aag gaa tac ggc cac ggt tgg ggc cag gtc gag gct ccg cgt tcc      1369
Val Lys Glu Tyr Gly His Gly Trp Gly Gln Val Glu Ala Pro Arg Ser
    400                 405                 410 ctc ggc gcg tac tgc cgc gac atc atc aag aac aac ccg gat tcg ttc      1417
Leu Gly Ala Tyr Cys Arg Asp Ile Ile Lys Asn Asn Pro Asp Ser Phe
415                 420                 425                 430 cgc gtc ttc gga cct gac gag acc gcg tcc aac cgt ctg aac gcg acc      1465
Arg Val Phe Gly Pro Asp Glu Thr Ala Ser Asn Arg Leu Asn Ala Thr
```

-continued

```
                         435                 440                 445
tac gag gtc acc aag aag cag tgg gac aac gga tac ctc tcg gct ctc    1513
Tyr Glu Val Thr Lys Lys Gln Trp Asp Asn Gly Tyr Leu Ser Ala Leu
            450                 455                 460 gtc gac gag aac atg gcc gtc acc ggc cag gtt gtc gag cag ctc tcc    1561
Val Asp Glu Asn Met Ala Val Thr Gly Gln Val Val Glu Gln Leu Ser
        465                 470                 475 gag cat cag tgc gaa ggc ttc ctc gag gcc tac ctg ctc acc ggc cgt    1609
Glu His Gln Cys Glu Gly Phe Leu Glu Ala Tyr Leu Leu Thr Gly Arg
    480                 485                 490 cac ggc atc tgg agc tcc tac gag tcc ttc gtg cac gtg atc gac tcc    1657
His Gly Ile Trp Ser Ser Tyr Glu Ser Phe Val His Val Ile Asp Ser
495                 500                 505                 510 atg ctg aac cag cat gcg aag tgg ctc gag gcc acc gtc cgc gag atc    1705
Met Leu Asn Gln His Ala Lys Trp Leu Glu Ala Thr Val Arg Glu Ile
                515                 520                 525 ccg tgg cgt aag ccg atc tcc tcg gtg aac ctc ctg gtc tcc tcg cac    1753
Pro Trp Arg Lys Pro Ile Ser Ser Val Asn Leu Leu Val Ser Ser His
            530                 535                 540 gtg tgg cgt cag gat cac aac ggc ttc tcg cac cag gat ccg ggt gtg    1801
Val Trp Arg Gln Asp His Asn Gly Phe Ser His Gln Asp Pro Gly Val
        545                 550                 555 acc tcc gtc ctg ctg aac aag acg ttc aac aac gac cac gtg acg aac    1849
Thr Ser Val Leu Leu Asn Lys Thr Phe Asn Asn Asp His Val Thr Asn
    560                 565                 570 atc tac ttc gcg acc gat gcc aac atg ctg ctg gcc atc gcc gag aag    1897
Ile Tyr Phe Ala Thr Asp Ala Asn Met Leu Leu Ala Ile Ala Glu Lys
575                 580                 585                 590 tgc ttc aag tcc acc aac aag atc aac gca atc ttc gcc ggc aag cag    1945
Cys Phe Lys Ser Thr Asn Lys Ile Asn Ala Ile Phe Ala Gly Lys Gln
                595                 600                 605 ccg gcc gcg acg tgg atc acc ctc gac gag gta cgc gcc gag ctc gag    1993
Pro Ala Ala Thr Trp Ile Thr Leu Asp Glu Val Arg Ala Glu Leu Glu
            610                 615                 620 gct ggt gcc gcc gag tgg aag tgg gct tcc aac gcc aag agc aac gac    2041
Ala Gly Ala Ala Glu Trp Lys Trp Ala Ser Asn Ala Lys Ser Asn Asp
        625                 630                 635 gag gtc cag gtt gtc ctc gcc gcc gcc ggc gac gtc ccg acc cag gag    2089
Glu Val Gln Val Val Leu Ala Ala Ala Gly Asp Val Pro Thr Gln Glu
    640                 645                 650 atc atg gcc gct tcc gat gcc ctc aac aag atg ggc atc aag ttc aag    2137
Ile Met Ala Ala Ser Asp Ala Leu Asn Lys Met Gly Ile Lys Phe Lys
655                 660                 665                 670 gtc gtc aac gtc gtg gac ctc atc aag ctg cag tcc tcg aag gag aac    2185
Val Val Asn Val Val Asp Leu Ile Lys Leu Gln Ser Ser Lys Glu Asn
                675                 680                 685 gac gag gcc atg tct gac gag gac ttc gcc gac ctg ttc acc gcg gac    2233
Asp Glu Ala Met Ser Asp Glu Asp Phe Ala Asp Leu Phe Thr Ala Asp
            690                 695                 700 aag ccg gtc ctc ttc gcc tac cac tcc tat gcc cag gac gtt cgt ggc    2281
Lys Pro Val Leu Phe Ala Tyr His Ser Tyr Ala Gln Asp Val Arg Gly
        705                 710                 715 ctc atc tac gac cgc ccg aac cac gac aac ttc acc gtt gtc gga tac    2329
Leu Ile Tyr Asp Arg Pro Asn His Asp Asn Phe Thr Val Val Gly Tyr
    720                 725                 730 aag gag cag ggc tcc acg acg acg ccg ttc gac atg gtg cgt gtc aac    2377
Lys Glu Gln Gly Ser Thr Thr Thr Pro Phe Asp Met Val Arg Val Asn
735                 740                 745                 750 gac atg gat cgc tac gcc ctt cag gcc aag gcc ctc gag ctc atc gac    2425
Asp Met Asp Arg Tyr Ala Leu Gln Ala Lys Ala Leu Glu Leu Ile Asp
```

```
                        755                 760                 765
gcc gac aag tat gcc gac aag atc aac gag ctc aac gag ttc cgc aag        2473
Ala Asp Lys Tyr Ala Asp Lys Ile Asn Glu Leu Asn Glu Phe Arg Lys
            770                 775                 780 acc gcg ttc cag ttc gcc gtc gac aat ggc tat gac att cct gag ttc        2521
Thr Ala Phe Gln Phe Ala Val Asp Asn Gly Tyr Asp Ile Pro Glu Phe
        785                 790                 795 acc gat tgg gtg tac ccg gat gtc aag gtc gac gag acc tcc atg ctc        2569
Thr Asp Trp Val Tyr Pro Asp Val Lys Val Asp Glu Thr Ser Met Leu
    800                 805                 810 tcc gcc acc gcc gcg acc gcc ggc gac aac gag tga gcatagtctc             2615
Ser Ala Thr Ala Ala Thr Ala Gly Asp Asn Glu
815                 820                 825 atcgcttagc cgatgaaagg cccgggtgtc cgcacccggg cctttt                     2660

<210> SEQ ID NO 57
<211> LENGTH: 825
<212> TYPE: PRT
<213> ORGANISM: Bifidobacterium lactis

<400> SEQUENCE: 57

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Ile Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
```

-continued

```
            275                 280                 285
Pro Phe Tyr Pro Met Leu Ile Phe Arg Thr Pro Lys Gly Trp Thr Cys
            290                 295                 300
Pro Lys Phe Ile Asp Gly Lys Lys Thr Glu Gly Ser Trp Arg Ala His
305                 310                 315                 320
Gln Val Pro Leu Ala Ser Ala Arg Asp Thr Glu Ala His Phe Glu Val
            325                 330                 335
Leu Lys Gly Trp Met Glu Ser Tyr Lys Pro Glu Glu Leu Phe Asn Ala
            340                 345                 350
Asp Gly Ser Ile Lys Glu Asp Val Thr Ala Phe Met Pro Lys Gly Glu
            355                 360                 365
Leu Arg Ile Gly Ala Asn Pro Asn Ala Asn Gly Gly Arg Ile Arg Glu
    370                 375                 380
Asp Leu Lys Leu Pro Glu Leu Asp Gln Tyr Glu Ile Thr Gly Val Lys
385                 390                 395                 400
Glu Tyr Gly His Gly Trp Gly Gln Val Glu Ala Pro Arg Ser Leu Gly
                405                 410                 415
Ala Tyr Cys Arg Asp Ile Ile Lys Asn Asn Pro Asp Ser Phe Arg Val
            420                 425                 430
Phe Gly Pro Asp Glu Thr Ala Ser Asn Arg Leu Asn Ala Thr Tyr Glu
        435                 440                 445
Val Thr Lys Lys Gln Trp Asp Asn Gly Tyr Leu Ser Ala Leu Val Asp
    450                 455                 460
Glu Asn Met Ala Val Thr Gly Gln Val Val Glu Gln Leu Ser Glu His
465                 470                 475                 480
Gln Cys Glu Gly Phe Leu Glu Ala Tyr Leu Leu Thr Gly Arg His Gly
                485                 490                 495
Ile Trp Ser Ser Tyr Glu Ser Phe Val His Val Ile Asp Ser Met Leu
            500                 505                 510
Asn Gln His Ala Lys Trp Leu Glu Ala Thr Val Arg Glu Ile Pro Trp
        515                 520                 525
Arg Lys Pro Ile Ser Ser Val Asn Leu Leu Val Ser Ser His Val Trp
530                 535                 540
Arg Gln Asp His Asn Gly Phe Ser His Gln Asp Pro Gly Val Thr Ser
545                 550                 555                 560
Val Leu Leu Asn Lys Thr Phe Asn Asn Asp His Val Thr Asn Ile Tyr
                565                 570                 575
Phe Ala Thr Asp Ala Asn Met Leu Leu Ala Ile Ala Glu Lys Cys Phe
            580                 585                 590
Lys Ser Thr Asn Lys Ile Asn Ala Ile Phe Ala Gly Lys Gln Pro Ala
        595                 600                 605
Ala Thr Trp Ile Thr Leu Asp Glu Val Arg Ala Glu Leu Glu Ala Gly
    610                 615                 620
Ala Ala Glu Trp Lys Trp Ala Ser Asn Ala Lys Ser Asn Asp Glu Val
625                 630                 635                 640
Gln Val Val Leu Ala Ala Gly Asp Val Pro Thr Gln Glu Ile Met
                645                 650                 655
Ala Ala Ser Asp Ala Leu Asn Lys Met Gly Ile Lys Phe Lys Val Val
            660                 665                 670
Asn Val Val Asp Leu Ile Lys Leu Gln Ser Ser Lys Glu Asn Asp Glu
        675                 680                 685
Ala Met Ser Asp Glu Asp Phe Ala Asp Leu Phe Thr Ala Asp Lys Pro
    690                 695                 700
```

```
Val Leu Phe Ala Tyr His Ser Tyr Ala Gln Asp Val Arg Gly Leu Ile
705                 710                 715                 720

Tyr Asp Arg Pro Asn His Asp Asn Phe Thr Val Val Gly Tyr Lys Glu
            725                 730                 735

Gln Gly Ser Thr Thr Thr Pro Phe Asp Met Val Arg Val Asn Asp Met
        740                 745                 750

Asp Arg Tyr Ala Leu Gln Ala Lys Ala Leu Glu Leu Ile Asp Ala Asp
    755                 760                 765

Lys Tyr Ala Asp Lys Ile Asn Glu Leu Asn Glu Phe Arg Lys Thr Ala
770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Ser Met Leu Ser Ala
                805                 810                 815

Thr Ala Ala Thr Ala Gly Asp Asn Glu
                820                 825

<210> SEQ ID NO 58
<211> LENGTH: 23
<212> TYPE: DNA
<213> ORGANISM: Artificial sequence
<220> FEATURE:
<223> OTHER INFORMATION: primer

<400> SEQUENCE: 58
ctgttaaggc agaaaccgtc gct                                           23

<210> SEQ ID NO 59
<211> LENGTH: 23
<212> TYPE: DNA
<213> ORGANISM: Artificial sequence
<220> FEATURE:
<223> OTHER INFORMATION: primer

<400> SEQUENCE: 59
tcttggtgtc gaaagtgcac acc                                           23

<210> SEQ ID NO 60
<211> LENGTH: 20
<212> TYPE: DNA
<213> ORGANISM: Artificial sequence
<220> FEATURE:
<223> OTHER INFORMATION: primer

<400> SEQUENCE: 60
cgcgaggtac cacctgtcac                                               20

<210> SEQ ID NO 61
<211> LENGTH: 20
<212> TYPE: DNA
<213> ORGANISM: Artificial sequence
<220> FEATURE:
<223> OTHER INFORMATION: primer

<400> SEQUENCE: 61
caatccaggt accggcaacc                                               20

<210> SEQ ID NO 62
<211> LENGTH: 2760
<212> TYPE: DNA
<213> ORGANISM: Corynebacterium glutamicum
<220> FEATURE:
<221> NAME/KEY: CDS
<222> LOCATION: (1)..(2757)
```

<400> SEQUENCE: 62

```
atg act gat ttt tta cgc gat gac atc agg ttc ctc ggt caa atc ctc      48
Met Thr Asp Phe Leu Arg Asp Asp Ile Arg Phe Leu Gly Gln Ile Leu
1               5                   10                  15 ggt gag gta att gcg gaa caa gaa ggc cag gag gtt tat gaa ctg gtc      96
Gly Glu Val Ile Ala Glu Gln Glu Gly Gln Glu Val Tyr Glu Leu Val
            20                  25                  30 gaa caa gcg cgc ctg act tct ttt gat atc gcc aag ggc aac gcc gaa     144
Glu Gln Ala Arg Leu Thr Ser Phe Asp Ile Ala Lys Gly Asn Ala Glu
        35                  40                  45 atg gat agc ctg gtt cag gtt ttc gac ggc att act cca gcc aag gca     192
Met Asp Ser Leu Val Gln Val Phe Asp Gly Ile Thr Pro Ala Lys Ala
    50                  55                  60 aca ccg att gct cgc gca ttt tcc cac ttc gct ctg ctg gct aac ctg     240
Thr Pro Ile Ala Arg Ala Phe Ser His Phe Ala Leu Leu Ala Asn Leu
65                  70                  75                  80 gcg gaa gac ctc tac gat gaa gag ctt cgt gaa cag gct ctc gat gca     288
Ala Glu Asp Leu Tyr Asp Glu Glu Leu Arg Glu Gln Ala Leu Asp Ala
                85                  90                  95 ggc gac acc cct ccg gac agc act ctt gat gcc acc tgg ctg aaa ctc     336
Gly Asp Thr Pro Pro Asp Ser Thr Leu Asp Ala Thr Trp Leu Lys Leu
            100                 105                 110 aat gag ggc aat gtt ggc gca gaa gct gtg gcc gat gtg ctg cgc aat     384
Asn Glu Gly Asn Val Gly Ala Glu Ala Val Ala Asp Val Leu Arg Asn
        115                 120                 125 gct gag gtg gcg ccg gtt ctg act gcg cac cca act gag act cgc cgc     432
Ala Glu Val Ala Pro Val Leu Thr Ala His Pro Thr Glu Thr Arg Arg
    130                 135                 140 cgc act gtt ttt gat gcg caa aag tgg atc acc acc cac atg cgt gaa     480
Arg Thr Val Phe Asp Ala Gln Lys Trp Ile Thr Thr His Met Arg Glu
145                 150                 155                 160 cgc cac gct ttg cag tct gcg gag cct acc gct cgt acg caa agc aag     528
Arg His Ala Leu Gln Ser Ala Glu Pro Thr Ala Arg Thr Gln Ser Lys
                165                 170                 175 ttg gat gag atc gag aag aac atc cgc cgt cgc atc acc att ttg tgg     576
Leu Asp Glu Ile Glu Lys Asn Ile Arg Arg Arg Ile Thr Ile Leu Trp
            180                 185                 190 cag acc gcg ttg att cgt gtg gcc cgc cca cgt atc gag gac gag atc     624
Gln Thr Ala Leu Ile Arg Val Ala Arg Pro Arg Ile Glu Asp Glu Ile
        195                 200                 205 gaa gta ggg ctg cgc tac tac aag ctg agc ctt tgt gaa gag att cca     672
Glu Val Gly Leu Arg Tyr Tyr Lys Leu Ser Leu Leu Glu Glu Ile Pro
    210                 215                 220 cgt atc aac cgt gat gtg gct gtt gag ctt cgt gag cgt ttc ggc gag     720
Arg Ile Asn Arg Asp Val Ala Val Glu Leu Arg Glu Arg Phe Gly Glu
225                 230                 235                 240 ggt gtt cct ttg aag ccc gtg gtc aag cca ggt tcc tgg att ggt gga     768
Gly Val Pro Leu Lys Pro Val Val Lys Pro Gly Ser Trp Ile Gly Gly
                245                 250                 255 gac cac gac ggt aac cct tat gtc acc gcg gaa aca gtt gag tat tcc     816
Asp His Asp Gly Asn Pro Tyr Val Thr Ala Glu Thr Val Glu Tyr Ser
            260                 265                 270 act cac cgc gct gcg gaa acc gtg ctc aag tac tat gca cgc cag ctg     864
Thr His Arg Ala Ala Glu Thr Val Leu Lys Tyr Tyr Ala Arg Gln Leu
        275                 280                 285 cat tcc ctc gag cat gag ctc agc ctg tcg gac cgc atg aat aag gtc     912
His Ser Leu Glu His Glu Leu Ser Leu Ser Asp Arg Met Asn Lys Val
    290                 295                 300 acc ccg cag ctg ctt gcg ctg gca gat gca ggg cac aac gac gtg cca     960
Thr Pro Gln Leu Leu Ala Leu Ala Asp Ala Gly His Asn Asp Val Pro
```

-continued

```
Thr Pro Gln Leu Leu Ala Leu Ala Asp Ala Gly His Asn Asp Val Pro
305                 310                 315                 320 agc cgc gtg gat gag cct tat cga cgc gcc gtc cat ggc gtt cgc gga    1008
Ser Arg Val Asp Glu Pro Tyr Arg Arg Ala Val His Gly Val Arg Gly
                325                 330                 335 cgt atc ctc gcg acg acg gcc gag ctg atc ggc gag gac gcc gtt gag    1056
Arg Ile Leu Ala Thr Thr Ala Glu Leu Ile Gly Glu Asp Ala Val Glu
            340                 345                 350 ggc gtg tgg ttc aag gtc ttt act cca tac gca tct ccg gaa gaa ttc    1104
Gly Val Trp Phe Lys Val Phe Thr Pro Tyr Ala Ser Pro Glu Glu Phe
        355                 360                 365 tta aac gat gcg ttg acc att gat cat tct ctg cgt gaa tcc aag gac    1152
Leu Asn Asp Ala Leu Thr Ile Asp His Ser Leu Arg Glu Ser Lys Asp
    370                 375                 380 gtt ctc att gcc gat gat cgt ttg tct gtg ctg att tct gcc atc gag    1200
Val Leu Ile Ala Asp Asp Arg Leu Ser Val Leu Ile Ser Ala Ile Glu
385                 390                 395                 400 agc ttt gga ttc aac ctt tac gca ctg gat ctg cgc caa aac tcc gaa    1248
Ser Phe Gly Phe Asn Leu Tyr Ala Leu Asp Leu Arg Gln Asn Ser Glu
                405                 410                 415 agc tac gag gac gtc ctc acc gag ctt ttc gaa cgc gcc caa gtc acc    1296
Ser Tyr Glu Asp Val Leu Thr Glu Leu Phe Glu Arg Ala Gln Val Thr
            420                 425                 430 gca aac tac cgc gag ctg tct gaa gca gag aag ctt gag gtg ctg ctg    1344
Ala Asn Tyr Arg Glu Leu Ser Glu Ala Glu Lys Leu Glu Val Leu Leu
        435                 440                 445 aag gaa ctg cgc agc cct cgt ccg ctg atc ccg cac ggt tca gat gaa    1392
Lys Glu Leu Arg Ser Pro Arg Pro Leu Ile Pro His Gly Ser Asp Glu
    450                 455                 460 tac agc gag gtc acc gac cgc gag ctc ggc atc ttc cgc acc gcg tcg    1440
Tyr Ser Glu Val Thr Asp Arg Glu Leu Gly Ile Phe Arg Thr Ala Ser
465                 470                 475                 480 gag gct gtt aag aaa ttc ggg cca cgg atg gtg cct cac tgc atc atc    1488
Glu Ala Val Lys Lys Phe Gly Pro Arg Met Val Pro His Cys Ile Ile
                485                 490                 495 tcc atg gca tca tcg gtc acc gat gtg ctc gag ccg atg gtg ttg ctc    1536
Ser Met Ala Ser Ser Val Thr Asp Val Leu Glu Pro Met Val Leu Leu
            500                 505                 510 aag gaa ttc gga ctc atc gca gcc aac ggc gac aac cca cgc ggc acc    1584
Lys Glu Phe Gly Leu Ile Ala Ala Asn Gly Asp Asn Pro Arg Gly Thr
        515                 520                 525 gtc gat gtc atc cca ctg ttc gaa acc atc gaa gat ctc cag gcc ggc    1632
Val Asp Val Ile Pro Leu Phe Glu Thr Ile Glu Asp Leu Gln Ala Gly
    530                 535                 540 gcc gga atc ctc gac gaa ctg tgg aaa att gat ctc tac cgc aac tac    1680
Ala Gly Ile Leu Asp Glu Leu Trp Lys Ile Asp Leu Tyr Arg Asn Tyr
545                 550                 555                 560 ctc ctg cag cgc gac aac gtc cag gaa gtc atg ctc ggt tac tcc gat    1728
Leu Leu Gln Arg Asp Asn Val Gln Glu Val Met Leu Gly Tyr Ser Asp
                565                 570                 575 tcc aac aag gat ggc gga tat ttc tcc gca aac tgg gcg ctt tac gac    1776
Ser Asn Lys Asp Gly Gly Tyr Phe Ser Ala Asn Trp Ala Leu Tyr Asp
            580                 585                 590 gcg gaa ctg cag ctc gtc gaa cta tgc cga tca gcc ggg gtc aag ctt    1824
Ala Glu Leu Gln Leu Val Glu Leu Cys Arg Ser Ala Gly Val Lys Leu
        595                 600                 605 cgc ctg ttc cac ggc cgt ggt ggc acc gtc ggc cgc ggt ggc gga cct    1872
Arg Leu Phe His Gly Arg Gly Gly Thr Val Gly Arg Gly Gly Gly Pro
    610                 615                 620 tcc tac gac gcg att ctt gcc cag ccc agg ggg gct gtc caa ggt tcc    1920
```

```
Ser Tyr Asp Ala Ile Leu Ala Gln Pro Arg Gly Ala Val Gln Gly Ser
625                 630                 635                 640 gtg cgc atc acc gag cag ggc gag atc atc tcc gct aag tac ggc aac       1968
Val Arg Ile Thr Glu Gln Gly Glu Ile Ile Ser Ala Lys Tyr Gly Asn
                645                 650                 655 ccc gaa acc gcg cgc cga aac ctc gaa gcc ctg gtc tca gcc acg ctt       2016
Pro Glu Thr Ala Arg Arg Asn Leu Glu Ala Leu Val Ser Ala Thr Leu
            660                 665                 670 gag gca tcg ctt ctc gac gtc tcc gaa ctc acc gat cac caa cgc gcg       2064
Glu Ala Ser Leu Leu Asp Val Ser Glu Leu Thr Asp His Gln Arg Ala
        675                 680                 685 tac gac atc atg agt gag atc tct gag ctc agc ttg aag aag tac gcc       2112
Tyr Asp Ile Met Ser Glu Ile Ser Glu Leu Ser Leu Lys Lys Tyr Ala
    690                 695                 700 tcc ttg gtg cac gag gat caa ggc ttc atc gat tac ttc acc cag tcc       2160
Ser Leu Val His Glu Asp Gln Gly Phe Ile Asp Tyr Phe Thr Gln Ser
705                 710                 715                 720 acg ccg ctg cag gag att gga tcc ctc aac atc gga tcc agg cct tcc       2208
Thr Pro Leu Gln Glu Ile Gly Ser Leu Asn Ile Gly Ser Arg Pro Ser
                725                 730                 735 tca cgc aag cag acc tcc tcg gtg gaa gat ttg cga gcc atc cca tgg       2256
Ser Arg Lys Gln Thr Ser Ser Val Glu Asp Leu Arg Ala Ile Pro Trp
            740                 745                 750 gtg ctc agc tgg tca cag tct cgt gtc atg ctg cca ggc tgg ttt ggt       2304
Val Leu Ser Trp Ser Gln Ser Arg Val Met Leu Pro Gly Trp Phe Gly
        755                 760                 765 gtc gga acc gca tta gag cag tgg att ggc gaa ggg gag cag gcc acc       2352
Val Gly Thr Ala Leu Glu Gln Trp Ile Gly Glu Gly Glu Gln Ala Thr
    770                 775                 780 caa cgc att gcc gag ctg caa aca ctc aat gag tcc tgg cca ttt ttc       2400
Gln Arg Ile Ala Glu Leu Gln Thr Leu Asn Glu Ser Trp Pro Phe Phe
785                 790                 795                 800 acc tca gtg ttg gat aac atg gct cag gtg atg tcc aag gca gag ctg       2448
Thr Ser Val Leu Asp Asn Met Ala Gln Val Met Ser Lys Ala Glu Leu
                805                 810                 815 cgt ttg gca aag ctc tac gca gac ctg atc cca gat acg gaa gta gcc       2496
Arg Leu Ala Lys Leu Tyr Ala Asp Leu Ile Pro Asp Thr Glu Val Ala
            820                 825                 830 gag cga gtc tat tcc gtc atc cgc gag gag tac ttc ctg acc aag aag       2544
Glu Arg Val Tyr Ser Val Ile Arg Glu Glu Tyr Phe Leu Thr Lys Lys
        835                 840                 845 atg ttc tgc gta atc acc ggc tct gat gat ctg ctt gat gac aac cca       2592
Met Phe Cys Val Ile Thr Gly Ser Asp Asp Leu Leu Asp Asp Asn Pro
    850                 855                 860 ctt ctc gca cgc tct gtc cag cgc cga tac ccc tac ctg ctt cca ctc       2640
Leu Leu Ala Arg Ser Val Gln Arg Arg Tyr Pro Tyr Leu Leu Pro Leu
865                 870                 875                 880 aac gtg atc cag gta gag atg atg cga cgc tac cga aaa ggc gac caa       2688
Asn Val Ile Gln Val Glu Met Met Arg Arg Tyr Arg Lys Gly Asp Gln
                885                 890                 895 agc gag caa gtg tcc cgc aac att cag ctg acc atg aac ggt ctt tcc       2736
Ser Glu Gln Val Ser Arg Asn Ile Gln Leu Thr Met Asn Gly Leu Ser
            900                 905                 910 act gcg ctg cgc aac tcc ggc tag                                       2760
Thr Ala Leu Arg Asn Ser Gly
        915
```

<210> SEQ ID NO 63
<211> LENGTH: 919
<212> TYPE: PRT
<213> ORGANISM: Corynebacterium glutamicum

<400> SEQUENCE: 63

```
Met Thr Asp Phe Leu Arg Asp Asp Ile Arg Phe Leu Gly Gln Ile Leu
1               5                   10                  15
Gly Glu Val Ile Ala Glu Gln Glu Gly Gln Glu Val Tyr Glu Leu Val
            20                  25                  30
Glu Gln Ala Arg Leu Thr Ser Phe Asp Ile Ala Lys Gly Asn Ala Glu
        35                  40                  45
Met Asp Ser Leu Val Gln Val Phe Asp Gly Ile Thr Pro Ala Lys Ala
50                  55                  60
Thr Pro Ile Ala Arg Ala Phe Ser His Phe Ala Leu Leu Ala Asn Leu
65                  70                  75                  80
Ala Glu Asp Leu Tyr Asp Glu Glu Leu Arg Glu Gln Ala Leu Asp Ala
                85                  90                  95
Gly Asp Thr Pro Pro Asp Ser Thr Leu Asp Ala Thr Trp Leu Lys Leu
            100                 105                 110
Asn Glu Gly Asn Val Gly Ala Glu Ala Val Ala Asp Val Leu Arg Asn
        115                 120                 125
Ala Glu Val Ala Pro Val Leu Thr Ala His Pro Thr Glu Thr Arg Arg
130                 135                 140
Arg Thr Val Phe Asp Ala Gln Lys Trp Ile Thr Thr His Met Arg Glu
145                 150                 155                 160
Arg His Ala Leu Gln Ser Ala Glu Pro Thr Ala Arg Thr Gln Ser Lys
                165                 170                 175
Leu Asp Glu Ile Glu Lys Asn Ile Arg Arg Ile Thr Ile Leu Trp
            180                 185                 190
Gln Thr Ala Leu Ile Arg Val Ala Arg Pro Ile Glu Asp Glu Ile
        195                 200                 205
Glu Val Gly Leu Arg Tyr Tyr Lys Leu Ser Leu Leu Glu Glu Ile Pro
210                 215                 220
Arg Ile Asn Arg Asp Val Ala Val Glu Leu Arg Glu Arg Phe Gly Glu
225                 230                 235                 240
Gly Val Pro Leu Lys Pro Val Val Lys Pro Gly Ser Trp Ile Gly Gly
                245                 250                 255
Asp His Asp Gly Asn Pro Tyr Val Thr Ala Glu Thr Val Glu Tyr Ser
            260                 265                 270
Thr His Arg Ala Ala Glu Thr Val Leu Lys Tyr Tyr Ala Arg Gln Leu
        275                 280                 285
His Ser Leu Glu His Glu Leu Ser Leu Ser Asp Arg Met Asn Lys Val
290                 295                 300
Thr Pro Gln Leu Leu Ala Leu Ala Asp Ala Gly His Asn Asp Val Pro
305                 310                 315                 320
Ser Arg Val Asp Glu Pro Tyr Arg Arg Ala Val His Gly Val Arg Gly
                325                 330                 335
Arg Ile Leu Ala Thr Thr Ala Glu Leu Ile Gly Glu Asp Ala Val Glu
            340                 345                 350
Gly Val Trp Phe Lys Val Phe Thr Pro Tyr Ala Ser Pro Glu Glu Phe
        355                 360                 365
Leu Asn Asp Ala Leu Thr Ile Asp His Ser Leu Arg Glu Ser Lys Asp
370                 375                 380
Val Leu Ile Ala Asp Asp Arg Leu Ser Val Leu Ile Ser Ala Ile Glu
385                 390                 395                 400
Ser Phe Gly Phe Asn Leu Tyr Ala Leu Asp Leu Arg Gln Asn Ser Glu
                405                 410                 415
```

```
Ser Tyr Glu Asp Val Leu Thr Glu Leu Phe Glu Arg Ala Gln Val Thr
            420                 425                 430

Ala Asn Tyr Arg Glu Leu Ser Glu Ala Glu Lys Leu Glu Val Leu Leu
            435                 440                 445

Lys Glu Leu Arg Ser Pro Arg Pro Leu Ile Pro His Gly Ser Asp Glu
            450                 455                 460

Tyr Ser Glu Val Thr Asp Arg Glu Leu Gly Ile Phe Arg Thr Ala Ser
465                 470                 475                 480

Glu Ala Val Lys Lys Phe Gly Pro Arg Met Val Pro His Cys Ile Ile
                485                 490                 495

Ser Met Ala Ser Ser Val Thr Asp Val Leu Glu Pro Met Val Leu Leu
            500                 505                 510

Lys Glu Phe Gly Leu Ile Ala Ala Asn Gly Asp Asn Pro Arg Gly Thr
            515                 520                 525

Val Asp Val Ile Pro Leu Phe Glu Thr Ile Glu Asp Leu Gln Ala Gly
            530                 535                 540

Ala Gly Ile Leu Asp Glu Leu Trp Lys Ile Asp Leu Tyr Arg Asn Tyr
545                 550                 555                 560

Leu Leu Gln Arg Asp Asn Val Gln Glu Val Met Leu Gly Tyr Ser Asp
            565                 570                 575

Ser Asn Lys Asp Gly Gly Tyr Phe Ser Ala Asn Trp Ala Leu Tyr Asp
            580                 585                 590

Ala Glu Leu Gln Leu Val Glu Leu Cys Arg Ser Ala Gly Val Lys Leu
            595                 600                 605

Arg Leu Phe His Gly Arg Gly Gly Thr Val Gly Arg Gly Gly Gly Pro
            610                 615                 620

Ser Tyr Asp Ala Ile Leu Ala Gln Pro Arg Gly Ala Val Gln Gly Ser
625                 630                 635                 640

Val Arg Ile Thr Glu Gln Gly Glu Ile Ile Ser Ala Lys Tyr Gly Asn
            645                 650                 655

Pro Glu Thr Ala Arg Arg Asn Leu Glu Ala Leu Val Ser Ala Thr Leu
            660                 665                 670

Glu Ala Ser Leu Leu Asp Val Ser Glu Leu Thr Asp His Gln Arg Ala
            675                 680                 685

Tyr Asp Ile Met Ser Glu Ile Ser Glu Leu Ser Leu Lys Lys Tyr Ala
            690                 695                 700

Ser Leu Val His Glu Asp Gln Gly Phe Ile Asp Tyr Phe Thr Gln Ser
705                 710                 715                 720

Thr Pro Leu Gln Glu Ile Gly Ser Leu Asn Ile Gly Ser Arg Pro Ser
            725                 730                 735

Ser Arg Lys Gln Thr Ser Ser Val Glu Asp Leu Arg Ala Ile Pro Trp
            740                 745                 750

Val Leu Ser Trp Ser Gln Ser Arg Val Met Leu Pro Gly Trp Phe Gly
            755                 760                 765

Val Gly Thr Ala Leu Glu Gln Trp Ile Gly Glu Gly Glu Gln Ala Thr
            770                 775                 780

Gln Arg Ile Ala Glu Leu Gln Thr Leu Asn Glu Ser Trp Pro Phe Phe
785                 790                 795                 800

Thr Ser Val Leu Asp Asn Met Ala Gln Val Met Ser Lys Ala Glu Leu
            805                 810                 815

Arg Leu Ala Lys Leu Tyr Ala Asp Leu Ile Pro Asp Thr Glu Val Ala
            820                 825                 830

Glu Arg Val Tyr Ser Val Ile Arg Glu Glu Tyr Phe Leu Thr Lys Lys
```

```
                     835                 840                 845
Met Phe Cys Val Ile Thr Gly Ser Asp Asp Leu Leu Asp Asp Asn Pro
850                 855                 860

Leu Leu Ala Arg Ser Val Gln Arg Arg Tyr Pro Tyr Leu Leu Pro Leu
865                 870                 875                 880

Asn Val Ile Gln Val Glu Met Met Arg Arg Tyr Arg Lys Gly Asp Gln
                885                 890                 895

Ser Glu Gln Val Ser Arg Asn Ile Gln Leu Thr Met Asn Gly Leu Ser
            900                 905                 910

Thr Ala Leu Arg Asn Ser Gly
        915

<210> SEQ ID NO 64
<211> LENGTH: 3423
<212> TYPE: DNA
<213> ORGANISM: Corynebacterium glutamicum
<220> FEATURE:
<221> NAME/KEY: CDS
<222> LOCATION: (1)..(3420)

<400> SEQUENCE: 64 gtg tcg act cac aca tct tca acg ctt cca gca ttc aaa aag atc ttg      48
Val Ser Thr His Thr Ser Ser Thr Leu Pro Ala Phe Lys Lys Ile Leu
1               5                   10                  15 gta gca aac cgc ggc gaa atc gcg gtc cgt gct ttc cgt gca gca ctc      96
Val Ala Asn Arg Gly Glu Ile Ala Val Arg Ala Phe Arg Ala Ala Leu
            20                  25                  30 gaa acc ggt gca gcc acg gta gct att tac ccc cgt gaa gat cgg gga     144
Glu Thr Gly Ala Ala Thr Val Ala Ile Tyr Pro Arg Glu Asp Arg Gly
        35                  40                  45 tca ttc cac cgc tct ttt gct tct gaa gct gtc cgc att ggt acc gaa     192
Ser Phe His Arg Ser Phe Ala Ser Glu Ala Val Arg Ile Gly Thr Glu
    50                  55                  60 ggc tca cca gtc aag gcg tac ctg gac atc gat gaa att atc ggt gca     240
Gly Ser Pro Val Lys Ala Tyr Leu Asp Ile Asp Glu Ile Ile Gly Ala
65                  70                  75                  80 gct aaa aaa gtt aaa gca gat gcc att tac ccg gga tac ggc ttc ctg     288
Ala Lys Lys Val Lys Ala Asp Ala Ile Tyr Pro Gly Tyr Gly Phe Leu
                85                  90                  95 tct gaa aat gcc cag ctt gcc cgc gag tgt gcg gaa aac ggc att act     336
Ser Glu Asn Ala Gln Leu Ala Arg Glu Cys Ala Glu Asn Gly Ile Thr
            100                 105                 110 ttt att ggc cca acc cca gag gtt ctt gat ctc acc ggt gat aag tct     384
Phe Ile Gly Pro Thr Pro Glu Val Leu Asp Leu Thr Gly Asp Lys Ser
        115                 120                 125 cgc gcg gta acc gcc gcg aag aag gct ggt ctg cca gtt ttg gcg gaa     432
Arg Ala Val Thr Ala Ala Lys Lys Ala Gly Leu Pro Val Leu Ala Glu
    130                 135                 140 tcc acc ccg agc aaa aac atc gat gag atc gtt aaa agc gct gaa ggc     480
Ser Thr Pro Ser Lys Asn Ile Asp Glu Ile Val Lys Ser Ala Glu Gly
145                 150                 155                 160 cag act tac ccc atc ttt gtg aag gca gtt gcc ggt ggt ggc gga cgc     528
Gln Thr Tyr Pro Ile Phe Val Lys Ala Val Ala Gly Gly Gly Gly Arg
                165                 170                 175 ggt atg cgt ttt gtt gct tca cct gat gag ctt cgc aaa tta gca aca     576
Gly Met Arg Phe Val Ala Ser Pro Asp Glu Leu Arg Lys Leu Ala Thr
            180                 185                 190 gaa gca tct cgt gaa gct gaa gcg gct ttc ggc gat ggc gcg gta tat     624
Glu Ala Ser Arg Glu Ala Glu Ala Ala Phe Gly Asp Gly Ala Val Tyr
        195                 200                 205
```

```
gtc gaa cgt gct gtg att aac cct cag cat att gaa gtg cag atc ctt      672
Val Glu Arg Ala Val Ile Asn Pro Gln His Ile Glu Val Gln Ile Leu
    210                 215                 220 ggc gat cac act gga gaa gtt gta cac ctt tat gaa cgt gac tgc tca      720
Gly Asp His Thr Gly Glu Val Val His Leu Tyr Glu Arg Asp Cys Ser
225                 230                 235                 240 ctg cag cgt cgt cac caa aaa gtt gtc gaa att gcg cca gca cag cat      768
Leu Gln Arg Arg His Gln Lys Val Val Glu Ile Ala Pro Ala Gln His
                245                 250                 255 ttg gat cca gaa ctg cgt gat cgc att tgt gcg gat gca gta aag ttc      816
Leu Asp Pro Glu Leu Arg Asp Arg Ile Cys Ala Asp Ala Val Lys Phe
            260                 265                 270 tgc cgc tcc att ggt tac cag ggc gcg gga acc gtg gaa ttc ttg gtc      864
Cys Arg Ser Ile Gly Tyr Gln Gly Ala Gly Thr Val Glu Phe Leu Val
        275                 280                 285 gat gaa aag ggc aac cac gtc ttc atc gaa atg aac cca cgt atc cag      912
Asp Glu Lys Gly Asn His Val Phe Ile Glu Met Asn Pro Arg Ile Gln
    290                 295                 300 gtt gag cac acc gtg act gaa gaa gtc acc gag gtg gac ctg gtg aag      960
Val Glu His Thr Val Thr Glu Glu Val Thr Glu Val Asp Leu Val Lys
305                 310                 315                 320 gcg cag atg cgc ttg gct gct ggt gca acc ttg aag gaa ttg ggt ctg     1008
Ala Gln Met Arg Leu Ala Ala Gly Ala Thr Leu Lys Glu Leu Gly Leu
                325                 330                 335 acc caa gat aag atc aag acc cac ggt gca gca ctg cag tgc cgc atc     1056
Thr Gln Asp Lys Ile Lys Thr His Gly Ala Ala Leu Gln Cys Arg Ile
            340                 345                 350 acc acg gaa gat cca aac aac ggc ttc cgc cca gat acc gga act atc     1104
Thr Thr Glu Asp Pro Asn Asn Gly Phe Arg Pro Asp Thr Gly Thr Ile
        355                 360                 365 acc gcg tac cgc tca cca ggc gga gct ggc gtt cgt ctt gac ggt gca     1152
Thr Ala Tyr Arg Ser Pro Gly Gly Ala Gly Val Arg Leu Asp Gly Ala
    370                 375                 380 gct cag ctc ggt ggc gaa atc acc gca cac ttt gac tcc atg ctg gtg     1200
Ala Gln Leu Gly Gly Glu Ile Thr Ala His Phe Asp Ser Met Leu Val
385                 390                 395                 400 aaa atg acc tgc cgt ggt tcc gac ttt gaa act gct gtt gct cgt gca     1248
Lys Met Thr Cys Arg Gly Ser Asp Phe Glu Thr Ala Val Ala Arg Ala
                405                 410                 415 cag cgc gcg ttg gct gag ttc acc gtg tct ggt gtt gca acc aac att     1296
Gln Arg Ala Leu Ala Glu Phe Thr Val Ser Gly Val Ala Thr Asn Ile
            420                 425                 430 ggt ttc ttg cgt gcg ttg ctg cgg gaa gag gac ttc act tcc aag cgc     1344
Gly Phe Leu Arg Ala Leu Leu Arg Glu Glu Asp Phe Thr Ser Lys Arg
        435                 440                 445 atc gcc acc gga ttc att gcc gat cac ccg cac ctc ctt cag gct cca     1392
Ile Ala Thr Gly Phe Ile Ala Asp His Pro His Leu Leu Gln Ala Pro
    450                 455                 460 cct gct gat gat gag cag gga cgc atc ctg gat tac ttg gca gat gtc     1440
Pro Ala Asp Asp Glu Gln Gly Arg Ile Leu Asp Tyr Leu Ala Asp Val
465                 470                 475                 480 acc gtg aac aag cct cat ggt gtg cgt cca aag gat gtt gca gct cct     1488
Thr Val Asn Lys Pro His Gly Val Arg Pro Lys Asp Val Ala Ala Pro
                485                 490                 495 atc gat aag ctg cct aac atc aag gat ctg cca ctg cca cgc ggt tcc     1536
Ile Asp Lys Leu Pro Asn Ile Lys Asp Leu Pro Leu Pro Arg Gly Ser
            500                 505                 510 cgt gac cgc ctg aag cag ctt ggc cca gcc gcg ttt gct cgt gat ctc     1584
Arg Asp Arg Leu Lys Gln Leu Gly Pro Ala Ala Phe Ala Arg Asp Leu
        515                 520                 525
```

-continued

| | | |
|---|---|---|
| cgt gag cag gac gca ctg gca gtt act gat acc acc ttc cgc gat gca<br>Arg Glu Gln Asp Ala Leu Ala Val Thr Asp Thr Thr Phe Arg Asp Ala<br>530                                   535                             540 | | 1632 |
| cac cag tct ttg ctt gcg acc cga gtc cgc tca ttc gca ctg aag cct<br>His Gln Ser Leu Leu Ala Thr Arg Val Arg Ser Phe Ala Leu Lys Pro<br>545                             550                       555                     560 | | 1680 |
| gcg gca gag gcc gtc gca aag ctg act cct gag ctt ttg tcc gtg gag<br>Ala Ala Glu Ala Val Ala Lys Leu Thr Pro Glu Leu Leu Ser Val Glu<br>                       565                      570                       575 | | 1728 |
| gcc tgg ggc ggc gcg acc tac gat gtg gcg atg cgt ttc ctc ttt gag<br>Ala Trp Gly Gly Ala Thr Tyr Asp Val Ala Met Arg Phe Leu Phe Glu<br>                       580                        585                 590 | | 1776 |
| gat ccg tgg gac agg ctc gac gag ctg cgc gag gcg atg ccg aat gta<br>Asp Pro Trp Asp Arg Leu Asp Glu Leu Arg Glu Ala Met Pro Asn Val<br>595                               600                       605 | | 1824 |
| aac att cag atg ctg ctt cgc ggc cgc aac acc gtg gga tac acc ccg<br>Asn Ile Gln Met Leu Leu Arg Gly Arg Asn Thr Val Gly Tyr Thr Pro<br>610                             615                       620 | | 1872 |
| tac cca gac tcc gtc tgc cgc gcg ttt gtt aag gaa gct gcc agc tcc<br>Tyr Pro Asp Ser Val Cys Arg Ala Phe Val Lys Glu Ala Ala Ser Ser<br>625                             630                      635                640 | | 1920 |
| ggc gtg gac atc ttc cgc atc ttc gac gcg ctt aac gac gtc tcc cag<br>Gly Val Asp Ile Phe Arg Ile Phe Asp Ala Leu Asn Asp Val Ser Gln<br>                       645                      650                    655 | | 1968 |
| atg cgt cca gca atc gac gca gtc ctg gag acc aac acc gcg gta gcc<br>Met Arg Pro Ala Ile Asp Ala Val Leu Glu Thr Asn Thr Ala Val Ala<br>         660                       665                      670 | | 2016 |
| gag gtg gct atg gct tat tct ggt gat ctc tct gat cca aat gaa aag<br>Glu Val Ala Met Ala Tyr Ser Gly Asp Leu Ser Asp Pro Asn Glu Lys<br>         675                       680                      685 | | 2064 |
| ctc tac acc ctg gat tac tac cta aag atg gca gag gag atc gtc aag<br>Leu Tyr Thr Leu Asp Tyr Tyr Leu Lys Met Ala Glu Glu Ile Val Lys<br>690                           695                       700 | | 2112 |
| tct ggc gct cac atc ttg gcc att aag gat atg gct ggt ctg ctt cgc<br>Ser Gly Ala His Ile Leu Ala Ile Lys Asp Met Ala Gly Leu Leu Arg<br>705                             710                      715                 720 | | 2160 |
| cca gct gcg gta acc aag ctg gtc acc gca ctg cgt gaa ttc gat<br>Pro Ala Ala Val Thr Lys Leu Val Thr Ala Leu Arg Arg Glu Phe Asp<br>                       725                      730                    735 | | 2208 |
| ctg cca gtg cac gtg cac acc cac gac act gcg ggt ggc cag ctg gca<br>Leu Pro Val His Val His Thr His Asp Thr Ala Gly Gly Gln Leu Ala<br>                       740                      745                    750 | | 2256 |
| acc tac ttt gct gca gct caa gct ggt gca gat gct gtt gac ggt gct<br>Thr Tyr Phe Ala Ala Ala Gln Ala Gly Ala Asp Ala Val Asp Gly Ala<br>755                             760                       765 | | 2304 |
| tcc gca cca ctg tct ggc acc acc tcc cag cca tcc ctg tct gcc att<br>Ser Ala Pro Leu Ser Gly Thr Thr Ser Gln Pro Ser Leu Ser Ala Ile<br>770                           775                       780 | | 2352 |
| gtt gct gca ttc gcg cac acc cgt cgc gat acc ggt ttg agc ctc gag<br>Val Ala Ala Phe Ala His Thr Arg Arg Asp Thr Gly Leu Ser Leu Glu<br>785                           790                      795                800 | | 2400 |
| gct gtt tct gac ctc gag ccg tac tgg gaa gca gtg cgc gga ctg tac<br>Ala Val Ser Asp Leu Glu Pro Tyr Trp Glu Ala Val Arg Gly Leu Tyr<br>                       805                      810                 815 | | 2448 |
| ctg cca ttt gag tct gga acc cca ggc cca acc ggt cgc gtc tac cgc<br>Leu Pro Phe Glu Ser Gly Thr Pro Gly Pro Thr Gly Arg Val Tyr Arg<br>         820                       825                      830 | | 2496 |
| cac gaa atc cca ggc gga cag ttg tcc aac ctg cgt gca cag gcc acc<br>His Glu Ile Pro Gly Gly Gln Leu Ser Asn Leu Arg Ala Gln Ala Thr<br>         835                       840                    845 | | 2544 |

```
gca ctg ggc ctt gcg gat cgt ttc gaa ctc atc gaa gac aac tac gca    2592
Ala Leu Gly Leu Ala Asp Arg Phe Glu Leu Ile Glu Asp Asn Tyr Ala
    850                 855                 860 gcc gtt aat gag atg ctg gga cgc cca acc aag gtc acc cca tcc tcc    2640
Ala Val Asn Glu Met Leu Gly Arg Pro Thr Lys Val Thr Pro Ser Ser
865                 870                 875                 880 aag gtt gtt ggc gac ctc gca ctc cac ctc gtt ggt gcg ggt gtg gat    2688
Lys Val Val Gly Asp Leu Ala Leu His Leu Val Gly Ala Gly Val Asp
                885                 890                 895 cca gca gac ttt gct gcc gat cca caa aag tac gac atc cca gac tct    2736
Pro Ala Asp Phe Ala Ala Asp Pro Gln Lys Tyr Asp Ile Pro Asp Ser
            900                 905                 910 gtc atc gcg ttc ctg cgc ggt gag ctt ggt aac cct cca ggt ggc tgg    2784
Val Ile Ala Phe Leu Arg Gly Glu Leu Gly Asn Pro Pro Gly Gly Trp
        915                 920                 925 cca gag cca ctg cgc acc cgc gca ctg gaa ggc cgc tcc gaa ggc aag    2832
Pro Glu Pro Leu Arg Thr Arg Ala Leu Glu Gly Arg Ser Glu Gly Lys
    930                 935                 940 gca cct ctg acg gaa gtt cct gag gaa gag cag gcg cac ctc gac gct    2880
Ala Pro Leu Thr Glu Val Pro Glu Glu Glu Gln Ala His Leu Asp Ala
945                 950                 955                 960 gat gat tcc aag gaa cgt cgc aat agc ctc aac cgc ctg ctg ttc ccg    2928
Asp Asp Ser Lys Glu Arg Arg Asn Ser Leu Asn Arg Leu Leu Phe Pro
                965                 970                 975 aag cca acc gaa gag ttc ctc gag cac cgt cgc cgc ttc ggc aac acc    2976
Lys Pro Thr Glu Glu Phe Leu Glu His Arg Arg Arg Phe Gly Asn Thr
            980                 985                 990 tct gcg ctg gat gat cgt gaa ttc ttc tac ggc ctg gtc gaa ggc cgc    3024
Ser Ala Leu Asp Asp Arg Glu Phe Phe Tyr Gly Leu Val Glu Gly Arg
        995                 1000                1005 gag act ttg atc cgc ctg cca gat gtg cgc acc cca ctg ctt gtt        3069
Glu Thr Leu Ile Arg Leu Pro Asp Val Arg Thr Pro Leu Leu Val
    1010                1015                1020 cgc ctg gat gcg atc tct gag cca gac gat aag ggt atg cgc aat        3114
Arg Leu Asp Ala Ile Ser Glu Pro Asp Asp Lys Gly Met Arg Asn
    1025                1030                1035 gtt gtg gcc aac gtc aac ggc cag atc cgc cca atg cgt gtg cgt        3159
Val Val Ala Asn Val Asn Gly Gln Ile Arg Pro Met Arg Val Arg
    1040                1045                1050 gac cgc tcc gtt gag tct gtc acc gca acc gca gaa aag gca gat        3204
Asp Arg Ser Val Glu Ser Val Thr Ala Thr Ala Glu Lys Ala Asp
    1055                1060                1065 tcc tcc aac aag ggc cat gtt gct gca cca ttc gct ggt gtt gtc        3249
Ser Ser Asn Lys Gly His Val Ala Ala Pro Phe Ala Gly Val Val
    1070                1075                1080 acc gtg act gtt gct gaa ggt gat gag gtc aag gct gga gat gca        3294
Thr Val Thr Val Ala Glu Gly Asp Glu Val Lys Ala Gly Asp Ala
    1085                1090                1095 gtc gca atc atc gag gct atg aag atg gaa gca aca atc act gct        3339
Val Ala Ile Ile Glu Ala Met Lys Met Glu Ala Thr Ile Thr Ala
    1100                1105                1110 tct gtt gac ggc aaa atc gat cgc gtt gtg gtt cct gct gca acg        3384
Ser Val Asp Gly Lys Ile Asp Arg Val Val Val Pro Ala Ala Thr
    1115                1120                1125 aag gtg gaa ggt ggc gac ttg atc gtc gtc gtt tcc taa                3423
Lys Val Glu Gly Gly Asp Leu Ile Val Val Val Ser
    1130                1135                1140

<210> SEQ ID NO 65
<211> LENGTH: 1140
<212> TYPE: PRT
```

<213> ORGANISM: Corynebacterium glutamicum

<400> SEQUENCE: 65

```
Val Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
```

```
                    405                 410                 415
Gln Arg Ala Leu Ala Glu Phe Thr Val Ser Gly Val Thr Asn Ile
                420                 425                 430

Gly Phe Leu Arg Ala Leu Leu Arg Glu Glu Asp Phe Thr Ser Lys Arg
                435                 440                 445

Ile Ala Thr Gly Phe Ile Ala Asp His Pro His Leu Leu Gln Ala Pro
                450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
                500                 505                 510

Arg Asp Arg Leu Lys Gln Leu Gly Pro Ala Ala Phe Ala Arg Asp Leu
                515                 520                 525

Arg Glu Gln Asp Ala Leu Ala Val Thr Asp Thr Thr Phe Arg Asp Ala
                530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
                580                 585                 590

Asp Pro Trp Asp Arg Leu Asp Glu Leu Arg Glu Ala Met Pro Asn Val
                595                 600                 605

Asn Ile Gln Met Leu Leu Arg Gly Arg Asn Thr Val Gly Tyr Thr Pro
                610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
                675                 680                 685

Leu Tyr Thr Leu Asp Tyr Tyr Leu Lys Met Ala Glu Glu Ile Val Lys
                690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
                740                 745                 750

Thr Tyr Phe Ala Ala Ala Gln Ala Gly Ala Asp Ala Val Asp Gly Ala
                755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
                820                 825                 830
```

-continued

| | | | | | | | | | | | | |
|---|---|---|---|---|---|---|---|---|---|---|---|---|
|His|Glu|Ile|Pro|Gly|Gly|Gln|Leu|Ser|Asn|Leu|Arg|Ala|Gln|Ala|Thr|
| |835| | | | |840| | | | |845| | | | |

Ala Leu Gly Leu Ala Asp Arg Phe Glu Leu Ile Glu Asp Asn Tyr Ala
     850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
             885                 890                 895

Pro Ala Asp Phe Ala Ala Asp Pro Gln Lys Tyr Asp Ile Pro Asp Ser
         900                 905                 910

Val Ile Ala Phe Leu Arg Gly Glu Leu Gly Asn Pro Pro Gly Gly Trp
         915                 920                 925

Pro Glu Pro Leu Arg Thr Arg Ala Leu Glu Gly Arg Ser Glu Gly Lys
     930                 935                 940

Ala Pro Leu Thr Glu Val Pro Glu Glu Glu Gln Ala His Leu Asp Ala
945                 950                 955                 960

Asp Asp Ser Lys Glu Arg Arg Asn Ser Leu Asn Arg Leu Leu Phe Pro
             965                 970                 975

Lys Pro Thr Glu Glu Phe Leu Gly His Arg Arg Arg Phe Gly Asn Thr
         980                 985                 990

Ser Ala Leu Asp Asp Arg Glu Phe Phe Tyr Gly Leu Val Glu Gly Arg
     995                 1000                1005

Glu Thr Leu Ile Arg Leu Pro Asp Val Arg Thr Pro Leu Leu Val
    1010                1015                1020

Arg Leu Asp Ala Ile Ser Glu Pro Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Pro Ala Ala Thr
    1115                1120                1125

Lys Val Glu Gly Gly Asp Leu Ile Val Val Val Ser
    1130                1135                1140

METHOD FOR PRODUCING L-AMINO ACID

This application is a continuation application under 35 U.S.C. §120 of PCT Patent Application No. PCT/JP2007/051837, filed Jan. 29, 2007, and claims priority under 35 U.S.C. §119 to Japanese Patent Application No. 2006-019562, filed Jan. 27, 2006, both of which are incorporated by reference. The Sequence Listing filed electronically herewith is also hereby incorporated by reference in its entirety (File Name: US-320_Seq_List_Copy__1; File Size: 207 KB; Date Created: Jul. 25, 2008).

BACKGROUND OF THE INVENTION

1. Field of the Invention

The present invention relates to a method for efficiently producing L-amino acids such as L-glutamic acid, L-glutamine, L-proline, L-arginine, L-leucine, and L-cysteine by fermentation.

2. Brief Description of the Related Art

L-amino acids are typically produced by various fermentation methods using L-amino acid-producing coryneform bacteria, including those belonging to the genus *Brevibacterium, Corynebacterium, Microbacterium*, or mutant strains thereof (Amino Acid Fermentation, Japan Scientific Societies Press, p. 195-215, 1986). Other bacterial strains have been used to produce L-amino acids by fermentation, and examples include microorganisms belonging to the genus *Bacillus, Streptomyces*, or *Penicillium* (U.S. Pat. No. 3,220,929), bacteria belonging to the genus *Pseudomonas, Arthrobacter, Serratia*, or *Candida* (U.S. Pat. No. 3,563,857), bacteria belonging to the genus *Bacillus, Pseudomonas, Serratia*, or *Aerobacter aerogenes* (currently, *Enterobacter aerogenes*) (JP 32-9393 B), mutant strains of *Escherichia coli* (U.S. Pat. No. 5,378,616). Furthermore, methods for producing an L-amino acids using bacteria belonging to the genus *Klebsiella, Erwinia, Pantotea*, or *Enterobacter* (EP 955368 A, EP 952221 B, and EP 999282 A) have also been disclosed.

Various methods to increase the L-amino acid-producing ability of bacteria by enhancing activities of L-amino acid biosynthetic enzymes using recombinant DNA techniques have also been disclosed. For example, it has been reported that introducing a gene encoding citrate synthase derived from *Escherichia coli* or *Corynebacterium glutamicum* into a bacterium belonging to the genus *Corynebacterium* or *Brevibacterium* is effective to enhance the L-amino acid-producing ability of the bacterium (JP 07-121228 B). In addition, it has been reported that introducing a citrate synthase gene derived from a coryneform bacterium into an enterobacterium belonging to the genus *Enterobacter, Klebsiella, Serratia, Erwinia*, or *Escherichia* is effective to enhance L-glutamic acid-producing ability (EP 999282 A).

Phosphotransacetylase is an enzyme which is involved in acetic acid metabolism. In *Escherichia coli*, this enzyme plays a role in the reaction which produces acetyl phosphate from acetyl-CoA and phosphate, which is part of the primary pathway for producing acetic acid. Furthermore, it is known that in *Corynebacterium glutamicum*, phosphotransacetylase activity increases upon production of acetyl-CoA by assimilating acetic acid, and the activity is negatively regulated by the transcription factor RamB (Microbiology 1999 503-513, Journal of Bacteriology 2004 vol. 186, No. 9 p 2798-2809).

Examples of known methods of fermentative production of a useful material using a bacterium in which phosphotransacetylase activity is enhanced include production of poly-β-hydroxyalkanoate copolymer (U.S. Pat. No. 5,891,686 and U.S. Pat. No. 5,569,595), and production of ethanol (WO 2003/078643). Furthermore, an enzymatic method of producing a sulfur-containing L-amino acid using phosphotransacetylase has been disclosed (JP 09-009982 A). However, enhancing phosphotransacetylase activity in the breeding of L-amino acid-producing bacteria has not been reported, and the relationship between phosphotransacetylase activity and L-amino acid productivity has not been elucidated.

SUMMARY OF THE INVENTION

An aspect of the present invention is to provide a novel fermentation method for producing L-amino acids such as L-glutamic acid, L-glutamine, L-proline, L-arginine, L-leucine, and L-cysteine. It has been found that L-amino acids such as L-glutamic acid, L-glutamine, L-proline, L-arginine, L-leucine, and L-cysteine can be efficiently produced by culturing an L-amino acid-producing bacterium which has been modified to enhance phosphotransacetylase activity.

It is an aspect of the present invention to provide a method for producing an L-amino acid comprising culturing in a medium an L-amino acid-producing bacterium which has been modified to enhance phosphotransacetylase activity, and collecting the L-amino acid from the medium or the bacterium.

It is another aspect of the present invention to provide the method as described above, wherein the phosphotransacetylase activity is enhanced by a method selected from the group consisting of: A) increasing the copy number of the gene encoding phosphotransacetylase, B) modifying an expression regulatory sequence of the gene encoding phosphotransacetylase, and C) combinations thereof.

It is another aspect of the present invention to provide the method as described above, wherein the gene encoding phosphotransacetylase is a DNA selected from the group consisting of:

(a) a DNA comprising nucleotides 1214 to 2641 of SEQ ID NO: 34, (b) a DNA comprising the nucleotide sequence of SEQ ID NO: 40, (c) a DNA which hybridizes with a nucleotide sequence which is complementary to the nucleotide sequence of nucleotides 1214 to 2641 of SEQ ID NO: 34, wherein said DNA hybridizes under stringent conditions and encodes a protein that has phosphotransacetylase activity, and (d) a DNA which hybridizes with a nucleotide sequence which is complementary to the nucleotide sequence of SEQ ID NO: 40, wherein said DNA hybridizes under stringent conditions and encodes a protein that has phosphotransacetylase activity.

It is another aspect of the present invention to provide the method as described above, wherein the phosphotransacetylase activity is enhanced by disrupting a ramB gene.

It is another aspect of the present invention to provide the method as described above, wherein the bacterium is further modified to enhance the activity of a protein selected from the group consisting of D-xylose 5-phosphate-phosphoketolase, fructose 6-phosphate phosphoketolase, and combinations thereof.

It is another aspect of the present invention to provide the method as described above, wherein the bacterium is further modified to enhance pyruvate carboxylase activity.

It is another aspect of the present invention to provide the method as described above, wherein the bacterium is further modified to enhance phosphoenolpyruvate carboxylase activity.

It is another aspect of the present invention to provide the method as described above, wherein the bacterium is selected from the group consisting of a coryneform bacterium, *Pantoea* bacterium, *Enterobacter* bacterium, and *Escherichia* bacterium.

It is another aspect of the present invention to provide the method as described above, wherein the L-amino acid is selected from the group consisting of L-glutamic acid, L-glutamine, L-proline, L-arginine, L-leucine, and L-cysteine.

DESCRIPTION OF THE PREFERRED EMBODIMENTS

<1-1> Bacterium of the Present Invention

Figure 1:
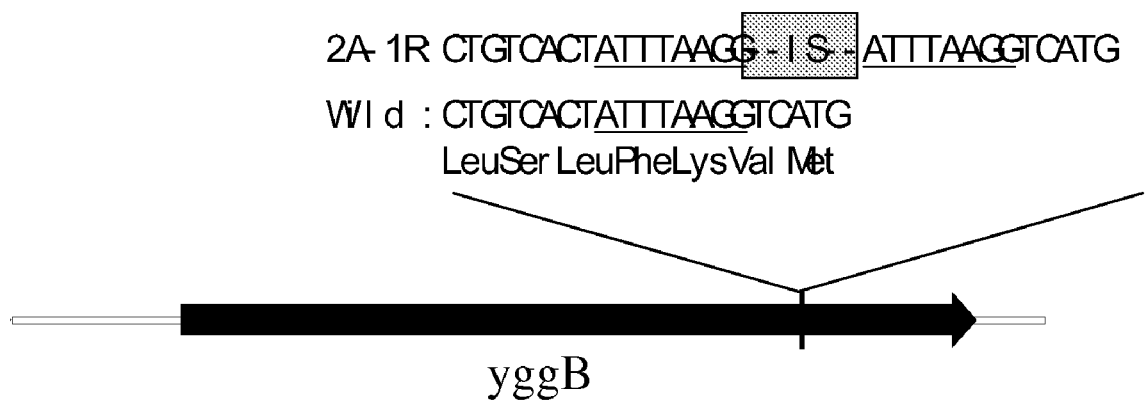
FIG. 1 shows an IS-inserted site in the mutant-type yggB gene.

The bacterium used in the production method of the present invention (also referred to as the bacterium of the present invention) has an L-amino acid-producing ability and has been modified to enhance phosphotransacetylase activity. The bacterium of the present invention can be obtained by modifying a bacterium having an L-amino acid-producing ability (i.e., a parental strain) so that the phosphotransacetylase activity is enhanced. The bacterium of the present invention may have a native L-amino acid-producing ability or may be bred to have an L-amino acid-producing ability.

Herein, the "L-amino acid-producing ability" means an ability to produce an L-amino acid in an amount that allows for collection of the L-amino acid from the bacterial cells or the medium. Preferably, it means an ability to produce a larger amount of the L-amino acid as compared to a wild-type or non-modified strain which is cultured under the same conditions.

Examples of the L-amino acids to be produced include L-lysine, L-glutamic acid, L-threonine, L-valine, L-leucine, L-isoleucine, L-serine, L-aspartic acid, L-asparagine, L-glutamine, L-arginine, L-cysteine (cystine), L-methionine, L-phenylalanine, L-tryptophan, L-tyrosine, L-glycine, L-alanine, L-proline, L-ornithine, L-citrulline, and L-homoserine. L-amino acids derived from acetyl-CoA are preferable, and L-glutamic acid, L-glutamine, L-proline, L-arginine, L-leucine, and L-cysteine are preferable.

Examples of the bacterium of the present invention include, but are not limited to, bacteria belonging to the Enterobacteriaceae family, including those belonging to the genus *Escherichia*, *Pantoea*, *Enterobacter*, or the like, coryneform bacteria such as *Corynebacterium glutamicum* and *Brevibacterium lactofermentum*, and bacteria belonging to the genus *Bacillus*, such as *Bacillus subtilis*.

In the present invention, the "coryneform bacterium" includes bacteria previously classified as *Brevibacterium*, but now are classified as *Corynebacterium* (Int. J. Syst. Bacteriol., 41, 255 (1991)), as well as bacteria belonging to the genus *Brevibacterium*, which are highly-related to the genus *Corynebacterium*. Examples of such bacteria include the following:

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes*
*Brevibacterium album*
*Brevibacterium selinum*
*Microbacterium ammoniaphilum*

Specifically, the following strains are exemplified:
*Corynebacterium acetoacidophilum* ATCC13870
*Corynebacterium acetoglutamicum* ATCC15806
*Corynebacterium alkanolyticum* ATCC21511
*Corynebacterium callunae* ATCC15991
*Corynebacterium glutamicum* ATCC13020, ATCC13032, ATCC13060
*Corynebacterium lilium* ATCC15990
*Corynebacterium melassecola* ATCC17965
*Corynebacterium thermoaminogenes* AJ12340 (FERM BP-1539)
*Corynebacterium herculis* ATCC13868
*Brevibacterium divaricatum* ATCC14020
*Brevibacterium flavum* ATCC13826, ATCC14067
*Brevibacterium immariophilum* ATCC14068
*Brevibacterium lactofermentum* ATCC13869 (*Corynebacterium glutamicum* ATCC13869)
*Brevibacterium roseum* ATCC13825
*Brevibacterium saccharolyticum* ATCC14066
*Brevibacterium thiogenitalis* ATCC19240
*Corynebacterium ammoniagenes* ATCC6871, ATCC6872
*Brevibacterium album* ATCC15111
*Brevibacterium selinum* ATCC15112
*Microbacterium ammoniaphilum* ATCC15354

These strains are available from the American Type Culture Collection (ATCC: address: P.O. Box 1549, Manassas, Va. 20108, 1, United States of America). That is, accession numbers are given to each of the strains, and the strains can be ordered using these numbers (http://www.atcc.org/). The accession numbers for the strains are listed in the catalogue of the American Type Culture Collection. The AJ12340 strain was deposited at the National Institute of Bioscience and Human-Technology, Agency of Industrial Science and Technology (currently, International Patent Organism Depositary, National Institute of Advanced Industrial Science and Technology) (Central 6, 1-1-1 Higashi, Tsukuba, Ibaraki 305-5466, Japan) on Oct. 27, 1987 and given an accession number of FERM BP-1539 under the provisions of Budapest Treaty.

Bacteria belonging to the Enterobacteriaceae family are not particularly limited as long as they have an L-amino acid-producing ability, and include those belonging to the genus *Escherichia, Enterobacter, Pantoea, Klebsiella, Serratia, Erwinia, Salmonella, Morganella*, or the like. Bacteria belonging to the Enterobacteriaceae family based on the classification described in the NCBI (National Center for Biotechnology Information) database (http://www.ncbi.nlm.nih.gov/htbin-post/Taxonomy/wgetorg?mode=Tree&id=1236&1v1=3&keep=1&srchmode=1&unlock) can be used. Among these, bacteria belonging to the genus *Escherichia, Enterobacter*, or *Pantoea* are preferable.

The parent strain of *Escherichia* bacteria which can be used to obtain the bacterium of the present invention is not particularly limited, and specifically, bacteria listed in Neidhardt et al. (*Escherichia coli* and *Salmonella Typhimurium*, American Society for Microbiology, Washington D.C., 1029 table 1) may be used. Among these, *Escherichia coli* is preferable. Specific examples of *Escherichia coli* include *Escherichia coli* W3110 strain (ATCC 27325) and *Escherichia coli* MG1655 strain (ATCC 47076), which are derived from the prototype wild-type K12 strain.

Examples of *Enterobacter* bacteria include *Enterobacter agglomerans* and *Enterobacter aerogenes*, and examples of *Pantoea* bacteria include *Pantoea ananatis*. Recently, *Enterobacter agglomerans* was reclassified in some cases as *Pantoea agglomerans, Pantoea ananatis*, or *Pantoea stewartii* based on an analysis of the nucleotide sequence of 16S rRNA. Therefore, the bacteria of the present invention may belong to the genus *Enterobacter* or *Pantoea*, as long as they are classified in the Enterobacteriaceae family. When *Pantoea ananatis* is bred using a genetic engineering technique, *Pantoea ananatis* AJ13355 (FERM BP-6614), AJ13356 strain (FERM BP-6615), AJ13601 (FERM BP-7207), and derivatives thereof may be used. These strains were identified and deposited as *Enterobacter agglomerans* at the time of isolation, but then reclassified as *Pantoea ananatis* based on an analysis of the nucleotide sequence of 16S rRNA.

Hereinafter, methods for imparting an L-amino acid-producing ability to such a bacterium as described above will be described.

In order to impart an L-amino acid-producing ability, methods may be used which are typically used in conventional breeding of amino acid-producing bacteria such as a coryneform bacterium or an *Escherichia* bacterium. Such methods include acquisition of nutrient-auxotrophic mutant strains, analogue-resistant strains, and metabolic regulation mutant strains, as well as breeding recombinant strains to have enhanced expression of genes encoding L-amino acid biosynthetic enzymes (Amino Acid Fermentation, Japan Scientific Societies Press, first edition publication: May 30, 1986, p. 77 to 100). Nutrient-auxotrophic mutations, analogue-resistant mutations, and metabolic regulation mutations may be imparted singly or in combination during the breeding of L-amino acid-producing bacteria. Furthermore, activities of one or more of the L-amino acid biosynthetic enzymes may be enhanced. Even furthermore, nutrient-auxotrophic mutations, analogue resistant mutations, and metabolic regulation mutations may be imparted in combination with enhancing the activities of the L-amino acid biosynthetic enzymes.

Nutrient-auxotrophic mutant strains, analogue-resistant strains, and metabolic regulation mutant strains that have an L-amino acid-producing ability can be obtained as follows. That is, a parent strain or a wild-type strain is subjected to a general mutation treatment, i.e., irradiation with X-ray or ultraviolet ray, or a subjected to an agent such as N-methyl-N'-nitro-N-nitrosoguanidine. The strain that exhibits nutrient-auxotrophy, analogue-resistance, or a metabolic regulation mutation and has an L-amino acid-producing ability is selected from the mutated strains.

In addition, an L-amino acid-producing bacterium can be obtained by enhancing an activity of an L-amino acid biosynthetic enzyme via genetic recombination. However, the L-amino acid-producing ability may be a native property to the wild-type bacterium. Furthermore, as described below, the L-amino acid-producing ability may be imparted by enhancing the expression of the phosphotransacetylase gene.

Hereinafter, methods of imparting an L-glutamic acid-producing ability and bacteria imparted with L-glutamic acid-producing ability will be described as examples.

In order to impart and/or enhance L-glutamic acid-producing ability in a bacterium, the expression of a gene encoding an enzyme involved in L-glutamic acid biosynthesis can be enhanced. Enzymes involved in L-glutamic acid biosynthesis include glutamate dehydrogenase, glutamine synthetase, glutamate synthase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phosphate dehydrogenase, triosephosphate isomerase, fructosebisphosphate aldolase, phosphofructokinase, and glucosephosphate isomerase.

Gene expression can be enhanced by transforming the bacterium with a plasmid containing the desired gene and sequences required for replication of the plasmid, integrating the gene by homologous recombination, conjugation, gene transfer, or the like into the chromosome of the bacterium, or introducing a mutation into the promoter region of the gene (WO 95/34672).

When transforming the desired gene into a bacterium using a plasmid or integrating the gene into the chromosome, a promoter for expressing the gene may be any promoter as long as it functions in the chosen host bacterium, and it may be the native promoter of the gene or a heterologous promoter.

The expression level of a gene can be increased by selecting a promoter which is known to be strong in the chosen host bacterium, or by modifying the −35 region or the −10 region of the promoter to be close to a consensus sequence.

Bacteria modified to have enhanced expression of a citrate synthase gene, an isocitrate dehydrogenase, a pyruvate dehydrogenase gene and/or a glutamate dehydrogenase gene include those described in WO 00/18935 and EP 1010755A.

L-glutamic acid-producing ability can be imparted by decreasing or eliminating an activity of an enzyme that catalyzes a reaction which branches off from the L-glutamic acid biosynthetic pathway, and leads to a compound other than L-glutamic acid. Such enzymes include isocitrate lyase, α-ketoglutarate dehydrogenase, acetohydroxyacid synthase, acetolactate synthase, formate acetyltransferase, lactate dehydrogenase, glutamate decarboxylase, and 1-pyrroline dehydrogenase.

For example, α-ketoglutarate dehydrogenase activity can be decreased by using the sucA (odhA) gene that encodes the E1o subunit of α-ketoglutarate dehydrogenase. Strains having decreased α-ketoglutarate dehydrogenase activity are shown below.

*Brevibacterium lactofermentum* ΔS strain (WO 95/34672)
*Brevibacterium lactofermentum* AJ12821 (FERM BP-4172; FR 9401748 A)
*Brevibacterium flavum* AJ12822 (FERM BP-4173; FR 9401748 A)
*Corynebacterium glutamicum* AJ12823 (FERM BP-4174; FR 9401748 A)
*Pantoea ananatis* AJ13601 (FERM BP-7207)
*Klebsiella planticola* AJ13410 strain (FERM BP-6617)
*Pantoea ananatis* AJ13355 (FERM BP-6614)

To decrease or eliminate the activity of such an enzyme, a mutation may be introduced into the gene encoding the enzyme on the chromosome using a general mutation treatment. For example, the gene may be disrupted by gene recombination, or by modifying an expression regulatory sequence such as a promoter and a Shine-Dalgarno (SD) sequence so that the gene expression or translation is decreased. In addition, amino acid substitution (missense mutation), a stop codon (nonsense mutation), a frameshift mutation that adds/deletes one or two nucleotides into the region encoding the enzymes on the chromosome may be introduced, or the gene or a part thereof may be deleted (Journal of Biological Chemistry 272: 8611-8617 (1997). Also, the activity of the enzyme may also be decreased or eliminated by replacing the wild-type gene on the chromosome with a mutant gene in which the coding region is deleted by homologous recombination, or by introducing a transposon or an IS factor into the gene.

For example, the following method can be used to introduce a mutation that decreases or eliminates the activity of the above-described enzyme by homologous recombination. A mutant gene is prepared by modifying a partial sequence of the target gene so that the encoded enzyme is not produced, and a host bacterium is transformed with the DNA containing the mutant gene. This causes recombination between the mutant gene and the gene on the chromosome, thereby replacing the gene on the chromosome with the mutant gene. Such site-specific mutagenesis by gene substitution using homologous recombination is known, and can be achieved by using a linear DNA or a plasmid containing a temperature-sensitive replication origin (U.S. Pat. No. 6,303,383 or JP 05-007491 A). Also, site-specific mutagenesis by gene substitution using homologous recombination may also be achieved by using a plasmid which is unable to replicate in the chosen host bacterium.

Examples of temperature-sensitive plasmids in coryneform bacteria include p48K, pSFKT2 (U.S. Pat. No. 6,303, 383), and pHSC4 (FR 1992-2667875 A and JP 05-7491 A). These plasmids can autonomously replicate at 25° C. but cannot autonomously replicate at 37° C. *Escherichia coli* AJ12571 transformed with pHSC4 was deposited at the National Institute of Bioscience and Human-Technology, Agency of Industrial Science and Technology (currently, International Patent Organism Depositary, National Institute of Advanced Industrial Science and Technology, Central 6, 1-1-1 Higashi, Tsukuba, Ibaraki 305-5466, Japan) on Oct. 11, 1990 and given an accession number of FERM P-11763, and then converted to an international deposit under the provisions of Budapest Treaty on Aug. 26, 1991 and given an accession number of FERM BP-3524.

Moreover, L-glutamic acid-producing ability may be imparted to a host bacterium by amplifying the yggB gene (NCgl 1221; NP_600492. [gi:19552490]; SEQ ID NO: 32) or by introducing a yggB gene containing a mutation in its coding region (WO2006/070944). The following gene may be used as the mutant yggB gene.

(1) Mutation in the C-Terminal Region

This mutation is introduced into the region encoding the amino acid sequence of amino acids 419-533 of SEQ ID NO: 33. This may be any mutation as long as it is introduced into the nucleotide sequence encoding the above-described region, and an insertion mutation, including insertion of an insertion sequence (hereinafter, referred to as IS), or a transposon, is preferable. The insertion mutation may result in an amino acid substitution (missense mutation), a frameshift, or a stop codon (nonsense mutation). SEQ ID NOS: 7 and 8 show the nucleotide sequence of the mutant yggB gene containing a transposable element (IS) in the C-terminal region and the amino acid sequence encoded by the mutant gene, respectively.

Meanwhile, examples of the mutation in the C-terminal region include replacing a proline in the sequence of amino acids 419-533 of SEQ ID NO: 33 with another amino acid.

(2) Mutation in a Transmembrane Region

The Ygg protein encoded by the yggB gene is predicted to have five transmembrane regions, and these transmembrane regions correspond to amino acids 1-23 (first transmembrane region), 25-47 (second transmembrane region), 62-84 (third transmembrane region), 86-108 (fourth transmembrane region), and 110-132 (fifth transmembrane region) in the wild-type YggB protein (SEQ ID NO: 33). Mutations in the transmembrane regions preferably cause substitution, deletion, addition, insertion, or inversion of one or several amino acids without causing a frameshift or a translation termination.

Examples of mutations in the transmembrane region include inserting one or several amino acids between the leucine at position 14 and the tryptophan at position 15 in the amino acid sequence of SEQ ID NO: 33, replacing the alanine at position 100 with another amino acid, and replacing the alanine at position 111 with another amino acid.

Another method for imparting and/or enhancing an L-glutamic acid-producing ability is to impart resistance to an organic acid analogue, a respiratory chain inhibitor, etc., and also to impart sensitivity to a cell-wall synthesis inhibitor. More specifically, these methods include imparting resistance to monofluoroacetic acid (JP 50-113209 A), adenine, thymine (JP 57-065198 A), malonic acid (JP 52-038088 A), benzopyrones or naphthoquinones (JP 56-1889 A), HOQNO (JP 56-140895 A), α-ketomalonic acid (JP 57-2689 A), or guanidine (JP 56-35981 A). Also, these methods include attenuating urease (JP 52-038088 A), and imparting sensitivity to penicillin (JP 4-88994 A).

Specific examples of such resistant bacteria include:

*Brevibacterium flavum* AJ3949 (FERM BP-2632; JP 50-113209 A)

*Corynebacterium glutamicum* AJ11628 (FERM P-5736; JP 57-065198 A)

*Brevibacterium flavum* AJ11355 (FERM P-5007; JP 56-1889 A)

*Corynebacterium glutamicum* AJ11368 (FERM P-5020; JP 56-1889 A)

*Brevibacterium flavum* AJ11217 (FERM P-4318; JP 57-2689 A)

*Corynebacterium glutamicum* AJ11218 (FERM P-4319; JP 57-2689 A)

*Brevibacterium flavum* AJ11564 (FERM P-5472; JP 56-140895 A)

*Brevibacterium flavum* AJ11439 (FERM P-5136; JP 56-35981 A)

*Corynebacterium glutamicum* H7684 (FERM BP-3004; JP 04-88994 A)

*Brevibacterium lactofermentum* AJ11426 (FERM P-5123; JP 56-048890 A)

*Corynebacterium glutamicum* AJ11440 (FERM P-5137; JP 56-048890 A)

*Brevibacterium lactofermentum* AJ11796 (FERM P-6402; JP 58-158192 A)

Bacteria imparted with an L-glutamine-producing ability include a bacterium having enhanced glutamate dehydrogenase activity, a bacterium having enhanced glutamine synthase (glnA) activity, and a bacterium belonging to the Enterobacteriaceae family having a disrupted glutaminase gene (EP 1229121 A and EP 1424398 A). The glutamine synthase activity may be enhanced by disrupting the glutamine adenylyltransferase gene (glnE) or by disrupting the gene encoding the PII regulatory protein (glnB). In addition, a preferable L-glutamine-producing bacterium includes an *Escherichia* bacterium having a mutant glutamine synthase in which the tyrosine at position 397 has been replaced with another amino acid (US Patent Publication 2003-0148474).

Another method of imparting and/or enhancing an L-glutamine-producing ability includes imparting resistance to 6-diazo-5-oxo-norleucine (JP 03-232497 A), imparting resistance to purine analogue and methionine sulfoxide (JP 61-202694 A), and imparting resistance to α-ketomaleic acid (JP 56-151495 A). Specific examples of a coryneform bacterium having an L-glutamine-producing ability include:

Brevibacterium flavum AJ11573 (FERM P-5492; JP 56-161495 A)

Brevibacterium flavum AJ11576 (FERM BP-10381; JP 56-161495 A)

Brevibacterium flavum AJ12212 (FERM P-8123; JP 61-202694 A)

Bacteria having an L-proline-producing ability include a bacterium harboring γ-glutamyl kinase which is not subject to feedback inhibition by L-proline and a bacterium in which the L-proline degradation system is attenuated. A method of modifying a bacterium using a DNA encoding γ-glutamyl kinase not subject to feedback inhibition by L-proline is disclosed in Dandekar, A. M., Uratsu, S. L., J. Bacteriol., 170, 12, 5943-5 (1988). Also, a bacterium with an attenuated L-proline degradation system is obtained by introducing a mutation into the proline dehydrogenase gene that results in decreased enzymatic activity. Specific examples of a bacterium having an L-proline-producing ability include *Escherichia coli* NRRL B-12403, NRRL B-12404 (GB 2075056), and VKPM B-8012 (US Patent 2002-0058315). Examples of a mutant plasmid for introducing such a mutation include the mutant plasmid disclosed in DE 3127361 B, and the mutant plasmid disclosed by Bloom et al. (The 15th Miami Winter Symposium, 1983, p. 34).

Preferable L-proline-producing bacteria include *Escherichia coli* 702 (VKPM B-8011), which is resistant to 3,4-dehydroxyproline and azatidine-2-carboxylate, 702ilvA (VKPM B-8012), which is an ilvA-deficient derivative of the 702 strain, and an *E. coli* strain having an enhanced activity of a protein encoded by the b2682 gene, b2683 gene, b1242 gene, or b3434 gene (JP 2002-300874 A).

Examples of L-leucine-producing bacteria include *Escherichia coli* H-9068 (ATCC 21530), H-9070 (FERM BP-4704), and H-9072 (FERM BP-4706) which exhibits resistance to 4-azaleucine or 5,5,5-trifluoroleucine (U.S. Pat. No. 5,744,331), *Escherichia coli* containing isopropylmalate synthase not subject to feedback inhibition by L-leucine (EP 1067191 B), *Escherichia coli* AJ11478 which is resistant to β-2-thienylalanine and β-hydroxyleucine (U.S. Pat. No. 5,763,231), and *Escherichia coli* 57 (VKPM B-7386, RU 2140450).

Examples of L-cysteine-producing bacteria include *Escherichia coli* JM15 transformed with a cysE gene allele encoding serine acetyltransferase not subject to feedback inhibition (U.S. Pat. No. 6,218,168), *Escherichia coli* W3110 in which the gene encoding the protein responsible for excretion of cytotoxic substances is overexpressed (U.S. Pat. No. 5,972,663), *Escherichia coli* having decreased cysteine desulfhydrase activity (JP 11-155571 A), and *Escherichia coli* W3110 having an amplified transcriptional activator of the cysteine regulon encoded by the cysB gene (WO 01/27307).

Examples of L-isoleucine-producing bacteria include a mutant strain of *Escherichia* that is resistant to 6-dimethylaminopurine (JP 05-304969 A), a mutant strain that is resistant to L-isoleucine hydroxamate, thiaisoleucine, DL-ethionine, or arginine hydroxamate (JP 05-130882 A), and recombinant strains having amplified threonine deaminase gene and acetohydroxylate synthase gene (JP 02-458 A, JP 02-42988 A, and JP 08-47397 A).

An L-valine-producing ability may be imparted by increasing the activities of L-valine synthetic enzymes encoded by the ilvGMEDA operon, in particular, acetohydroxylate synthase encoded by the ilvG gene (JP 02-748418 B). Such an L-valine synthetic enzyme may not be subject to feedback inhibition by L-valine. An L-valine-producing ability may be imparted by decreasing the expression of the acetolactate synthase III gene (ilvIH gene).

Moreover, L-valine-producing ability may be imparted by imparting amino acid analogue-resistance to a bacterium. Examples of such bacteria include mutant strains which are auxotrophic to L-isoleucine or L-methionine and resistant to D-ribose, purine nucleoside, or pyrimidine ribonucleoside (FERM P-1841 and P-5556; JP 53-025034 A), and a mutant strain that is resistant to polyketide (FERM P-9325; JP 1934507 B).

Examples of L-alanine-producing bacteria include a coryneform bacterium in which H$^+$-ATPase activity is deficient (Appl Microbiol Biotechnol. 2001 November; 57(4): 534-40) and a coryneform bacterium in which aspartate decarboxylase gene is amplified (JP 07-163383 A).

Examples of L-arginine-producing bacteria include *Escherichia coli* mutant strains which are resistant to α-methylmethionine, p-fluorophenylalanine, D-arginine, arginine hydroxamate, S-(2-aminoethyl)-cysteine, α-methylserine, β-2-thienylalanine, or sulfaguanidine (JP 56-106598 A). A preferable L-arginine-producing bacterium is *Escherichia coli* 237, which is a mutant strain which is resistant to feedback inhibition by L-arginine and has enhanced N-acetylglutamate synthase activity (RU 2000117677). The strain was deposited at the Russian National Collection of Industrial Microorganisms (VKPM), GNII Genetika on Apr. 10, 2000 and given an accession number of VKPM B-7925, and the deposit was then converted to an international deposit under the provisions of Budapest Treaty on May 18, 2001. *Escherichia coli* 382, which is a derivative of the 237 strain and has improved ability to assimilate acetic acid (JP 2002-017342 A), may be used as an L-arginine-producing bacterium. *Escherichia coli* 382 strain was deposited at the Russian National Collection of Industrial Microorganisms (VKPM) on Apr. 10, 2000 and given an accession number of VKPM B-7926.

Examples of L-arginine-producing bacteria include bacteria modified to have improved expression of a gene encoding an enzyme involved in L-arginine biosynthesis. L-arginine biosynthetic enzymes include N-acetylglutamate synthase (argA), N-acetylglutamyl-phosphate reductase (argC), ornithine acetyltransferase (argJ), N-acetylglutamate kinase (argB), acetylornithine transaminase (argD), acetylornithine deacetylase (argE), ornithine carbamoyl transferase (argF), argininosuccinate synthase (argG), argininosuccinate lyase (argH), and carbamoylphosphate synthase (carAB). The terms in parentheses following the enzyme names refer to names of the genes encoding these enzymes. For N-acetylglutamate synthase (argA), it is more preferable to use a mutant enzyme wherein the wild-type amino acid sequence at positions 15 to 19 is replaced and as a result, the feedback inhibition by L-arginine is reduced or eliminated (EP 1170361 A).

The biosynthetic pathways of L-citrulline and L-ornithine are the same as that of L-arginine, and the ability to produce L-citrulline and L-ornithine can be imparted by increasing the enzymatic activities of N-acetylglutamate synthase (argA), N-acetylglutamylphosphate reductase (argC), ornithine acetyltransferase (argJ), N-acetylglutamate kinase (argB), acetylornithine transaminase (argD), and acetylornithine deacetylase (argE).

Examples of L-lysine-producing bacteria include an L-lysine analogue-resistant strain and a metabolic regulation mutant strain. Specific examples thereof include *Escherichia coli* AJ11442 (FERM BP-1543, NRRL B-12185; JP 56-18596 A and U.S. Pat. No. 4,346,170) and *Escherichia coli* VL611 (JP 2000-189180 A). Moreover, WC196 (WO 96/17930) may be used as an L-lysine producing strain of *Escherichia coli*. The WC196 strain is obtained by imparting AEC (S-(2-aminoethyl)-cysteine) resistance to the W3110 strain, which is derived from *Escherichia coli* K-12 strain. The WC196 strain was named *Escherichia coli* AJ13069 strain and deposited in the National Institute of Bioscience and Human-Technology, Agency of Industrial Science and Technology (currently, International Patent Organism Depositary, National Institute of Advanced Industrial Science and Technology, Central 6, 1-1-1 Higashi, Tsukuba, Ibaraki 305-8566, Japan) on Dec. 6, 1994 and given an accession number of FERM P-14690, and the deposit was then converted to an international deposit under the provisions of Budapest Treaty on Sep. 29, 1995 and given an accession number of FERM BP-5252.

A bacterium having an L-lysine-producing ability may also be obtained by increasing the activity of an enzyme involved in the L-lysine biosynthetic system. The enzymatic activity can be increased by increasing the copy number of the gene encoding the enzyme in the cells, or by modifying an expression regulatory sequence of the gene.

Genes encoding an L-lysine biosynthetic enzyme include a gene encoding an enzyme involved in the diaminopimelic acid pathway such as dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (WO 96/40934), phosphoenolpyruvate carboxylase gene (ppc) (JP 60-87788 A), aspartate aminotransferase gene (aspC) (JP 6-102028 B), diaminopimelate epimerase gene (dapF) (JP 2003-135066 A), and aspartate semialdehyde dehydrogenase gene (asd) (WO 00/61723), and a gene encoding an enzyme involved in an aminoadipic acid pathway such as the homoaconitate hydratase gene (JP 2000-157276 A).

Meanwhile, the aspartokinase III gene (lysC) is preferably modified so that feedback inhibition by L-lysine is reduced or eliminated. Such a lysC gene can be obtained by the method described in U.S. Pat. No. 5,932,453.

Furthermore, a bacterium having an L-lysine-producing ability may be obtained by decreasing or eliminating an activity of an enzyme that catalyzes a reaction which results in generation of a compound other than L-lysine or an activity of an enzyme that negatively functions in L-lysine production. Examples of such enzymes include homoserine dehydrogenase, lysine decarboxylase (cadA, ldcC), and malic enzyme, and strains in which activities of such enzymes are decreased or deficient are described in WO 95/23864, WO 96/17930, WO 2005/010175.

L-tryptophan-producing bacteria are preferably those having enhanced activities of one or more of anthranilate synthase, phosphoglycerate dehydrogenase, and tryptophan synthase. Anthranilate synthase and phosphoglycerate dehydrogenase are regulated by feedback inhibition by L-tryptophan and L-serine, respectively. Therefore, these enzymes may be modified so that feedback inhibition is alleviated. Specifically, anthranilate synthase gene (trpE) and/or phosphoglycerate dehydrogenase gene (serA) is mutated so that feedback inhibition is alleviated, and the mutant genes are introduced into a bacterium, for example, a bacterium belonging to the Enterobacteriaceae family. Specific examples include a recombinant strain obtained by transforming *Escherichia coli* SV164 which harbors a feedback-resistant anthranilate synthase with pGH5 (WO 94/08031), which contains a mutant serA gene encoding a feedback-resistant phosphoglycerate dehydrogenase.

The L-tryptophan-producing ability may be imparted by introducing a recombinant DNA containing the tryptophan operon. Specific examples thereof include *Escherichia coli* transformed with a tryptophan operon comprising the gene encoding a feedback-resistant anthranilate synthase (JP 57-71397 A, JP 62-244382 A, and U.S. Pat. No. 4,371,614). The L-tryptophan-producing ability may also be imparted and/or enhanced by enhancing the expression of the gene encoding the tryptophan operon, in particular, tryptophan synthase (trpBA). Tryptophan synthase has α and β subunits, which are encoded by trpA and trpB, respectively.

The L-tryptophan-producing ability may also be imparted by disrupting the trpR gene, which represses the tryptophan operon, or by introducing a mutation into the trpR gene (U.S. Pat. No. 4,371,614 and WO 2005/056776).

Preferable examples of L-tryptophan-producing bacteria include a bacterium in which malate synthase, isocitrate lyase, isocitrate dehydrogenase kinase/phosphatase operon (ace operon) are constitutively expressed or wherein the expression of the operon is enhanced. It is preferable to modify the promoter of the ace operon to avoid suppression by the repressor iclR, or the iclR gene may be disrupted.

The bacterium in which the expression of the ace operon has been enhanced may be obtained by ligating a DNA containing the ace operon to a strong promoter and introducing the construct into a bacterium using a plasmid, homologous recombination or transposon to increase the copy number of the DNA.

Furthermore, examples of a bacterium having L-tryptophan-producing ability include *Escherichia coli* AGX17 (pGX44) [NRRL B-122363] that exhibits L-phenylalanine- and L-tyrosine-auxotrophy and AGX6(pGX50)aroP [NRRL B-12264] that contains pGX50, which contains a tryptophan operon (U.S. Pat. No. 4,371,614).

L-tryptophan, L-phenylalanine, and L-tyrosine are aromatic amino acids and are produced by a common biosynthesis pathway. Examples of genes encoding aromatic amino acid biosynthetic enzymes include deoxyarabino-heptulosonate phosphate synthase (aroG), 3-dehydroxynate synthase (aroB), shikimate dehydratase, shikimate kinase (aroL), 5-enolpyruvylshikimate 3-phosphate synthase (aroA), and chorismate synthase (aroC) (EP 763127 A). Therefore, an aromatic amino acid-producing ability may be enhanced by increasing the copy number of these genes on a plasmid or on a chromosome. Furthermore, it is known that these genes are regulated by a tyrosine repressor (tyrR), and the activity of the aromatic amino acid biosynthetic enzymes may be increased by disrupting the tyrR gene (EP 763127 B).

Examples of bacteria with L-phenylalanine-producing ability include AJ12739 in which the tyrA gene and tyrR gene are disrupted (tyrA:Tn10, tyrR) (VKPM B-8197), and a strain in which phenylalanine export genes such as yddG and yedA are amplified (WO 03/044192).

Examples of bacteria with an L-threonine-producing ability include Enterobacteriaceae having enhanced activity of an L-threonine-biosynthetic enzyme. Examples of a gene encoding the L-threonine-biosynthetic enzyme include aspartokinase III gene (lysC), aspartate semialdehyde dehydrogenase gene (asd), aspartokinase I gene (thrA), homoserine kinase gene (thrB), and threonine synthase gene (thrC). The terms in parentheses following the enzyme names refer to the names of the genes encoding these enzymes. Two or more of these genes may be introduced into the host bacterium. Such an L-threonine biosynthetic gene may be introduced into an *Escherichia* bacterium in which degradation of L-threonine has been suppressed. Examples of an *Escherichia* bacterium in which degradation of L-threonine has been suppressed include the TDH6 strain in which an activity of threonine dehydrogenase is deficient (JP 2001-346578 A).

The activity of the L-threonine biosynthetic enzyme is suppressed by L-threonine. Therefore, to construct an L-threonine-producing bacterium, an L-threonine biosynthetic gene is preferably modified so that the enzyme is not regulated by feedback inhibition by L-threonine. Meanwhile, the above-described thrA, thrB, and thrC genes constitute a threonine operon which forms an attenuator structure, and the expression of the threonine operon is repressed by isoleucine or threonine in the culture medium, i.e. repressed by attenuation. The modification can be achieved by removing the leader sequence and/or the attenuator in the attenuation region (Lynn, S. P., Burton, W. S., Donohue, T. J., Gould, R. M., Gumport, R. I., and Gardner, J. F. J. Mol. Biol. 194: 59-69 (1987); WO 02/26993; and WO 2005/049808).

A specific promoter is located upstream of the threonine operon and the promoter may be replaced by a heterologous promoter (WO 98/04715), or the threonine operon may be regulated by a repressor or promoter of lambda phage (EP 0593792 B). To modify an *Escherichia* bacterium so that the threonine operon is not regulated by feedback inhibition with L-threonine, a bacterial strain which is resistant to α-amino-β-hydroxyvaleric acid (AHV) may be selected.

Preferably, the modified threonine operon that is not regulated by feedback inhibition with L-threonine is ligated to a strong promoter, and introduced into a host bacterium. Increasing the copy number can be achieved by amplifying the threonine operon using a plasmid or by transferring the threonine operon to a chromosome using a transposon, Mu-phage, or the like.

It is preferable to enhance the expression of genes involved in the glycolytic pathway, TCA cycle, and respiratory chain, genes that regulate expression of these genes, and sugar uptake genes, in addition to the genes encoding the L-threonine biosynthetic enzymes. Examples of such genes effective for L-threonine production include the transhydronase gene (pntAB) (EP 733712 B), phosphoenolpyruvate carboxylase gene (pepC) (WO 95/06114), phosphoenolpyruvate synthase gene (pps) (EP 877090), and pyruvate carboxylase gene derived from a coryneform bacterium or a *Bacillus* bacterium (WO 99/18228 and EP 1092776).

It is preferable to enhance the expression of genes which impart L-threonine and L-homoserine resistance, or impart L-threonine and/or L-homoserine resistance to a host. Examples of such genes include the rhtA gene (Res. Microbiol. 154: 123-135 (2003)), rhtB gene (EP 0994190 A), rhtC gene (EP 1013765 A), yfiK gene, and yeaS gene (EP 1016710 A). L-threonine resistance may also be imparted to a host according to the methods described in EP 0994190 A and WO 90/04636.

Examples of a bacterium having an L-threonine-producing ability include *Escherichia coli* VKPM B-3996 strain (U.S. Pat. No. 5,175,107). The VKPM B-3996 strain was deposited at the Russian National Collection of Industrial Microorganisms (VKPM), GNII Genetika on Apr. 7, 1987 and given an accession number of VKPM B-3996. The VKPM B-3996 strain contains the plasmid pVIC40 (WO 90/04636) which is obtained by inserting a threonine biosynthetic gene (threonine operon: thrABC) into pAYC32, which is a plasmid vector with a wide host-range and includes a streptomycin resistant marker (Chistorerdov, A. Y., and Tsygankov, Y. D. Plasmid, 16, 161-167 (1986)). pVIC40 includes a mutant thrA gene which encodes aspartokinase L-homoserine dehydrogenase I which is not subject to feedback inhibition by L-threonine.

Another example of a bacterium having an L-threonine-producing ability is the *Escherichia coli* B-5318 strain (EP 0593792 B). The B-5318 strain was deposited at the Russian National Collection of Industrial Microorganisms (VKPM), GNII Genetika on May 3, 1990 and given an accession number of VKPM B-5318. The B-5318 strain is prototrophic with regard to isoleucine, and harbors a plasmid having a threonine operon with an attenuator region located downstream of the temperature-sensitive C1 repressor, PR promoter and N-terminal site of the Cro protein of lambda phage, so that expression of the threonine biosynthetic genes is regulated by the repressor and promoter of lambda phage.

<1-2> Enhancement of Phosphotransacetylase Activity

The bacterium of the present invention can be obtained by modifying the above-described bacterium having an L-amino acid-producing ability so that phosphotransacetylase activity is enhanced. However, L-amino acid-producing ability may be imparted after the bacterium is modified so that the phosphotransacetylase activity is enhanced.

The phrase "modified so that phosphotransacetylase activity is enhanced" includes when the number of phosphotransacetylase molecules per cell increases and when the phosphotransacetylase activity per molecule increases as compared to a wild-type strain or unmodified strain. In the case of a coryneform bacterium, examples of the wild-type strain to be used as a control include *Corynebacterium glutamicum* (*Brevibacterium lactofermentum*) ATCC13869 and ATCC13032. Examples of a wild-type *Escherichia coli* include *Escherichia coli* W3110 (ATCC 27325) and *Escherichia coli* MG1655 (ATCC 47076), which are derived from the prototype wild-type K-12 strain. Examples of a wild-type *Pantoea ananatis* include *Pantoea ananatis* AJ13355 (FERM BP-6614) and AJ13356 (FERM BP-6615).

In the present invention, phosphotransacetylase (phosphoacetyltransferase) catalyzes the reaction to generate acetyl-CoA and phosphate from acetyl phosphate and CoA or the reverse reaction thereof, and is also referred to as phosphate acetyltransferase or phoshoacetylase (EC 2.3.1.8).

In the present invention, enhanced phosphotransacetylase activity can be determined by the method described in Reinscheid D. J. et al. (Microbiology. 145: 503-513 (1999)).

Enhanced phosphotransacetylase activity may also be confirmed by comparing the mRNA level of the gene encoding phosphotransacetylase to that of a wild-type or unmodified strain. Methods of detecting the expression level of a gene include Northern hybridization and RT-PCR (Molecular cloning (Cold spring Harbor Laboratory Press, Cold spring Harbor (USA), 2001). The phosphotransacetylase activity or gene expression level in the bacterium of the present invention may be at any level as long as it is increased as compared to a wild-type or unmodified strain, and for example, the activity or gene expression preferably increases not less than 1.5-fold, more preferably not less than 2-fold, furthermore preferably not less than 3-fold as compared to a wild-type or unmodified strain.

The gene encoding phosphotransacetylase (pta gene) of a coryneform bacterium includes the nucleotide sequence of NCgl2657 (ATCC13032) registered in Genbank (a complementary strand of 2936506..2937891 of accession NC_003450.3). SEQ ID Nos: 40 and 41 show the nucleotide sequence of the gene and the amino acid sequence encoded by the gene, respectively. Furthermore, nucleotide numbers 1214-2641 of SEQ ID NO: 34 and SEQ ID NO: 35 show the nucleotide sequence of the pta gene of *C. glutamicum* ATCC13869 and the amino acid sequence encoded by the gene, respectively.

Furthermore, the gene of the present invention may be a homologue of the pta gene which is derived from another bacterium as long as it encodes a protein having the phosphotransacetylase activity. Such a homologue can be searched by BLAST (http://blast.genome.jp/) or the like with reference to the nucleotide sequence of nucleotides 1214 to 2641 of SEQ ID NO: 34 or the nucleotide sequence of SEQ ID NO: 40.

The nucleotide sequence of the pta gene of the present invention has been identified. Therefore, the region containing the pta gene, or the pta gene and its expression regulatory sequences, can be obtained by PCR (PCR: polymerase chain reaction; White, T. J. et al., Trends Genet. 5, 185 (1989)) using primers prepared based on the known nucleotide sequence, for example, using the primers of SEQ ID Nos: 9 and 10, and using the chromosomal DNA of a coryneform bacterium as a template. A homologue of the pta gene derived from another bacterium can be obtained in the same way.

There may be differences between the nucleotide sequences of pta genes depending on species or strains of the bacteria used to isolate the pta gene. Therefore, the pta gene is not limited to the nucleotides 1214 to 2641 of SEQ ID NO: 34 or the nucleotide sequence of SEQ ID NO: 40, but may be a mutant or an artificially modified gene which encodes a protein having the amino acid sequence of SEQ ID NO: 35 or 41 and which may include substitutions, deletions, insertions, or additions of one or several amino acids at one or several positions as long as it encodes a protein having the phosphotransacetylase activity. Although, depending on the positions in the ternary structure of the protein or types of amino acids, the term "one or several" used herein specifically means 1 to 20, preferably 1 to 10, more preferably 1 to 5. Meanwhile, such substitutions, deletions, insertions, additions, or inversions include naturally-occurring mutations (mutants or variants) due to differences in individuals or species of the bacteria harboring the pta gene.

The above-mentioned substitution is preferably a conservative substitution that does not cause a functional change. The conservative substitutions include a substitution between aromatic amino acids such as substitution among Phe, Trp and Tyr; a substitution between hydrophobic amino acids such as substitution among Leu, Ile and Val; a substitution between polar amino acids such as substitution between Gln and Asn; a substitution between basic amino acids such as substitution among Lys, Arg and His; a substitution between acidic amino acids such as substitution between asp and Glu; a substitution between amino acids having a hydroxyl group such as substitution between Ser and Thr. Specific examples of the conservative substitution include: substitution of Ser or Thr for Ala; substitution of Gln, His, or Lys for Arg; substitution of Glu, Gln, Lys, His or Asp for Asn; substitution of Asn, Glu, or Gln for Asp; substitution of Ser or Ala for Cys; substitution of Asn, Glu, Lys, His, Asp, or Arg for Gln; substitution of Gly, Asn, Gln, Lys, or Asp for Glu; substitution of Pro for Gly; substitution of Asn, Lys, Gln, Arg, or Tyr for His; substitution of Leu, Met, Val, or Phe for Ile; substitution of Ile, Met, Val, or Phe for Leu; substitution of Asn, Glu, Gln, His, or Arg for Lys; substitution of Ile, Leu, Val, or Phe for Met; substitution of Trp, Tyr, Met, Ile, or Leu for Phe; substitution of Thr or Ala for Ser; substitution of Ser or Ala for Thr; substitution of Phe or Tyr for Trp; substitution of His, Phe, or Trp for Tyr; and substitution of Met, Ile, or Leu for Val.

Furthermore, the pta gene may be a gene that has a nucleotide sequence having at least 80%, preferably at least 90%, more preferably 95%, particularly preferably at least 97% homology to the entire amino acid sequence of SEQ ID NO: 35 or 41, and encodes a protein having phosphotransacetylase activity. Also, the pta gene may be modified to have a codon that is easily used by the chosen host bacterium because the degeneracy levels of genes are different depending on the host bacterium.

The pta gene may have an elongated or shortened sequence at the N-terminal side and/or C-terminal side as long as it encodes a protein having phosphotransacetylase activity. The length of the amino acid sequence which is elongated or shortened is 50 or less, preferably 20 or less, more preferably 10 or less, particularly preferably 5 or less. More specifically, the pta gene may have an amino acid sequence of SEQ ID NO: 35 or 41 in which an additional 50 to 5 amino acids are present at the N-terminal side and/or at the C-terminal side.

A homologue of the pta gene can be obtained by modifying the nucleotide sequence of nucleotides 1214 to 2641 of SEQ ID NO: 34 or the nucleotide sequence of SEQ ID NO: 40 so that specific amino acid residues in the protein encoded by the gene are substituted, deleted, inserted, or added, for example, by site-specific mutagenesis. Furthermore, a homologue gene may also be obtained by a known mutation treatment as described below. A homologue gene may be obtained by treating the above-described nucleotide sequence in vitro with hydroxylamine or the like, treating a bacterium harboring the gene, for example, a coryneform bacterium with ultraviolet rays or with a mutagen such as N-methyl-N'-nitro-N-nitrosoguanidine (NTG) or ethylmethanesulfonate (EMS), or by artificially introducing a mutation into the pta gene by gene recombination such as error-prone PCR, DNA shuffling, and StEP-PCR (Firth A E, Patrick W M; Bioinformatics. 2005 Jun. 2; Statistics of protein library construction). Determination of the enzymatic activity by the above-described method can confirm whether such a pta gene homolog encodes a protein having the phosphotransacetylase activity.

Examples of the pta gene include a DNA that hybridizes with a sequence complementary to nucleotides 1214 to 2641 of SEQ ID NO: 34 or the nucleotide sequence of SEQ ID NO: 40, or with a probe that can be prepared from the sequences under stringent conditions and encodes a protein having the phosphotransacetylase activity. The term "stringent conditions" used herein includes conditions under which a so-called specific hybrid is formed and non-specific hybrid is not formed. Examples thereof include conditions under which DNAs having high homology of at least 80%, preferably at least 90%, more preferably at least 95%, further more preferably at least 97% hybridize with each other and DNAs having homology of less than 80% do not hybridize with each other; and specifically includes conditions of washing in general Southern hybridization, i.e., conditions including washing at a salt concentration of 1×SSC, 0.1% SDS, preferably 0.1×SSC, 0.1% SDS at 60° C., preferably 68° C., once, preferably twice or three times.

As a probe, a partial sequence of nucleotides 1214 to 2641 of SEQ ID NO: 34 or a partial sequence of the nucleotide sequence of SEQ ID NO: 40 may be used. Such a probe can be prepared by PCR using oligonucleotides prepared based on the nucleotide sequences as primers and a DNA fragment having the nucleotide sequence of nucleotides 1214 to 2641 of SEQ ID NO: 34 or the nucleotide sequence of SEQ ID NO: 40 as a template. For example, when using a DNA fragment having a length of about 300 bp, exemplary washing conditions include hybridization in 2×SSC, 0.1% SDS at 50° C.

The expression of the pta gene can be enhanced by increasing the copy number of the pta gene. For example, the expression can be enhanced by preparing a recombinant DNA by ligating a fragment containing the pta gene into a vector that functions in the host bacterium, preferably a multi-copy vector; and then transforming the above-described bacterium having an L-amino acid-producing ability with the recombinant DNA. Alternatively, the expression may be enhanced by introducing the above-described recombinant DNA into a wild-type bacterium to prepare a transformant, and then imparting an L-amino acid-producing ability to the transformant. Meanwhile, the copy number may be increased by transferring one or more copies of the pta gene on the chromosome. Integration of the pta gene into the chromosome can be confirmed by Southern hybridization using a part of the pta gene as a probe.

Expression of the pta gene can also be enhanced by modifying an expression regulatory region of the pta gene. For example, it can be achieved by replacing a promoter sequence of the pta gene with a more potent promoter, or modifying a promoter sequence to be close to a consensus sequence (WO 00/18935).

Hereinafter, methods of constructing a coryneform bacterium modified so that the phosphotransacetylase activity is increased will be shown. These methods can be performed in accordance with the manuals of Molecular Cloning (Cold Spring Harbor Laboratory Press, Cold Spring Harbor (USA), 2001) and the like. Bacteria other than coryneform bacteria may also be modified so that the phosphotransacetylase activity is increased by the same method.

The expression level of the pta gene can be enhanced by increasing the copy number of the pta gene, and the copy number may be increased by amplifying the pta gene using a plasmid as described below. First, the pta gene is cloned from the chromosome of a coryneform bacterium. The chromosomal DNA may be prepared from a bacterium that serves as a DNA donor by, for example, the method of Saito and Miura (Biochem. Biophys. Acta, 72, 619 (1963), Experiment Manual for Biotechnology, edited by The Society for Biotechnology, Japan, p 97-98, Baifukan Co., Ltd., 1992). Oligonucleotides for PCR are synthesized based on the above-described known sequence information, and the pta gene can be amplified by using the synthetic oligonucleotides of SEQ ID NOS: 9 and 10, for example.

A gene fragment containing the amplified pta gene is ligated to a vector which is autonomously replicable in *Escherichia coli* and/or coryneform bacterium, and the recombinant DNA is introduced into *Escherichia coli*. Examples of a vector which is autonomously replicable in *Escherichia coli* include pUC19, pUC18, pHSG299, pHSG399, pHSG398, RSF1010, pBR322, pACYC184, and pMW219.

The above-mentioned DNA is introduced into a vector capable of functioning in coryneform bacteria. An example of such a vector includes a plasmid capable of autonomously replicating in coryneform bacteria. Specific examples thereof include pCRY30 described in JP 3-210184 A; pCRY21, pCRY2KE, pCRY2KX, pCRY31, pCRY3KE, and pCRY3KX described in JP 2-72876 A and U.S. Pat. No. 5,185,262; pCRY2 and pCRY3 described in JP 1-191686 A; pAM330 described in JP 58-67679 A; pHM1519 described in JP 58-77895 A; pAJ655, pAJ611, and pAJ1844 described in JP 58-192900 A; pCG1 described in JP 57-134500 A; pCG2 described in JP 58-35197 A; pCG4 and pCG11 described in JP 57-183799 A; and pVK7 described in JP 10-215883 A.

Furthermore, if a DNA fragment able to autonomously replicate in a coryneform bacterium is excised from one of these plasmids and inserted into the above-described vector for *Escherichia coli*, this vector can be used as a so-called shuttle vector, and it will be autonomously replicable in both *Escherichia coli* and coryneform bacteria.

These vectors can be obtained from the deposited bacteria shown in the above-described patent documents as follows. Cells collected at the logarithmic growth phase are lysed with lysozyme and SDS, and centrifuged at 30,000×g, and then polyethylene glycol is added to the supernatant, followed by separation and purification by cesium chloride-ethidium bromide equilibrium gradient centrifugation.

To prepare a recombinant DNA by ligating the pta gene with a vector that functions in coryneform bacteria, the vector is digested with a restriction enzyme suitable for excising a fragment containing the pta gene. The restriction site can be introduced in advance into a synthetic oligonucleotide for amplifying the pta gene. The ligation is generally performed using a ligase such as T4DNA ligase.

The recombinant plasmid prepared as described above may be introduced into a coryneform bacterium by any transformation method reported so far. Examples thereof include increasing the permeability of a DNA by treating recipient cells with calcium chloride, which has been reported for *Escherichia coli* K-12 (Mandel, M. and Higa, A., J. Mol. Biol., 53, 159 (1970), and introducing a DNA into competent cells prepared from cells at the proliferation stage, which has been reported for *Bacillus subtilis* (Duncan, C. H., Wilson, G. A and Young, F. E, Gene, 1, 153 (1977)). Alternatively, preparing protoplast-like cells or spheroplast-like cells of a DNA-recipient bacterium, which can easily incorporate a recombinant DNA, and introducing a recombinant DNA into these cells may also be used (Chang, S, and Choen, S. N., Mol. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75 1929 (1978)). A coryneform bacterium can also be transformed by the electric pulse method (JP 02-207791 A) or the conjugation transfer method (Biotechnology (NY). 1991 January; 9(1): 84-7).

The copy number of the pta gene can be increased by introducing multiple copies of the pta gene into the chromosomal DNA of a coryneform bacterium. In order to introduce multiple copies of the pta gene into the chromosomal DNA of a coryneform bacterium, homologous recombination is performed using a sequence which is present on a chromosomal DNA in multiple copies. Repetitive DNA or an inverted repeat existing at the end of a transposable element can be used as a sequence which is present on a chromosomal DNA in multiple copies. Alternatively, as disclosed in JP 02-109985 A, multiple copies of the pta gene may be introduced by inserting the gene into a transposon, to thereby transfer multiple copies of the gene into a chromosomal DNA (JP 02-109985 A, JP 07-107976 A, and Mol. Gen. Genet., 245, 397-405 (1994), Plasmid. 2000 November; 44(3):285-91).

Furthermore, the pta gene may be amplified on the chromosome by inserting the pta gene into a plasmid having a replication origin which cannot replicate in the host or a plasmid having a replication origin which cannot replicate in the host and is capable of conjugation transfer. Examples of such a plasmids include pSUP301 (Simo et al., Bio/Technology 1, 784-791 (1983)), pK18mob, or pK19mob (Schaefer et al., Gene 145, 69-73 (1994)), pGEM-T (Promega corporation, Madison, Wis., USA), pCR2.1-TOPO (Shuman (1994). Journal of Biological Chemistry 269: 32678-84; U.S. Pat. No. 5,487,993), pCR(R)Blunt (Invitrogen, Groningen, Netherlands; Bernard et al., Journal of Molecular Biology, 234: 534-541 (1993)), pEM1 (Schrumpf et al., 1991, Journal of Bacteriology 173: 4510-4516), and pBGS8 (spratt et al., 1986, Gene, 41: 337-342). A plasmid vector containing the pta gene is transferred to a coryneform bacterium by conjugation or transformation. A conjugation method is described, for example, by Schaefer et al. (Applied and Environmental Microbiology 60, 756-759 (1994)). Methods of the transformation are described, for example, by Theirbach et al. (Applied Microbiology and Biotechnology 29, 356-362 (1988)), Dunican and Shivinan (Bio/Technology 7, 1067-1070 (1989)), and Tauch et al. (FEMS Microbiological Letters 123, 343-347 (1994)).

Expression of the pta gene may also be increased by replacing an expression regulatory sequence such as the promoter of the pta gene on the chromosomal DNA or on a plasmid with a more potent promoter, modifying a factor involved in the regulation of expression of the pta gene, for example, an operator or a repressor, or ligating a more potent terminator (Hamilton et al.; Journal of Bacteriology 171: 4617-4622). Examples of known potent promoters include the lac promoter, trp promoter, trc promoter, and PS2 promoter. Methods of evaluating promoter strength and examples of potent promoters are described by Goldstein et al. (Prokaryotic promoters in biotechnology. Biotechnol. Annu. Rev., 1995, 1. 105-128). As disclosed in WO 00/18935, a promoter may be made stronger by introducing a substitution of several nucleotides into the promoter region of the target gene so that the promoter becomes close to a consensus sequence. For example, the −35 region may be changed into TTGACA or TTGCCA, while the −10 region may be changed into TATAAT or TATAAC. In addition, it is known that translation efficiency of mRNA is significantly affected by substituting several nucleotides in a spacer sequence between the ribosome binding site (RBS) and the translation initiation codon, in particular, the sequence immediately upstream of the translation initiation codon, and in this way, the spacer sequence may be modified.

An example of an upstream region of the pta gene includes nucleotides 1 to 1213 of SEQ ID NO: 34. An expression regulatory sequence such as a promoter of the pta gene can be determined using a promoter search vector or gene-finding software such as GENETYX. The above-described promoter substitution or modification enhances the expression of the pta gene. The expression regulatory sequence may also be substituted by using a temperature-sensitive plasmid. The modification of an expression regulatory sequence may be combined with increasing the copy number of the pta gene.

Furthermore, the expression may also be increased by extending the retention time of the mRNA or by preventing degradation of the PTA protein in the cell.

Also, there is a binding site for the RamB protein which negatively regulates the expression of the pta gene. This binding site is located upstream of the pta gene in coryneform bacterium, and thus, the RamB protein-binding site may be modified to increase the pta activity. The RamB protein-binding sites which are located upstream of the pta gene have been reported in J. Bacteriol. 2004 May; 186 (9): 2798-2809, and are predicted to include AAAACTTTGCAAA starting at position −87 and AAAACTTTGCAAA starting at position −203 as counted from the translation initiation codon of the pta gene (the sequences of these RamB protein-binding sites correspond to nucleotides 1000 to 1012 and 1115 to 1127 of SEQ ID NO: 34, respectively). A RamB protein-binding sequence is reported to have a consensus sequence of A(A/G)AACTTTGCAAA and is located upstream of the aceA gene which encodes isocitrate lyase, the aceB gene which encodes malate synthase, and the pta-ack operon, and the expression of these genes is induced in the presence of a high concentration of acetic acid. Therefore, modification of the conserved sequence can prevent the decrease in expression of the pta gene due to binding of RamB, and examples of a modification of the sequence include replacing an AT base pair with a GC base pair and replacing a GC base pair with an AT base pair, and specifically include replacing AAAACTTTGCAAA with aaaacGAGgcGaG or aaaacGAGgcaaa.

Whether the pta gene is modified so that it is negatively regulated by RamB can be confirmed by examining if the pta gene is constitutively expressed in the absence of acetic acid (for example, only glucose is present as a carbon source) (J. Bacteriol. 2004 May; 186 (9): 2798-809).

The phosphotransacetylase activity may also be increased by modifying a regulator protein that regulates the expression of the pta gene. An example of a regulator for the pta gene includes the above-described RamB protein since it negatively controls the expression of the pta gene. The ramB gene of coryneform bacterium has been registered in Genbank. For example, the ramB gene of *glutamicum* ATCC13032 strain is registered under an accession No. NC_006958.1: 390784..392208. SEQ ID NOS: 42 and 43 show the sequence of the ramB gene and the amino acid sequence encoded by the ramB gene, respectively. Meanwhile, SEQ ID NO: 36 and 37 show the ramB gene of *C. glutamicum* ATCC13869 strain and the amino acid sequence encoded by the ramB gene, respectively. The RamB gene may be a DNA which hybridizes with a complementary strand of the nucleotide sequence of SEQ ID NO: 36 or 42 or with a probe prepared therefrom under stringent conditions, and encodes a protein that binds to the RamB-binding sites to represses the expression of the pta gene. Here, the stringent conditions are as mentioned above.

Expression of the ramB gene may be decreased to enhance the expression of the pta gene. For example, a mutation that decreases or eliminates the expression of the ramB gene may be introduced by a gene recombination technique as follows. A partial sequence of the ramB gene is mutated so that the RamB protein is not produced, and a bacterium is transformed with a DNA comprising the mutant ramB gene to cause recombination between the mutant ramB gene and a wild-type ramB gene on the chromosome, resulting in replacement of the wild-type ramB gene on the chromosome with the mutant ramB gene.

The wild-type ramB gene on the chromosome of a host bacterium can be replaced by the mutant ramB gene by the following procedures, for example. First, a plasmid for recombination is prepared by inserting into a plasmid vector a temperature-sensitive replication origin, the mutant ramB gene, a sacB gene encoding a levansucrase, and a marker gene that exhibits resistance to an antibiotics, such as chloramphenicol.

Herein, the sacB gene encodes a levansucrase, and is used for effectively selecting a strain in which a vector portion has been cured from the chromosome (Schafer, A. et al. Gene 145 (1994) 69-73). When a levansucrase is expressed in a bacterium, the bacterium cannot grow because levan generated by assimilation of sucrose lethally effects the bacterium. If a strain in which the sacB gene-carrying vector remains on the chromosome is cultured on a sucrose-containing plate, it cannot grow. Therefore, only a strain in which the vector has been cured from the chromosome can be selected on a sucrose-containing plate.

Examples of the sacB gene and homologues thereof include the following:

*Bacillus subtilis*: sacB GenBank Accession No. X02730 (WO 2005/113745)

*Bacillus amyloliquefaciens*: sacB GenBank Accession No. X52988

*Zymomonas mobilis*: sacB GenBank Accession No. L33402

*Bacillus stearothermophilus*: surB GenBank Accession No. U34874

*Lactobacillus sanfranciscensis*: frfA GenBank Accession No. AJ508391

*Acetobacter xylinus*: lsxA GenBank Accession No. AB034152

*Gluconacetobacter diazotrophicus*: lsdA GenBank Accession No. L41732

The transformant obtained by introducing a plasmid containing the sacB gene and the mutant ramB gene is cultured at an appropriate temperature for the functioning of the temperature-sensitive replication origin (25° C.). This strain is cultured at a high temperature (for example, 34° C.) so that the temperature-sensitive replication origin cannot function, resulting in the curing of the temperature-sensitive plasmid, and then this strain is cultured on a plate containing an antibiotic. Since the temperature-sensitive plasmid cannot replicate at a high temperature, a strain which has been cured of the plasmid cannot grow on a plate containing an antibiotic, but a strain in which recombination occurs between the mutant ramB gene on the plasmid and the wild-type ramB gene on the chromosome can grow, and colonies appear.

In a strain containing the mutant ramB gene integrated into the chromosomal DNA, recombination is caused between the mutant ramB gene and the wild-type ramB gene native to the chromosome, and the fusion genes of the wild-type ramB gene and the mutant ramB gene are inserted into the chromosome so that the other portions of the recombinant DNA (vector segment, temperature sensitive replication origin and antibiotic resistance marker) are present between the fusion genes.

Then, in order to leave only the mutant ramB gene on the chromosome, one copy of the ramB gene is eliminated together with the vector segment (including the temperature-sensitive replication origin and the antibiotics resistance marker) from the chromosomal DNA. In this case, the wild-type ramB gene is left on the chromosomal DNA and the mutant ramB gene is excised from the chromosomal DNA, or to the contrary, the mutant ramB gene is left on the chromosomal DNA and the wild-type ramB gene is excised from the chromosome DNA. In both cases, the excised DNA is maintained in the host bacterium when the host bacterium is cultured at a temperature which allows the temperature-sensitive replication origin to function. Then, the gene on the plasmid is cured from the cells along with the plasmid by culturing the bacterium at a temperature which does not allow the temperature-sensitive replication origin to function. In the case of the sacB gene, strains from which the plasmid is cured can be efficiently obtained by culturing the bacterium in a sucrose-containing medium. Strains in which the wild-type ramB gene is replaced with the mutant ramB gene can be obtained by selecting strains which harbor the mutant ramB gene from the plasmid-cured strains.

The bacterium of the present invention may be modified so that the activity/activities of D-xylose 5-phosphate-phosphoketolase and/or fructose 6-phosphate phosphoketolase is/are increased in addition to enhancing the phosphotransacetylase activity.

At least one of the D-xylose 5-phosphate-phosphoketolase activity and fructose 6-phosphate phosphoketolase activity may be increased. In the present description, D-xylose 5-phosphate-phosphoketolase and fructose 6-phosphate phosphoketolase are sometimes collectively referred to as phosphoketolase.

The D-xylose 5-phosphate-phosphoketolase activity means an activity which results in conversion of xylose-5-phosphate into glycelaldehyde-3-phosphate and acetyl phosphate by consumption of phosphoric acid, with concomitant release of one molecule of $H_2O$. This activity can be determined by the method described by Goldberg, M. et al. (Methods Enzymol., 9, 515-520 (1996) or by the method described by L. Meile (J. Bacteriol. (2001) 183; 2929-2936).

Meanwhile, the fructose 6-phosphate phosphoketolase activity means an activity which results in conversion of fructose 6-phosphate into erythrose-4-phosphate and acetyl phosphate by consuming phosphoric acid, with concomitant release of one molecule of $H_2O$. This activity can be determined by the method described by Racker, E (Methods Enzymol., 5, 276-280 (1962)) or by the method described by L. Meile (J. Bacteriol. (2001) 183; 2929-2936).

The phosphoketolase activity is enhanced preferably not less than 1.5-fold, more preferably not less than 2-fold, particularly preferably not less than 3-fold as compared to an unmodified strain or a wild-type strain.

As is the case when enhancing phosphotransacetylase activity as described above, the phosphoketolase activity can be enhanced by increasing the copy number of the gene encoding phosphoketolase or modifying a promoter of the gene encoding phosphoketolase.

The phosphoketolase gene of the host bacterium may be amplified, and the phosphoketolase activity may be imparted by introducing a heterologous gene if the host bacterium has no phosphoketolase activity.

A gene encoding D-xylose 5-phosphate-phosphoketolase can be obtained by PCR using as a template the chromosomal DNA of a bacterium having an enzyme activity of D-xylose 5-phosphate-phosphoketolase. Examples of such a bacterium include bacteria such as lactic bacteria, methanol-assimilating bacteria, methane-assimilating bacteria, bacteria belonging to the genus *Streptococcus*, *Acetobacter*, *Bifidobacterium*, *Lactobacillus*, *Thiobacillus*, *Methylococcus*, *Butyrivibrio*, or *Fibrobactor*; and yeasts belong to the genus *Candida*, *Rhodotorula*, *Rhodosporidium*, *Pichia*, *Yarrowia*, *Hansenula*, *Kluyveromyces*, *Saccharomyces*, *Trichosporon*, *Wingea*, or the like.

The gene encoding fructose 6-phosphate phosphoketolase can be obtained by PCR using as a template the chromosomal DNA of a bacterium having an enzymatic activity of fructose 6-phosphate phosphoketolase. Examples of such a bacterium include bacteria belonging to the genus *Acetobacter*, *Bifidobacterium*, *Chlorobium*, *Brucella*, *Methylococcus*, or *Gardnerella*; and yeasts belong to the genus *Candida*, *Rhodotorula*, *Saccharomyces*, or the like.

A specific example of the gene encoding D-xylose 5-phosphate phosphoketolase is the xpkA gene derived from *Lactobacillus pentosus* MD363. The nucleotide sequence thereof is registered with an accession number of AJ309011 (Posthuma, C. C. et al, Appl. Environ. Microbiol., 68(2), 831-7 (2002)) (SEQ ID NO: 52) in the EMBL/GenBank database. The xpkA gene may hybridize with a complementary strand of the nucleotide sequence of SEQ ID NO: 52 or with a probe prepared therefrom under stringent conditions, and which encodes a protein that has D-xylose 5-phosphate phosphoketolase activity.

The xpk1 gene derived from *Lactobacillus plantarum* can also be used. The nucleotide sequence thereof is registered with an accession number of NC_004567 Region (complement of 2362936..2365302) (Kleerebezem, M., et al, Proc. Natl. Acad. Sci. U.S.A. 100 (4), 1990-1995 (2003)) (SEQ ID NO: 54) in the EMBL/GenBank database. The xpk1 gene may hybridize with a complementary strand of the nucleotide sequence of SEQ ID NO: 54 or with a probe prepared therefrom under stringent conditions and encodes a protein that has D-xylose 5-phosphate phosphoketolase activity.

In addition, examples of homologs of these genes include a gene of *Lactobacillus plantarum* which is registered as GenBank Accession No. NC_004567 (complement of 3169067-3171478), a gene of *Streptococcus agalactiae* encoding the amino acid sequence of GenBank Accession No. NP_736274, a gene of *Lactococcus lactis* subsp. *Lactis* encoding the amino acid sequence of GenBank Accession No. NP_267658, a gene of *Lactobacillus johnsonii* which is registered as GenBank Accession No. NC_005362 (696462..698867), and a gene of *Lactobacillus acidophilus* encoding the amino acid sequence of GenBank Accession No. YP_193510.

Other examples of fructose 6-phosphate phosphoketolase gene and/or D-xylose 5-phosphate phosphoketolase gene are disclosed in WO2006/016705.

A gene encoding a protein having the activities of both D-xylose 5-phosphate phosphoketolase and fructose 6-phosphate phosphoketolase can also be used. Examples of such a gene include the xfp gene of *Bifidobacterium animalis*. The nucleotide sequence thereof is registered as accession number of AJ293946 (Meile, L. et al, J. Bacteriol., 183(9), 2929-36 (2001)) (SEQ ID NO: 56) in the EMBL/GenBank database. The xfp gene may hybridize with a complementary strand of the nucleotide sequence of SEQ ID NO: 56 or with a probe prepared therefrom under stringent conditions, and which encodes a protein that has D-xylose 5-phosphate phosphoketolase activity and fructose 6-phosphate phosphoketolase activity.

In addition, examples of a homolog of the xfp gene include a gene isolated from *Bifidobacterium longum* which encodes the amino acid sequence of GenBank Accession No. NP_696135, a gene isolated from *Chlorobium tepidum* which encodes the amino acid sequence of GenBank Accession No. NP_662409, a gene isolated from *Brucella suis* which encodes the amino acid sequence of GenBank Accession No. NP_699578, and a gene isolated from *Brucella abortus* which encodes the amino acid sequence of GenBank Accession No. YP_223570.

The bacterium of the present invention may be modified so that pyruvate carboxylase activity is increased in addition to enhancing phosphotransacetylase activity, or in addition to enhancing the activities of phosphotransacetylase and D-xylose 5-phosphate-phosphoketolase and/or fructose 6-phosphate phosphoketolase.

Examples of the pyruvate carboxylase gene include the pyc gene derived from coryneform bacterium and the pyc gene derived from *Bacillus* bacterium and specific examples thereof include the pyc gene derived from *C. glutamicum* ATCC13032 strain (GenBank Accession No. NCgl0659: SEQ ID NO: 64) and the pyc gene derived from *B. subtilis* (EP 1092776). The pyruvate carboxylase gene may hybridize with a complementary strand of the nucleotide sequence of SEQ ID NO: 64 or with a probe prepared therefrom under stringent conditions, and which encodes a protein that has pyruvate carboxylase activity.

The bacterium of the present invention may also be modified so that phosphoenolpyruvate carboxylase activity is increased in addition to enhancing the phosphotransacetylase activity or in addition to enhancing the activities of phosphotransacetylase, D-xylose 5-phosphate-phosphoketolase and/or fructose 6-phosphate phosphoketolase. Examples of a phosphoenolpyruvate carboxylase gene include the ppc gene derived from coryneform bacterium and the ppc gene derived from *Escherichia* bacterium and specific examples thereof include the ppc gene from *C. glutamicum* ATCC13032 strain (GenBank Accession No. NCgl1523: SEQ ID NO: 62) and the ppc gene derived from *E. coli* MG1655 strain (GenBank Accession No. NP_418391). The phosphoenolpyruvate carboxylase gene may hybridize with a complementary strand of the nucleotide sequence of SEQ ID NO: 62 or with a probe prepared therefrom under stringent conditions, and which encodes a protein that has phosphoenolpyruvate carboxylase activity. Furthermore, since some kind of phosphoenolpyruvate carboxylase is sensitive to feedback inhibition by aspartic acid, it is preferably modified so it is resistant to the feedback inhibition by aspartic acid (EP0723011).

<2> Method of Producing L-Amino Acid

An L-amino acid can be produced by culturing a bacterium obtained as described above in a medium to produce and accumulate an L-amino acid in the medium or the bacterial cells and collecting the L-amino acid from the medium or from the bacterial cells.

The medium can be a typical medium containing a carbon source, nitrogen source, inorganic salts, and if necessary, organic trace nutrients such as an amino acid or a vitamin. Either a synthetic or a natural medium may be used. The carbon source and nitrogen source may be any substance as long as it can be utilized by the chosen strain.

Sugars such as glucose, glycerol, fructose, sucrose, maltose, mannose, galactose, starch hydrolysate, and molasses may be used as the carbon source, and an organic acid such as acetic acid and citric acid and an alcohol such as ethanol may also be used singly or in combination with another carbon source. As a nitrogen source, an ammonium salt such as ammonia, ammonium sulfate, ammonium carbonate, ammonium chloride, ammonium phosphate, or ammonium acetate, or a nitrate salt may be used. As organic trace nutrients, an amino acid, a vitamin, a fatty acid, and a nucleic acid, as well as peptone, casamino acid, yeast extracts, soybean hydrolysate containing these nutrients may be used, and in the case of using a nutrient-auxotrophic mutant strain that requires an amino acid or the like for growth, the required nutrients are supplemented. A phosphate salt, a magnesium salt, a calcium salt, an iron salt, a manganese salt, or the like may be used as the inorganic salt.

The culture is preferably performed with aeration while adjusting the fermentation temperature to 20 to 45° C. and the pH to 3-9. If the pH is lowered during the culture, the medium is neutralized by adding calcium carbonate or an alkaline such as ammonia gas or the like. The culture is performed under such conditions preferably for about 10 to 120 hours, thereby, a large amount of L-amino acid is able to accumulate in the culture medium.

When producing L-glutamic acid, the culture may be performed using a liquid medium which is adjusted to the appropriate conditions for producing L-glutamic acid, while at the same time precipitating L-glutamic acid into the medium. Examples of such conditions include a pH range of 5.0 to 4.0, preferably of pH 4.5 to 4.0, more preferably of pH 4.3 to 4.0, particularly preferably of pH 4.0 (EP 1078989 A).

The L-amino acid can be collected from the culture medium by known collection methods. For example, the L-amino acid can be collected by removing bacterial cells from the culture medium, followed by concentration and crystallization, ion exchange chromatography, or the like. When culturing under conditions for precipitating L-glutamic acid, L-glutamic acid can be collected by centrifugation, filtration, or the like. In this case, L-glutamic acid which is dissolved in the medium may also be crystallized and then collected.

EXAMPLES

Hereinafter, the present invention will be specifically described by referring to the following non-limiting examples.

Example 1

Construction of the pta Gene-Amplified Strain of ATCC13869

A strain in which the sucA gene is disrupted, and a mutant yggB is introduced, was used as a parental strain for amplifying a pta gene. This strain can be constructed by the following methods.

(1-1) Construction of a sucA-Disrupted Strain

A sucA gene-disrupted strain (ATCC13869ΔsucA) was constructed as follows.

Disruption of the sucA gene encoding the E1o subunit of α-ketoglutarate dehydrogenase was performed using pBS3, which carries the sacB gene which encodes levansucrase, according to the method described in WO 2005/113745 and 2005/113744.

A gene fragment which is derived from the *C. glutamicum* ATCC13869 strain and in which the ORF of the sucA gene was deleted, was obtained by the overlap PCR method using synthetic DNAs designed based on the known nucleotide sequence of the sucA gene (SEQ ID NO: 30) of *C. glutamicum* ATCC13032 (GenBank Database Accession No. NC_003450) as primers. Specifically, PCR was performed by a conventional method using a chromosomal DNA of *C. glutamicum* ATCC13869 strain as a template and using synthetic DNAs of SEQ ID NOS: 1 and 2 as primers, to thereby obtain an amplified product corresponding to the N-terminal region of the sucA gene. To obtain an amplified product corresponding to the C-terminal region of the sucA gene, PCR was performed using the chromosomal DNA of the *C. glutamicum* ATCC13869 strain as a template, and using synthetic DNAs of SEQ ID NOS: 3 and 4 as primers. SEQ ID NOS: 2 and 3 are complementary to each other, and are designed to amplify the sucA gene which has the entire ORF deleted.

Subsequently, to obtain a sucA gene fragment wherein the internal sequence is deleted, the above-described amplified products each corresponding to the N-terminal region and the C-terminal region of the sucA gene were mixed in approximately equal molar amounts, and PCR was performed using the mixture as templates and using synthetic DNAs of SEQ ID NOS: 5 and 6 as primers, to thereby obtain a sucA gene-amplified product into which the deletion mutation was introduced. The PCR product was purified by a conventional method, and then digested with BamHI, followed by insertion into the BamHI site of the above-described pBS3. The DNA was used to transform competent cells of *Escherichia coli* JM109 (Takara Bio Inc.), and the transformed cells were cultured overnight on an LB plate containing 100 μM of IPTG, 40 μg/ml of X-Gal, and 25 μg/ml of kanamycin (Km). Single colonies of transformants were isolated by selecting the white colonies which appeared. Plasmids were extracted from these transformants, and those containing the desired PCR product were named pBS3ΔsucA.

The pBS3ΔsucA obtained in above (A) does not contain a region that allows for autonomous replication in coryneform bacteria. Therefore, when a coryneform bacterium is transformed with the plasmid, only transformants containing the plasmid integrated into the chromosome by homologous recombination will appear at low frequency. The *C. glutamicum* ATCC13869 strain was transformed with a high concentration of the plasmid pBS3ΔsucA by the electric pulse method, and the cells were applied to a CM-Dex plate (5 g/L of glucose, 10 g/L of polypeptone, 10 g/L of yeast extract, 1 g/L of KH$_2$PO$_4$, 0.4 g/L of MgSO$_4$.7H$_2$O, 0.01 g/L of FeSO$_4$.7H$_2$O, 0.01 g/L of MnSO$_4$.7H$_2$O, 3 g/L of urea, 1.2 g/L of soybean hydrolysate, 10 μg/L of biotin, 15 g/L of agar, pH was adjusted to 7.5 with NaOH) containing 25 μg/ml of kanamycin, and cultured at 31.5° C. for about 30 hours. In the cells which grew on this medium, the kanamycin-resistant gene and the sacB gene from the plasmid were integrated into the chromosome by homologous recombination between the sucA gene of the plasmid and the sucA gene on the chromosome of the ATCC13869 strain.

Subsequently, the single-crossover recombinants which were obtained were cultured at 31.5° C. overnight in CM-Dex liquid medium containing no kanamycin, and after suitable dilution, the cells were applied to a 10% sucrose-containing Dex-S10 plate (100 g/L of sucrose, 10 g/L of polypeptone, 10 g/L of yeast extract, 1 g/L of KH$_2$PO$_4$, 0.4 of g/L MgSO$_4$.7H$_2$O, 0.01 g/L of FeSO$_4$.7H$_2$O, 0.01 g/L of MnSO$_4$.4H$_2$O, 3 g/L of urea, 1.2 g/L of soybean hydrolysate, 10 μg/L of biotin, 15 g/L of agar, pH was adjusted to 7.5 with KOH) containing no kanamycin, and cultured at 31.5° C. for about 30 hours. As a result, strains which were sucrose-insensitive due to the curing of the sacB gene by the second homologous recombination were obtained.

The strains thus obtained include one in which the sucA gene was replaced by the mutant gene derived from pBS3ΔsucA, and one in which the sucA gene has reverted to the wild-type gene. Whether the sucA gene is the mutant gene or the wild-type gene can be easily confirmed by directly subjecting the bacterial cells obtained by culture on a Dex-S10 plate to PCR, and detecting the sucA gene. The analysis was performed using the primers for amplifying the sucA gene by PCR (SEQ ID NOS: 5 and 6), and strains that were determined to contain a smaller PCR product than the PCR product using chromosomal DNA of the ATCC13869 strain, as a template. In this way, sucA-disrupted strains were selected and used in the following experiment.

The L-glutamic acid-producing ability of the sucA-disrupted strains were evaluated by the following method. The strains were cultured on CM-Dex plate medium, and each of the sucA gene-disrupted strains was seeded in a Sakaguchi flask containing 20 ml of a medium containing 30 g of glucose, 1 g of KH$_2$PO$_4$, 0.4 g of MgSO$_4$, 15 g of (NH$_4$)$_2$SO$_4$, 0.01 g of FeSO$_4$.7H$_2$O, 0.01 g of MnSO$_4$.7H$_2$O, 13.7 ml of soybean hydrolysate, 200 μg of thiamine chloride, 300 μg of biotin, and 50 g of CaCO$_3$ in 1 L of pure water (pH was adjusted to 8.0 with KOH), followed by a shaking culture at 31.5° C. After the culture, the amount of L-glutamic acid which had accumulated in the medium was determined, and the strain that exhibited the largest L-glutamic acid production yield was selected and named ATCC13869ΔsucA.

(1-2) Introduction of a Mutant yggB Gene

A mutant yggB gene prepared by inserting the IS (Insertion sequence) into the C-terminus of the yggB gene was introduced into the ATCC13869ΔsucA strain (FIG. 1). The nucleotide sequence of the mutant yggB gene and the amino acid sequence encoded thereby are shown in SEQ ID NOS: 7 and 8, respectively. The mutant yggB gene-introduced strain was named ATCC13869ΔsucAyggB::IS.

Alternatively, the strain in which the IS is inserted into the C-terminal region of the yggB gene can also be constructed by amplifying three fragments with PCR as follows.

First, PCR is performed using the oligonucleotides of SEQ ID NOS: 44 and 45 as primers and the chromosomal DNA from the ATCC13869 strain as a template, to thereby obtain an upstream fragment of the yggB gene. Another PCR procedure is performed using the oligonucleotides of SEQ ID NOS: 46 and 47 as primers and the chromosomal DNA from the ATCC13869 strain as a template, to thereby obtain the IS fragment. The oligonucleotides of SEQ ID NOS: 45 and 46 are partially complementary to each other. Next, PCR is performed using approximately equal molar amounts of these PCR products as templates and the oligonucleotides of SEQ ID NOS: 44 and 47 as primers, to thereby prepare a fragment where the yggB fragment is inserted upstream of the IS.

PCR is performed using the oligonucleotides of SEQ ID NOS: 48 and 49 as primers and the chromosomal DNA from the ATCC13869 strain as a template, to thereby obtain a downstream fragment of the yggB gene. The oligonucleotides of SEQ ID NOS: 47 and 48 are complementary to each other. The yggB downstream fragment and the fragment described above comprising the yggB fragment inserted upstream of the IS are mixed in approximately equal molar amounts, and PCR is performed using the oligonucleotides of SEQ ID NOS: 50 and 51 as primers, to thereby obtain a yggB fragment into which the IS is inserted (yggB::IS). The fragment is treated with SacI and inserted into the SacI site of pBS4S (WO 2005/113745 and 2005/113744), to thereby construct a plasmid which can be used to replace the yggB gene on a chromosome with the yggB::IS. The ATCC13869 strain has a plurality of similar IS sequences. Therefore, to obtain an IS-inserted yggB gene completely corresponding to SEQ ID NO: 7, it is necessary to confirm the nucleotide sequence of the plasmid to determine whether the plasmid has the same sequence. However, differences in some nucleotides in an IS-derived region does not have a great influence on the function of the IS-inserted yggB gene. The resulting plasmid is used to replace the yggB gene on the chromosome by a conventional method, resulting in a strain in which the IS is inserted into the chromosomal yggB gene.

(1-3) Construction of a pta-Amplified Strain

To construct a strain in which the expression of a phosphotransacetylase (pta) gene is enhanced, the phosphotransacetylase (pta) gene derived from *C. glutamicum* ATCC13869 strain was amplified by PCR and cloned into the shuttle vector pVC7. pVC7 (US 20030134397) is constructed by inserting a fragment obtained by digesting pAM330 (a cryptic plasmid from the ATCC13869 strain (GenBank Database Accession No. D00038)) with HindIII and blunt-ending, into the BsaAI site of pHSG399 (Takara Bio). PCR was performed using synthetic DNAs (SEQ ID NOS: 9 and 10) designed based on the known nucleotide sequence of the phosphotransacetylase gene of *Corynebacterium glutamicum* ATCC13032 (GenBank Database Accession No. NC_003450, SEQ ID NO: 40), to thereby obtain a gene fragment containing the entire ORF of the phosphotransacetylase gene and its promoter region. This PCR product was purified by a conventional method, and digested with BamHI and Kpn I, and inserted between the BamHI site and Kpn I site in pVC7. This plasmid was used to transform competent cells of *Escherichia coli* DH5α (Takara Bio Inc.), and the transformed cells were cultured overnight on an LB plate containing 100 μM of IPTG, 40 μg/ml of X-Gal, and 25 μg/ml of chloramphenicol (Cm). Thereafter, single colonies of transformants were isolated by selecting the white colonies which appeared. Plasmids were extracted from these transformants, and the plasmid containing the objective PCR product was selected and named pVC7-pta.

(1-4) Confirmation of Enhanced PTA Activity in the ATCC13869ΔsucAyggB::IS Strain ATCC13869ΔsucAyggB::IS strain was transformed with pVK9. The transformation was performed by the electric pulse method, and the cells were cultured at 31.5° C. for about 30 hours on a CM-Dex plate containing 25 μg/ml of kanamycin. This strain containing the pVK9 was named ATCC13869ΔsucAyggB::IS(pVK9).

pVK9 (US Patent 20050196846) is a shuttle vector. It is constructed by inserting a fragment obtained by digesting pHK4 (JP-A-05-007491) with BamHI and KpnI and blunt-ending (a fragment able to automatically replicate in coryneform bacteria), into the blunt-ended AvaII site of pHSG299 (TAKARA BIO INC.).

Subsequently, the ATCC13869ΔsucAyggB::IS(pVK9) strain was transformed separately with pVC7 (a control plasmid) and pVC7-pta (a plasmid for amplifying PTA). The transformation was performed by the electric pulse method, and the cells were cultured 31.5° C. for about 30 hours on a CM-Dex plate containing 25 μg/ml of kanamycin and 5 μg/ml of chloramphenicol. The strains into which the above-described plasmids were introduced were named ATCC13869ΔsucAyggB::IS (pVK9, pVC7) and ATCC13869ΔsucAyggB::IS(pVK9, pVC7-pta), respectively.

To determine the PTA activity of these strains, a crude enzyme solution was prepared by the following method. First, each strain was cultured in CM-Dex liquid medium at 31.5° C. The OD 660 was determined using Taitec Mini photo 518R digital colorimeter, and the culture was continued until the OD reached 0.6 to 0.9, followed by collecting the cells. The following operations were performed at 4° C. The cells were washed with 50 mM Tris/HCl (pH 7.0) solution twice and then suspended in a buffer (50 mM Tris/HCl (pH 7.0), 10 mM $MgCl_2$, 1 mM EDTA, 1 mM DTT, and 30% (w/v) glycerol) to 4 g (wet weight)/ml. The cells were homogenized with an ultrasonic homogenizer (Bioruptor) and centrifuged (15,000 g, 60 min). The supernatant was used as the crude enzyme solution. The procedures for quantifying the protein level in the crude enzyme solution are as follows. Each crude enzyme solution and BSA (bovine serum albumin) with a known concentration (for creating a calibration curve) was allowed to react with a CBB solution (Nacalai tesque protein assay CBB solution) to develop a color, and then the protein concentration was quantified by determining the OD 595 nm using an apparatus for determining enzymatic activities (Molecular Devices, spectra max 190).

Subsequently, the PTA activity was determined with reference to the known method (D. J. Reinscheid, S. Schnicke, D. Rittmann, U. Zahnow, H. Sahm and B. J. Eikmanns (1999) Microbiology. 145: 503-513). Specific procedures are shown below. The enzymatic reaction was initiated by adding the crude enzyme solution to the reaction solution of 100 mM of Tris/HCl (pH 7.6), 5 mM of $MgCl_2$, 0.5 mM of L-cysteine hydrochloride, 20 mM of $NH_4Cl_2$, 1 mM of CoA, and 20 mM of acetyl phosphate. The generation of acetyl-CoA was detected by determining the OD 232 nm using an apparatus for determining enzymatic activities (Molecular Devices, spectra max 190), to thereby determine the PTA activity. Table 1 shows that ATCC13869ΔsucAyggB::IS(pVK9, pVC7-pta) has a higher PTA activity as compared to the control strain.

TABLE 1

|  | ΔABS/sec/mg | Relative activity to control defined as 1. |
|---|---|---|
| ATCC13869ΔsucAyggB::IS(pVK9, pVC7) | 0.365 | 1 (Control) |
| ATCC13869ΔsucAyggB::IS(pVK9, pVC7-pta) | 1.550 | 4.27 |

Example 2

L-Glutamic Acid Production by the PTA-Enhanced ATCC13869ΔsucAyggB::IS Strain

The effect of enhancing PTA activity on the yield of L-glutamic acid during fermentation was evaluated by culturing C. glutamicum ATCC13869ΔsucAyggB::IS(pVK9, pVC7) strain and ATCC13869ΔsucAyggB::IS(pVK9, pVC7-pta) strain by the same method as shown above (1-1). The results are shown in Table 2. The yield of L-glutamic acid by the PTA-enhanced strain was found to be higher than that of the control strain.

TABLE 2

|  | Fermentation yield of L-glutamic acid (mean ± standard deviation % (n = the number of samples)) |
|---|---|
| ATCC13869ΔsucAyggB::IS(pVK9, pVC7) | 47.0 ± 0.2 (n = 4) |
| ATCC13869ΔsucAyggB::IS(pVK9, pVC7-pta) | 50.5 ± 0.9 (n = 4) |

Example 3

Production of L-Glutamic Acid by the Strain in which Activities of PTA and Phosphoketolase are Enhanced

Next, the combined effect of the enhanced phosphotransacetylase activity and enhanced phosphoketolase activity on L-glutamic acid production was examined.

A phosphoketolase expression plasmid was constructed as follows.

(A) Construction of pVK9-xfp

To amplify the phosphoketolase gene (the sequence information has been disclosed: AY518213:gi:41056820) by PCR and insert the gene into the shuttle vector pVK9 used in Example 1, the chromosomal DNA was extracted from *Bifidobacterium animalis* using Wizard Genomic Purification Kit (Promega Corporation). PCR was performed using a chromosomal DNA of *B. animalis* as a template and synthetic DNAs of SEQ ID NOS: 11 and 12 as primers, to thereby obtain a gene fragment containing the entire ORF of the phosphoketolase gene and its promoter region. This PCR product was purified by a conventional method and then digested with Xba I, followed by insertion into the Xba I site of pVK9. Competent cells of *Escherichia coli* DH5α (Takara Bio Inc.) were transformed with this DNA, and the transformed cells were cultured overnight on an LB plate containing 100 μM of IPTG, 40 μg/ml of X-Gal, and 25 μg/ml of Km. Thereafter, single colonies of transformants were isolated by selecting the white colonies which appeared. Plasmids were extracted from the transformants, and those containing the desired PCR product were selected and named pVK9-xfp.

(B) Construction of pVK9-PS2_xfp

The overlap PCR method (R. M. Horton, H. D. Hunt, S. N. Ho, J. K. Pullen, and L. R. Pease (1989) Gene 77: 61-68) was performed to obtain a DNA fragment in which a promoter region of the phosphoketolase gene of *B. animalis* was replaced with the PS2 promoter. Specifically, PCR was performed using pPSTG1 (Y. Kikuchi, M. Date, K. Yokoyama, Y. Umezawa, and H. Matsui (2003) Appl. Environ. Microbiol. 69: 358-366) as a template and synthetic DNAs of SEQ ID NOS: 13 and 14 as primers, to thereby obtain an amplified product of the PS2 promoter. Another PCR procedure was performed using pVK9-xfp as a template and synthetic DNAs of SEQ ID NOS: 15 and 16 as primers, to thereby obtain an amplified product of the *B. animalis* phosphoketolase gene. The primers of SEQ ID NOS: 14 and 16 are complementary to each other. Next, to obtain a fragment where the PS2 promoter is inserted upstream of the *B. animalis* phosphoketolase gene, the PS2 promoter and *B. animalis* phosphoketolase gene product were mixed in approximately equal amounts, and PCR was performed using the mixture as templates and synthetic DNAs of SEQ ID NOS: 12 and 17 as primers. This PCR product was purified by a conventional method and then digested with Xba I, followed by insertion into the Xba I site of pVK9. The DNA was used to transform competent cells of *Escherichia coli* DH5α (Takara Bio Inc.), and the transformed cells were cultured overnight on an LB plate containing 100 μM of IPTG, 40 μg/ml of X-Gal, and 25 μg/ml of Km. Thereafter, single colonies of transformants were isolated by selecting the white colonies which appeared. Plasmids were extracted from these transformants, and those containing the plasmid having the desired PCR product were selected and named pVK9-PS2_xfp.

(C) Production of L-Glutamic Acid Using a Strain with Enhanced Activities of PTA and Phosphoketolase C. glutamicum ATCC13869ΔsucAyggB::IS strain was transformed with pVK9_PS2_xfp in accordance with the above-described method, to thereby obtain a transformant strain, which was named ATCC13869ΔsucAyggB::IS(pVK9_PS2_xfp). Next, the ATCC13869ΔsucAyggB::IS(pVK9_PS2_xfp) strain was transformed separately with pVC7 (a plasmid for control) and pVC7-pta (a plasmid for amplifying PTA) and the transformed strains were named ATCC13869ΔsucAyggB::IS(pVK9_PS2_xfp, pVC7) and ATCC13869ΔsucAyggB::IS(pVK9_PS2_xfp, pVC7-pta), respectively.

C. glutamicum ATCC13869ΔsucAyggB::IS(pVK9, pVC7), ATCC13869ΔsucAyggB::IS(pVK9, pVC7-pta), ATCC13869ΔsucAyggB::IS(pVK9_PS2_xfp, pVC7), and ATCC13869ΔsucAyggB::IS(pVK9_PS2_xfp, pVC7-pta) strains were cultured in accordance with the method of (1-1) of Example 1. The results are shown in Table 3. The yield of L-glutamic acid from the strain having both enhanced PTA and phosphoketolase activity was found to be higher as compared to the strains in which either of the PTA or phosphoketolase was enhanced.

TABLE 3

|  | Fermentation yield of L-glutamic acid (%) (mean ± standard deviation (n = the number of samples)) |
|---|---|
| ATCC13869ΔsucAyggB::IS(pVK9, pVC7) | 47.0 ± 0.2 (n = 4) |
| ATCC13869ΔsucAyggB::IS(pVK9, pVC7-pta) | 50.5 ± 0.9 (n = 4) |
| ATCC13869ΔsucAyggB::IS(pVK9_PS2_xfp, pVC7) | 54.5 ± 0.2 (n = 3) |
| ATCC13869ΔsucAyggB::IS(pVK9_PS2_xfp, pVC7-pta) | 56.6 ± 0.7 (n = 6) |

Example 4

Construction of a Strain in which PTA Activity is Enhanced by Disrupting a ramB Gene that Encodes a Transcription Factor, and Evaluation of its Effect It is known that the expression of the PTA gene is negatively regulated by the transcription factor RamB, and the PTA activity is increased in a ramB gene-deficient strain (Journal of Bacteriology May 2004 2798-2809). Therefore, a ramB-deficient strain is constructed, and its effect on the yield of L-glutamic acid during fermentation is examined.

(4-1) Cloning of a Fragment for Disrupting the ramB Gene

A ramB gene is disrupted using pBS5T, which is a temperature-sensitive plasmid carrying the sacB gene (WO 2005/113745 and WO 2005/113744). A gene fragment which is derived from the ramB gene of the ATCC13869 strain and has a deletion in the ORF of the ramB gene is obtained by the overlap PCR method using synthetic DNAs designed based on the known nucleotide sequence of the gene from *Corynebacterium glutamicum* ATCC13032 (GenBank Database Accession No. NC_003450, the nucleotide sequence of ramB gene and the amino acid sequence encoded thereby are shown in SEQ ID NOS: 36 and 37, respectively) as primers. Specifically, PCR is performed by using the chromosomal DNA of *C. glutamicum* ATCC13869 strain as a template and synthetic DNAs of SEQ ID NOS: 19 and 20 as primers, to thereby obtain an amplified product corresponding to the N-terminal region of the ramB gene. Another PCR is performed to amplify a fragment corresponding to the C-terminal region of the ramB gene, using the chromosomal DNA of ATCC13869 strain as a template and synthetic DNAs of SEQ ID NOS: 18 and 21 as primers. The DNAs of SEQ ID NOS: 18 and 19 are complementary to each other, and they are designed so that a mutant ramB gene which is missing the entire ORF is amplified. Subsequently, to obtain the mutant ramB gene fragment missing an internal sequence, the above-described amplified products corresponding to the N-terminal region and the C-terminal region of the ramB gene are mixed in approximately equal molar amounts, and PCR is performed using the mixture as templates and using synthetic DNAs of SEQ ID NOS: 22 and 23 as primers. This PCR product is purified by a conventional method, and then digested with Xba I, followed by insertion into the Xba I site of the above-described pBS5T. Competent cells of *Escherichia coli* DH5α (Takara Bio Inc.) are transformed with this DNA, and the cells are cultured overnight on LB medium containing 100 μM of IPTG, 40 μg/ml of X-Gal, and 25 μg/ml of Km. Thereafter, single colonies of transformants are isolated by selecting the white colonies which appear. Plasmids are extracted from these transformants, and those containing the desired PCR are selected and named pBS5T-ramB.

(4-2) Construction of a ramB Gene-Disrupted Strain

First, ATCC13869ΔsucAyggB::IS strain is transformed by the electric pulse method with a high concentration of pBS5T-ramB, and the transformed cells are cultured at 25° C. for about 60 hours on a CM-Dex plate containing 25 μg/ml of kanamycin. This transformant is cultured with shaking at 34° C. overnight in CM-Dex liquid medium and after appropriate dilution, the cells are cultured at 34° C. for about 30 hours in CM-Dex medium containing 25 μg/ml of kanamycin.

In the strain which grew in this medium, the kanamycin-resistant gene and the sacB gene derived from the plasmid are integrated into the chromosome by homologous recombination between the mutant ramB gene of the plasmid and the ramB gene on the chromosome of the ATCC13869ΔsucAyggB::IS strain.

Next, these single-crossover recombinants are cultured at 31.5° C. overnight in CM-Dex liquid medium containing no kanamycin, and after appropriate dilution, the cells are cultured at 34° C. for about 30 hours in 10% sucrose-containing Dex-S10 medium (100 g/L sucrose, 10 g/L polypeptone, 10 g/L yeast extract, 1 g/L $KH_2PO_4$, 0.4 g/L $MgSO_4.7H_2O$, 0.01 g/L $FeSO_4.7H_2O$, 0.01 g/L $MnSO_4.4H_2O$, 3 g/L urea, 1.2 g/L soybean hydrolysate, 10 μg/L biotin, 2 g/l sodium acetate, pH 7.5 (KOH)) with no kanamycin. As a result, strains which are sucrose-insensitive due to the curing of the sacB gene by the second homologous recombination are obtained.

The strains thus obtained include one in which the ramB gene is replaced by the mutant gene derived from pBS5T-ramB, and one in which the ramB gene reverts to the wild-type gene. Whether the ramB gene is the mutant gene or the wild-type gene can be confirmed by directly subjecting bacterial cells obtained by culture on Dex-S10 agar medium to PCR. A strain having only the mutant ramB gene is selected and named ATCC13869ΔsucAyggB::ISΔramB.

(4-3) L-Glutamic Acid Production Using the ramB Gene-Disrupted Strain

ATCC13869ΔsucAyggB::ISΔramB is transformed with pVK9 (a plasmid for control) and pVK9_PS2_xfp (a plasmid for amplifying the phosphoketolase gene (PKT) separately). The transformation is performed by the electric pulse method, and the cells are cultured at 31.5° C. for about 30 hours on a CM-Dex plate containing 25 μg/ml of kanamycin. The plasmid-introduced strains are named ATCC13869ΔsucAyggB::ISΔramB(pVK9) and ATCC13869ΔsucAyggB::ISΔramB(pVK9_PS2_xfp), respectively. These strains are evaluated by culture in accordance with the method of (1-1) of Example 1 together with ATCC13869ΔsucAyggB::IS(pVK9) strain and ATCC13869ΔsucAyggB::IS(pVK9_PS2_xfp) strain constructed in Example 1. This procedure confirms the improvement of the L-glutamic acid yield by ramB gene disruption and by a combination of ramB gene disruption and PKT enhancement.

Example 5

Construction of a pta Activity-Enhanced Strain by Modification of a Promoter of the PTA Gene and Evaluation of the Effect The PTA activity can be enhanced by modifying a promoter of the pta gene. It is known that the pta gene promoter has two regions that are thought to be involved in the RamB-mediated negative regulation that affects the PTA activity (J. Bacteriol. 2004 May; 186(9): 2798-2809.). Therefore, strains which are modified in only one of the RamB-binding sites in the pta promoter or both of the RamB-binding sites in the pta promoter, are constructed to examine the effect on the L-glutamic acid fermentation yield.

(5-1) Construction of Plasmids for Mutating the pta Promoter, PBS5T-m1PTA, pBS5T-m2PTA, PBS5T-m1m2PTA A gene fragment containing the ORF region and the promoter region of the pta gene derived from ATCC13869 is obtained by PCR using synthetic DNAs designed based on the known nucleotide sequence of the gene from *Corynebacterium glutamicum* ATCC13032 (GenBank Database Accession No. NC_003450). Specifically, for amplifying the promoter region of the pta gene, PCR is performed using the chromosomal DNA of *C. glutamicum* ATCC13869 strain as a template and synthetic DNAs of SEQ ID NOS: 24 and 25 as primers. This PCR product is purified by a conventional method and digested with Xba I, followed by insertion into the Xba I region of pUC19 (Takara Bio Inc.). Competent cells of *Escherichia coli* DH5α (Takara Bio Inc.) are transformed with the DNA, and cultured overnight in LB medium containing 100 μM of IPTG, 40 μg/ml of X-Gal, and 50 μg/ml of Amp. Thereafter, single colonies of transformants are isolated by selecting the white colonies which appear. Plasmids are extracted from these transformants, and those containing the desired PCR product are selected and named pUC19-PTA.

Next, a mutation is introduced into the pta promoter region using Site-Directed Mutagenesis Kits (STARATAGENE). PCR is performed using pUC19-PTA as a template and synthetic DNAs of SEQ ID NOS: 26 and 27 as primers in accordance with the manual supplied with the kits, which results in a plasmid having a mutation in one of the first RamB-binding sites. This plasmid is named pUC19-m1PTA.

Next, PCR is performed using pUC19-m1PTA as a template and synthetic DNAs of SEQ ID NOS: 24 and 25 as primers, to thereby obtain an amplified product containing the promoter region of the pta gene having the mutation. This PCR product is purified by a conventional method and inserted into the above-described SmaI region of pBS5T. Competent cells of *Escherichia coli* DH5α (Takara Bio Inc.) are transformed with this DNA, and the cells are cultured overnight in LB medium containing 100 μM of IPTG, 40 μg/ml of X-Gal, and 25 μg/ml of Km. Thereafter, single colonies of transformants are isolated by selecting the white colonies which appear. Plasmids are extracted from these transformants, and sequence analysis confirms that the plasmid has the desired mutation with no sequence errors in other nucleotides. Thus, the plasmid is named pBS5T-m1PTA.

In the same way, a plasmid having a mutation in the second RamB-binding site is constructed by performing PCR using synthetic DNAs of SEQ ID NOS: 28 and 29, and then inserting the desired sequence into pBS5T. This plasmid is named pBS5T-m2PTA. In addition, a plasmid having mutations in both RamB-binding sites is constructed by the same procedures as described above and named pBS5T-m1m2PTA.

(5-2) Construction of Strains Harboring the Promoter-Modified pta Gene

Strains having modified PTA promoters are obtained from ATCC13869ΔsucAyggB::IS strain in accordance with the method of Example 4. The mutation is confirmed by analyzing the sequence of the promoter region. The strains with modified RamB-binding sites in the pta promoter are named ATCC13869ΔsucAyggB::ISm1, ATCC13869ΔsucAyggB::ISm2, and ATCC13869ΔsucAyggB::ISm1 m2.

(5-3) L-Glutamic Acid Production by Using the Strains Harboring the Promoter-Modified pta Gene The ATCC13869ΔsucAyggB::ISm1 strain, ATCC13869ΔsucAyggB::ISm2 strain, and ATCC13869ΔsucAyggB::ISm1m2 strain are each transformed with pVK9 (a control plasmid) and pVK9_PS2_xfp (a plasmid for amplifying PKT). The transformation is performed by the electric pulse method, and the transformed cells are cultured at 31.5° C. for about 30 hours on a CM-Dex plate containing 25 μg/ml of kanamycin. These strains are named ATCC13869ΔsucAyggB::ISm1(pVK9), ATCC13869ΔsucAyggB::ISm1(pVK9_PS2_xfp), ATCC13869ΔsucAyggB::ISm2(pVK9), ATCC13869ΔsucAyggB::ISm2(pVK9_PS2_xfp), ATCC13869ΔsucAyggB::ISm1m2(pVK9), and ATCC13869ΔsucAm1m2(pVK9_PS2_xfp), and are evaluated by culture in accordance with the method of Example 1 together with ATCC13869ΔsucAyggB::IS(pVK9) and ATCC13869ΔsucA(pVK9_PS2_xfp), constructed in Example 1. Improvement of the L-glutamic acid yield by the pta promoter modification and the combination of the PTA promoter modification and PKT enhancement is confirmed.

Example 6

Construction of a Strain in which pta Enhancement is Combined with the Enhancement of Enzymes of the Anaplerotic Pathway In order to evaluate the effect of combined enhancement of PTA and phosphoenolpyruvate carboxylase (PPC) or pyruvate carboxylase (PC), strains with enhanced activities of PTA and PPC or enhanced activities of PTA and PC are constructed.

(6-1) Construction of the ppc-Expressing Plasmid pVC-PPC

The ppc-expressing plasmid is constructed as follows. The ppc gene is amplified by performing PCR using synthetic oligonucleotides of SEQ ID NOS: 58 and 59 as primers and the chromosomal DNA of *C. glutamicum* ATCC 14067 strain as a template. The amplified DNA is blunt-ended and inserted into the SmaI site of pHSG399 (TAKARA BIO INC.), to thereby obtain the plasmid pPCF. Then, in order to remove the region upstream of the coding region of the ppc gene, pPCF is digested with DraI and SalI, and the obtained fragment is inserted into the SmaI site of pHSG398 (TAKARA BIO INC.) to obtain a plasmid having the ppc gene inserted in the reverse direction with respect to the lacZ gene, and is named pPCFds. Then, a DNA fragment containing an aspartokinase promoter and a region able to autonomously replicate in coryneform bacterium is prepared by digesting p399AKYB (JP6-62866) with PstI and ApaI and then blunt-ending, and the obtained fragment is inserted into the pPCFds which has been digested with SalI and blunt-ended, to ligate the aspartokinase promoter upstream of the ppc gene. A plasmid in which the aspartokinase promoter and the ppc gene are linked in the same direction was selected and named pAKPFds. The region in pAKPFds involved in autonomous replication in coryneform bacterium is derived from pHM1519, since the autonomous replication region of pVK9_PS2_xfp, and therefore, pAKPFds cannot co-exist with pVK9_PS2_xfp in coryneform bacterium. So, PCR is performing by using synthetic oligonucleotides of SEQ ID NOS: 60 and 61 as primers and pAKPFds as a template, and the amplified fragment is digested with KpnI and inserted into the KpnI site of pVC7 (JP2000-201692), which contains an autonomous replication region from pAM330. The obtained plasmid was named pVC-PPC.

(6-2) Construction of a Strain in which the pta Gene and the Ppc Gene are Amplified, and a Strain in which the Pta Gene and the pc Gene are Amplified pVC7 (control), pVC-PPC, or pBPYC6 (pc gene-expressing plasmid: JP2000-201692) is used to transform ATCC13869ΔsucAyggB::IS(pVK9) (see Example 2), ATCC13869ΔsucA(pVK9_PS2_xfp) (see Example 3), and ATCC13869ΔsucAyggB::IS m1(pVK9), ATCC13869ΔsucAyggB::IS m1(pVK9_PS2_xfp), ATCC13869ΔsucAyggB::IS m2(pVK9), ATCC13869ΔsucAyggB::IS m2(pVK9_PS2_xfp), ATCC13869ΔsucAyggB::IS m1m2(pVK9), and ATCC13869ΔsucAyggB::IS m1m2(pVK9_PS2_xfp) (see Example 5). These transformants are cultured and L-glutamic acid production is evaluated according to the method of (1-1) of Example 1. Thereby, improvement of L-glutamic acid production is confirmed by combining the modification of the pta promoter with the enhancement of PC or PPC, or by combining the modification of the pta promoter with the enhancement of PKT and PC or PPC.

INDUSTRIAL APPLICABILITY

The production method of the present invention enables efficient production of L-amino acids such as L-glutamic acid, L-glutamine, L-proline, L-arginine, L-leucine, and L-cysteine.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing an L-amino acid comprising culturing in a medium an L-amino acid-producing bacterium which has been modified to enhance phosphotransacetylase activity, and collecting the L-amino acid from the medium or the bacterium, wherein said phosphotransacetylase is encoded by a DNA selected from the group consisting of:
   (a) a DNA comprising nucleotides 1214 to 2641 of SEQ ID: 34,
   (b) a DNA comprising the nucleotide sequence of SEQ ID NO: 40,
   (c) a DNA which hybridizes with a nucleotide sequence which is complementary to the nucleotide sequence of nucleotides 1214 to 2641 of SEQ ID NO: 34, where said DNA hybridizes under stringent conditions and encodes a protein that has phosphotransacetylase activity, and
   (d) a DNA which hybridizes with a nucleotide sequence which is complementary to the nucleotide sequence of SEQ ID NO: 40, wherein said DNA hybridizes under stringent conditions and encodes a protein that has phosphotransacetylase activity,
   wherein said stringent conditions comprise washing at a salt concentration of 0.1×SSC, 0.1% SDS at 60° C.

2. The method according to claim 1, wherein the phosphotransacetylase activity is enhanced by a method selected from the group consisting of:
   A) increasing the copy number of the gene encoding phosphotransacetylase,
   B) modifying an expression regulatory sequence of the gene encoding phosphotransacetylase, and
   C) combinations thereof.

3. The method according to claim 1, wherein the phosphotransacetylase activity is enhanced by disrupting a ramB gene.

4. The method according to claim 1, wherein the bacterium is further modified to enhance an activity of a protein selected from the group consisting of D-xylose 5-phosphate-phosphoketolase, fructose 6-phosphate phosphoketolase, and combinations thereof.

5. The method according to claim 1, wherein the bacterium is further modified to enhance pyruvate carboxylase activity.

6. The method according to claim 1, wherein the bacterium is further modified to enhance phosphoenolpyruvate carboxylase activity.

7. The method according to claim 1, wherein the bacterium is selected from the group consisting of a coryneform bacterium, *Pantoea* bacterium, *Enterobacter* bacterium, and *Escherichia* bacterium.

8. The method according to claim 1, wherein the L-amino acid is selected from the group consisting of L-glutamic acid, L-glutamine, L-proline, L-arginine, L-leucine, and L-cysteine.

* * * * *